(12) United States Patent
Jiang et al.

(10) Patent No.: US 7,955,803 B2
(45) Date of Patent: Jun. 7, 2011

(54) UROTENSIN 2 AND ITS RECEPTOR AS CANDIDATE GENES FOR BEEF MARBLING SCORE, RIBEYE AREA AND FATTY ACID COMPOSITION

(75) Inventors: Zhihua Jiang, Pullman, WA (US); Jennifer J. Michal, Albion, WA (US)

(73) Assignee: Washington State Research Foundation, Pullman, WA (US)

( * ) Notice: Subject to any disclaimer, the term of this patent is extended or adjusted under 35 U.S.C. 154(b) by 248 days.

(21) Appl. No.: 12/061,863

(22) Filed: Apr. 3, 2008

(65) Prior Publication Data
US 2009/0254388 A1    Oct. 8, 2009

Related U.S. Application Data

(60) Provisional application No. 60/910,180, filed on Apr. 4, 2007.

(51) Int. Cl.
*C12Q 1/68* (2006.01)
*C12P 19/34* (2006.01)

(52) U.S. Cl. .......................................... 435/6; 435/91.2
(58) Field of Classification Search ........................ None
See application file for complete search history.

(56) References Cited

U.S. PATENT DOCUMENTS

2004/0053826 A1    3/2004    Matsumoto et al.
2007/0065843 A1    3/2007    Jiang et al.

OTHER PUBLICATIONS

Juppner H. Bone (Aug. 1995) vol. 17, No. 2, Supplment pp. 39S-42S.*
Hacker U.T. et al. But (May 1997), vol. 40, No. 5, pp. 623-627.*

* cited by examiner

*Primary Examiner* — Stephen Kapushoc
(74) *Attorney, Agent, or Firm* — Judy Jarecki-Black; Chad Kitchen; Merial Limited

(57) ABSTRACT

The present invention relates to the identification of single nucleotide polymorphisms (SNPs) in urotensin II (UTS2) and urotensin 2 receptor (UTS2R) genes and their associations with beef marbling score (BMS), ribeye area (REA), amounts of saturated (rSFA) and monounsaturated (rMUFA), and $\Delta^9$ desaturase activity $R_2$=16:1 to 16:0. The invention further encompasses methods and systems, including network-based processes, to manage the SNP data, haplotype data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

2 Claims, 14 Drawing Sheets

SEQ ID NO:1
GCCTTGAGATTGAATTTTTGCTGTGAATTTATCTTCATTTTTTAAAAGTAAATAATCTGTTTTGACTTTAATTTC
ATGCCTTGTCATTCCTCAGGCATTGTTGTTCAGTCACTAAGTTGTGTCAGACTCTTTGTAGCCCTATGGATTGCA
GTACACCAGGCTTCCTGGTCCTTCATTATCTCCCTGAGCTTGCTCAAACTCATGTCC[A/C]TTGAGTCAGTGAT
GGCATCCAACCATCTCATCCTTTGTCTCCCCCTTCTCCTCTTGCCTCCAATCTTTCCCAGCATCAGGGTCTTTTC
CAATGAGGTGGCTGTTTGCCTCAGGTGGCCAAAGTATTGGAGCTTCAGCTTCAGC[C/A]TCAGTCCTCCCAATG
AATACTTAGGGTTGATTTCCTTTAGGAAATCTTCAGGCATGAAGCCCCAAAGAAAAAATG[A/G]CAGTTCATCT
ATTCATTCACAAAAGATTAAAAAAGAAAATCAACACATTTCACGCAGTGCTCCACAATACTTCTGCTGGGTAAGA
CTCATAAATCCATGTCCCTGTCTTGGACACTTCAACTCCTGTCTGATCCTTTCTTTAACTAGAGATTTATTGCTC
TCAATTACTCCTTTTTGCCAGATTTATAAACGTAACTGTTCTTTATTTAATACCTATTTTGTACACTAGGCAACA
AGACAGTAAATTTATTGTCTATGAGTTGCTACTTTGAAAAATTACATCAATGCAGAGTGATTGCTTTTCAGCCTT
CCTAGCCAATAAATTCATTTCTTTTTTTTTTTTTGTAGGGGATGATATGAGGTCATAGGATAATATATATAATC
GCTGATTACAGAATTAGAAGAAGCAAGTTGCAGGCAACTGCTCTAACACTGGACTCTACCCCGAGAAGGAGCAA
GTTGGAAGAAGCTAAGAAGGAAGACTTCTATCTCCTGCCAATCATGTATAAGCTGGTCTCCTGCTGTTTGCTTTT
CATAGGATCCTTAAATCCGCTCCTGTCTCTTCCTGTCCTTGACTCCAGGCAAGAGTCCCTGCAGCTCTTAGGTAA
GATGATTTTTTTCCCCTTATGTTAGTCTTGAACAAGTCTTCAAGGGTCTTAAATGCAAAGTTAAAGATGAAAATT
CTCTCTTAAAGGAGTCTTGTTAATAGTCCCAGCTATGAAAAGAATTCTGAGGATTCTTAAGGCATGTCTCAGAGT
CAAGAATGGATACAGTTTTTTCCTTTCTAAAATATAAAAGTAGAAGGGGAACATTGCTTATTTAACGTGACTTCT
GTAATTCTGAGTTATTTTGGTCAGTCTTTTTTTTCTGTTTTGAAAATAGCACTAAATTTAAAACACCATTGCTTT
TAGTCTTTATTTTAAGTGAACTGGTTGAATGTAGAACTGGTTGTTCCAATTATAGATTAAAGTATTTTGATTTTA
TCTTATATTATTTTAAGTTAAAAGGCAATCATCTGACATGTGTTACATGAAAAAAAAATGTTTTTTAAAATATAA
AAAAGTAACCAGCTGGGACTAGAGTAGACACAGATTTCCAAGTTCATTTTATCTTTTCCTTCTGGTTTATGTTTC
ATTCAGTTCAATTCTAAGTTGAATTTTTTAAAGTGTATCAATCAAGGAGATACTTATTGTACTTTTAGCTCTTCA
TTTAACTTAAGAAATGAAAAGGTTGGGGAAAAAAAGAAAAGAAAAAGTTGATGTTTGGGGATTGTGTTCATAAAC
ATTTTAACTGGATTTTAACTTGTCTTTAATTGTGGATACTTTTAGACATTTTTTTAAATAAAGGAAATAAAACT
CTGGTAAGCCAGTAATTTTATAATTTCTAGTCCATAAGTTTCTCCAAAGCAGCTTTCTTTTTTTTTTTTTTTGA
TAATTTAAATTTTATTTTATTTTTAAACTTTACATAATTGTATTAGTTTTGCCAAAGCAGCTTTCTGATAATAGT
CAAGCACTAATTCGTGCACAATTAATCACTTTCCAGAGTCACTGAACTCAGAAGTGGCAGTCATCTTAATGGTTA
AAATGAGCATTAACTTTATCGAATCTCTGCTATTTAAAAAAAAAAAAAAAACTTTGAAAAGCATAAGGTGAAACG
AAGAATGAATATTCAGATATTACTGACATCCTCAAAAAATTACATGTCATTATTATGATTTTTAAAAACTTGAG
TGAGTGTAGCATCCCCTTTCCAATTCTTAATAGGTGGCAGCTTATCTTAGCATTTTGCCTGAATTTTTCCTAC
TTACTTGTTTCTCCATAAATGATCCTTCCCTGGTGGCTGAGCAATGCAAGAGACTCTGGTTCAATCCCTGGGTTG
GGAAGGTCCCCTGGAAAAAGAAATGGCAATCTGCTCCAGTATTCTTGCTTGAAAAATTCCATGGACAGAGGAGTC
TGGTGGGTCGCAGAAGAATCGGACATGACTTGGCAACTGTAAACAAACAACAAAACAAATGATCCTTCATGACAA
AAATATTGATATGTAGCCAAACTTTGTAGACTTTCATTAACATTCTTCAGAAGTACCATGAAGCCTTCATGATGG
CTTGCTTTTTATTCTGCAATCAAGGTTGGAGCTGAGGGTTTGAAAGCCTTAGTGAAGCAGGCACTCCCTGCTTCA
CTGCTTTTACAGGACTCCCTGGGGGCTCTGATCACCGCAAGGCAGAAACCTGCCAAGAGAACAATCTGGGCCCAG
TATCACTCACCAGCCCTCACACTCACCTTTCGCACACCTGACACAAACTTACCATCCATCTTCTATGCTACCAAG
CTGACCAAATTACATGCTGAAAATGTTGCTATCAACTTGTTCAAAGAATATTGTAAAGCTGACTTGTTTCTGATC

FIG. 1A

ATTGTATCTAAATCTTAGAGGCCAGAGAAGAGGTGATGTTATCCTATTTGCTTTAGGTGTGTGTGAGTGAGTCAC
TCAGTTGTGTCCAACTGTTTGTCATCACCATGGATATTAGCCCACCAGTCTCCTCTGTCCATGGGATTCTCCAGG
CAAGAATACTGGAGTGGTCACCATTCCCTTCTCCAGGGGATCTTCCTGACCCCAGGGATCAAGCCTGGGTCTTCT
GCATTGCAGGCAGATTCTTTATTGTCTGAACCACCCGGTCGGAAGAACATAAACAAGCCCGTCTTTTAGAAAACC
ACTCCTTTACTTTTCCTCTCACTCCAATTTCGCCACCCCTATATCTAAAAGCAAAAGGCAAATGATAGCAGTAGG
TAAACAGAGACGAAGAAGAATCACTTTGTAAGTGGAAATGTTTTTTCACTGATCCTGTGGCTCAGCCCAATCCTT
TTTTTTTTTTTTTGATTTTTAACATTTTTAATTTCTTTACTTTTTGGATCACATGGGATCTTAGTTCCCCGACC
AGGCATTGAACCCACACCCTCTGCAGTGGAAGTGTGAAGTCTTAAGCACTAGACCACCAGGGAAGTCCCAGCCCT
ACCTTCTTATTCAGGGTGGTGAGCATCCAGCAAGGCTGTGCAGGCAGGAGGAGTCAGGATGAGAACCATGCCTCA
TGATTTCCTGTTCTGCTGGCTTGCAAATTGGACTGTAGCGTTCCCACTTCTCTGTTAAAATACTGCTAATGACAA
ACCATGAACTCAGTATTTGAAATCTGTCTAGTATTAGCTTCCTGTTCCTGGTGCATGCTCATGCTCAGTCACTCA
GTTGTGTCCCACTCTTTGTGACCCCATGAGCCTCCTCTGTCCATGGGATTTCCCAGGCAACAATACTGGAATGGG
TTGCCATTTCCTCCTCCAGGGGATCTTCTCAACCCAGGGATTGAACCTGTTTCTCCCGCATTACAGGCAAATTCT
TAACCACTGAGCCCCCTGGGAAGCCCCTCCCTGTCCCTGGTACCTCCCTAAAGACAATGGGGAACAGAACTGAAG
CAGGAGCTGTCACTAATATCAATCATTGCTCTGTGTAGCACCTGAAGATGTCAGATCAACTCTGGATGAGCTGGA
AAGAGCGTCTCTTCTGCAGATGCTGCCAGAGATGTCAGGCGCAGAGACAGGAGAGGGTCTTAGGAACACAGGTAA
AATGACTCGTGTTTACAGGCTGTCTGATTTCTTTGCTACTGAATTTACTCTGAGT[G/A]ATCACACTCTCCCCT
CCTGCATACAGTCTTCCTCTGCCATCTTCTGTCTCCTTTTTCTCAGCAACTCCTTGCAAGCATCCTTCTCTGCTT
GGCCCCTCGGCATATTTGTTCTCTGTATGATTTGGGGGGTGGGAGGCAAGGGGAGGGAAGAAGAGCATTATCCCA
GTTTTCAATAAGTACAATTTACAATGCTGGTTTCCCTCTTAGATGAGTTAATCTATCTGTATCTCAAATTCTTAA
ACCAGTACACAGGAATGATTAAAAAACAAAATTCCCATCGCATGGGGTTATTGAGAAGATTCAATGAGGAAATGC
AAGTAAAATGTTCATCACAAACACAAAATAACCCATGTCAGCTTTTACTGTTTTCTCAGTGACAGCGTTCCTCCT
AGCACAGATACAAATGCTCAGAACATTCTGGAGTCTTTTAATAAATTTGGTTTTGTAGAAAGAAATTCATGTGTG
ATAAAGTATTGTTGACAAACTACTGAACTGCTAACTCACTGAGGAAGATGCAGTGCCCTTTGTGAACTCTGGGGG
CTAGAAAAGAGCCAGGTGCTTGCCTGTCCTCCATCAAATAAATATCACTGCGGTGTGAAGAAAGG[A/C]AAACC
AGAAACTAGACATGATTTAGTAATATTCTATTTTGTATGTTTTAAATAAGACAAAGATAAAATGGAAATAATAGA
TCTGATGATGAATGGTTTCAAAATACTGTTTTCCAGATCCCATTACCAACATTTTTTACCCAAGAGGAAACATGA
GAAAGGTAAGTAGGTCCTATATGAGAGTTAGGATAAAAAAGGTGAACATTTCTATGCCTTGACTTTAGAGGAGCC
TCAGTAGGAACCAGTCAAGCCTTCTCAGTACAAATCTTAACACCCAGTATTATTTCAAAGCATTATTTTTTTCC
AAATTTTGATCCATGTAAAATGGGGATACAACAAGAACTTACCTAGTGTTCATCTCTGATAAATGATGATAACAA
GTTTTAGAGAATCAAAAATAGATAAAGCCCTTGCCCTCAAGCCTGTCATCCACTTGCGCTGTGTCACTGATTATC
TTCACTGGGTCCAAGGACCAGCAGTGCTGGTGTCACACGGAAGCTTGTGAGAAACGCAGACTCACCCCACCCCTC
ACACCTACTGAATCAAAATCTGCATCTTAACAGGATTTCCCCACGTGGTTTGTATGCACAGTAAAGTTTGAAAAG
CACTGTCATATAATATCTAAATGGAAGAAAGGCATGGTCGAAACATTGAGAGGGAATATGTGTGGTAAAGGAGAA
TATGAAGGAGATAATTTTGGGTGCAAAAGGCAGACTACAATAGGACATGATTAATGAAAATATTAAATGGTTAGA
AATGGTGCACAATTAATGGAGGACCTTAACTGCTACAAGAGAAATCGGTTTTGATCATTATCAACCCCTCAAACT
AAACTGAGCTCAGTTGTTCAGTCATGTCTGACTCTTTGGAACCCCATGAGCTGTAGCCCTGCCAGGCTAGTCTGT
CCATGGGATTTCCCAGGCAAGAATACTGGAGTAGGGTACCATTTCCTTTCCAGGGAATCTTGCTGGCCTAAGGAT

FIG. 1B

CAAACCTGCGTCACTTGCGTTTCCTGGACTGGCAAGTGAATTTTTTACCACTAGCCCCACCTGGAAAGCCCCAAG
CTAAATTAGTGTTTCCTAAAGGATTTTCTGTAAGGTCCTTTGAATTACCCTGTAGCTCTTTTGGTAAAGAACCTG
CCTGCAATACAGGAGACCCGGGTTCAATTTCTGGGTCAGGAAGATCCCCAGGAGAAGAAAATGGCAACCCACTTC
AGTATTCTTGCCTGGAGAATCCCATGGGTAGAGGAGCCTGGTGGGCTACAGTCTATGGGGTCGTAAGAGTCAGAC
ACAACTTAGCGACTAAACCACCAAAGGATTTTCTGTGAATATCAGTCCCATAGAGTCAGTCTACAGGGCTGCCCT
GCATTCTAACCCCTCTCCTGTCCTGGCAATTCTTTGTGTATAAAGCCTCCAGGAAATGAGATAAATGTATTTAAT
TTTAATCAAGAATTTCCCAAATATTTTGACCAGAAACATCTTCTTTTGGTGTAGTGCCCACTAACCTCCTTGTAA
AAATATACCATGAAAGCCCTCAATTCTGAAGATGGCATACACTGCCTGAGGTTCCCAGGTAGGGTAGACCACACA
GAAGGGGAGGGTGTGGCTCCTATTACATTAAAAGTTATCACTCAGATATTTATATTCTTCTGAATAGAAGATTA
TGGTGAAAGACTCTAAAATCATAAAGGTGATTAGTAGAGATGCTCATAAAATCCTAGAATAAAAAGAAAACTAAA
GGTCCATGATTAATTTCAAGACAAATAAAAGACCTGATTTACACAGAAGACATTAAATGTACAGAACATGTTACT
GAGAGATGAAATAGAAACAGGTAAATGAAGGTTTAGGAAAATTCATGGCAATCACGAGGCTAAATAGACTGGATG
GACCACAGGTTGGGCACAAGGAGACCTTTCAGAGTCTACATACTGGGTGCTCACTGCAATTCTATCCCATGAAAC
AGCAAGAAAACCCTTTTTAAAACCCTTTTAAAGGTCCTGTATCTGAGTAAGGTTCATTTGTGTGTGTATGGCA
CTCAATTAATTGATAACCTATTTTTTTAATTTCAGGCCTTCTCTGGGCAAGATCCTAAGCTTTTCCTGAGTGACC
TTTTGTCCAGAATTAGGAAACAATCTAAGAAACGTGGACCTTCCTCTGAATGCTTCTGGAAATACTGTGTCTGAA
GCAAAATGACCCTCTACTAGTTACCTCCAAGACGACCATCTGAGAAAATGTAAAATAAAGATGCTTGATTTGAAA
GCAGTATAGATGAAAAACTAGGCAAGCTAGACCCTGTTCATTATTATTTGGAAAATAAATCCTCTATGTTTTGCA
GATACTATGAGTGGTTGTTTTACTTAAAAACGTATCCTGAAAAACAAACAAAAAAAGTACCCTGAAAATCTATAC
TTTTTCTTTTTAAAAATAATTTTATTTATTTTTGGCTGTTCTGGATCTTCGTTGCTGTGCAGGCTTTTCTCTAGT
TGACGTGAGCGGGGCTGCTCTCTAGTCGTGTTGCACAGGCTTGTCACTGTGGTGGCTTCTCTTGTTGCAGAACAC
GGACTCTGGGGCACACGGGCTTCAGCTGTGGCTCCCGGGCTCTGGAGCACAGGTTCAGTAGCTGTGGCACGTAGG
CTTAGCTTCTCCGCGGTATGAGGGATCTTCCTGATCAGGGATCAATCCCAGTCCCCTGCATTGACAGGTGAATTC
TTTACCACTGAGCTACCAGGGAAGCCCCTA

FIG. 1C

SEQ ID NO:2 (TA insertion present at nucleotides 379-380) and
SEQ ID NO:3 (TA insertion not present at nucleotides 379-380)

CAGCACTAGTCACCATCACCAAAATCATCCATCAGGGATGAAGGGAAAAACAAAGTGATTTACCTTGAATCAGAA
GATATTCTTCAGCGCGCTTCCCTGGTGGTCCAGTGGCTAAGACCCTATCCTCCCGGTGCAGGGGGCCTCGGTTCA
ATCCCTGGTCGGGGAACTAGATCCCACATGGTGCAACTAAGACCTGGCCCAGCCAAATAAATAAATACATTAAAA
GAAGAAAAGAAGATAGTCTTCAGTCTTCTGAATACTTCACTCTTCTGTCTTCACAGAATACTCTTCAGTCTTGA
AAAGGATGGAAACTCTTACCCTTGCTACAACATGAAGGAAGCTCAAAGACATCATAGTAAGTGAAAGAAGCCAGA
CAC[TA/--]AGGGACGAATGTATGATCCCACTCACAGCGGGTCCTTAGAGTAGTGGAATCCATGGAGACCAAAG
GAGAATGGTGGTTGTCAGGGGCTGGGGGAATGGGATGTGGAGTTGTCTAATGGGGACAATAAAAGGTTTGTGTTG
ATAAAAGGTTTTGGAAATAGTGACGAGTGCACATTATGAATGTCTTTAATGACACTGGGTCCTGGCCTCGCATGG
GTCTCTCAGAACCACCCTCCACCCACTGCGTCCCCCACAGGTGCAGAGGAGGGTCCAGGGCTTGACTGACAATCT
GAATCCGAGTCCGAGGCTCAGTGCTTGGGAAACTGAGGGTGGTGGAGTGCAGAGGGCGAAGGGAAGCAGAGACG
CTCCGCGGTGGGGCCAGCCAGGCTGGACTGAGCTTCACCCCATGGATGCGTCTGGAGTCCCAGCTGCGCCGTGAT
CTGCCCTCTCGCTTTGCCACCCCCGCTCCCGCCCTGCTGCCCTCCCGTCCCTGGGCCTCCGTGGCTCCCCCCA
CCGCAGCGCATCCTCGCCCCCTCTCTAGCAGCCCCCCTCCCGCGGGTTATTAATATCCGGGCCGGGCGCAGGGCC
GCCGCGCATTCCCAGCTGGCAGCCGGGCAGGTGGCGCCGGCGACAGGGCCTGGGCGCGGAACGCGGCTCTCCAG
GCGAGACCGGCGGGCGGGCTCCCCTCCACCACGCGCCCCTGGGAGCCCCCACGTCCTCTGCGCGCCCCTACCGGG
CAGAGCCCTCGGAAAGGTTCCCGTGCCGCGCCGAGTGTTTGGAGACGCTTAGCGACTAAGCGCCGGTCCAGAGCA
CGACCCCAGGGTGCTCGGCGCCCACACCTGACGGCCGGTGACGGAGGTGGGCGCAGGCACTGCGAGGGTGCGGGG
CGGGAGAAGGGGCCGGGATCCTCCCGGGGCGGGGCGCCCTCCCCGCTGGCCCGCACAATCCCCTGCAGGATCGCT
CGGCCACGAAGCCCTCCCAGCGGACCCCCGGGAGATGCGTGGCGCTTCGGAGGGTGGAGAGGGTGAGGTGTGCGC
GGTGGGCTCGGCGGCTGTTTCGCGTCCCTCCCGGGAGGTCCTCCGCCAGGTTCGCGGTAGCCCCTGCGGGAGGGC
TCTGGAACCAGAACCCACTGGGGGCTGCGGCCGCGGAGGGCGCCTCGGCCCGGTAGGAAAGACCCCAGCTCCCCT
CGCCAGACCCAAGGCTGAGCCAAGTCCCACGGGCAGGGGCCTAGGACAGCGTCTCTACACCCAGCTTGCCCTTC
TGCACCGAGTGCTCAGTTGGACGCCCCGAGTTTATCCATGTTAGTGCGAACGCTGTACCTGTAGAGGGAAAAAAC
CGGGAACCAGTTTTATCCGGCCACATTATCCCTAGATGTGGGGAGATTGGGCCATAAAGGGGCCTCTCCTCTCAT
TCAAGTATTCAGGTTTTAGGTCTCTTTTTTCTCATGAGGGTAATTTTCACCCAGTAAGCACGGGTCATGAGTGTG
CAACTCCAGGAGTTTTTACATGTCCGTAGTCGCTAAGTCGTGTCTGACTCTTTGGGACCCCATGGAATGCATAGC
CCGCCAGACTCCTCTGTCCATGGGGAGAATGCTGGAGTGCGTTGCCATGCCCTCCTTCAGGGGATCTTCCCAACC
CAGGGATCAAACCCAGGTCTCCTGCATTGCAGGCGGATTCTTTACCATCTGAGCCACCAGAACACCTGTGTAACC
AGTGCCACATGAGGACATAGCACACGTCCGTCCCGGAGTGCTCTCCGGTGCCCCTACCAGTTGACACCCTCTTC
AACCACTCATAGAGATTTTTTCTTTTCCCCAGCTTCATTCAGGTAAAGGGAATTATACAGTGTGTACTTTTTGTG
TATGGTTTCTGTTTCATCCCCCCCCCCCCCCACTCAACAGAGCATATTTGAGTTTCATCAAGTTGCTGACTGT
TCAATAATTTCATTTTCTTCATCACCTTGGAGCATTTTTATTGGGGGGGGGTGTCAGTTTCTTTATCCATACTA
CTAATCACCAACGTTTGGGTGGTTTCCAGCTTCTGACTGCTATGAACGTTCTCACTCTTGCTTTTTATGGCCATT
TGCACTAATTTTTCTTGGCATAAACCTAAGAGTAGAATTGCTGAATGAGAGGACAGACGTGTGTCCAGCTTTACT
AAGGGTGCCAGATTGTTCGCCACAGGCGGCTGCACTGTTCTTGTCCTCCACTAGCAGTTCAGGAGTTCATTTCCT

FIG. 2A

TCATGTCCTCCCAGCAGTTTTACGAATTTCCTGTTCAAATTTTGTCTTTTTTTCCTTTCAGTTGAGTCATTGCT
CTTTATTGATCTGTAGTTCTTTCACATATTTTGATTACTAGTTCGTTGTCTGATATGTGTCTTCTGATGATCTTT
TCCCAGTCCATGGTTTACATCTTTTACTCTCTCAGTGAAGTTCTTAATTTTCATGAAATCCAATTGGTGGGTCTT
TTACTGCAAGCATTTTTTGCTTTTTTTTTTTTGAAAAATCTTCATTTACCCACAGTCATGCAGATATTCTCCT
GTATTTCTTCCAGAGCTTGATTAATTAATTGATTTAATCTATTACATAAGGTACACAGTCCACCTTGAATTGTTT
TCTTGTGTGGTAGGATATAGGAATCAGGTTTATTTCCCCCATGTGAATAAAGGAAGATTATGAGGGCTTTCCCCT
CTTTAACATATTTTCCTATTTGAACTTTAAAGTCGGCAGATATTACTTTTGCAATCTGAACAAAATGTATTTTCT
TAAAACATACAGGAGAACTATATGGGGAGGAAGACATAGGGGTCAGCCGGGCTTCCCTGCCCTTCAGGGATGAGG
AAGTGAGAAGGCCTAGTGAGAACTCCTGGTTCATCCAGGAGTGAACCATCCTGGTTCATGCCTGCTGTGCTCTGA
TTTTCAGGAAAGGCCATCCAGCTGAGAGGCCTTTGAACTTGCACTGTGGCCCAGGGTGAGAATGCTACTGGGGCA
TGCATGGGGGCAACTGGTCTGGGTGGTACTCTGGTCCCCTGGATAGCTGGGAACTGAAGCAGAGTGTTAGAG
TTCTGCATGGAGAGTCCCCCAGGGGTATCACAGTTGGTGAGCACTGTCCCTCTGCAGGCCTCCCAGCCTGGTGG
GAACTGTGGCCTCTTATGGCCTCTTGGGAGTGGGAAAGGGTGCCTGACCTGCATCTTTAATGAGCATCCTCTCCT
G<u>CAGGACAAGCTTGTTGCCCACAGATGCCCCCTCTCTACCTAAAGGAGCAGCAGGCCCCAGCCCCAAGCCCAGTG</u>
<u>TGAGGTGGCAGAGATGGCACTGAGCCCAGAGCCATCGAGCAGGTTCCTGGTGCCGGCTACAATGGGCAGCGCCAT</u>
<u>GCCCGAGCTGCCTGGTGCCCCCAATGCGTCCCTCAACAGCTCGTTGGCTAGCCCGACGGAGCCCAACTCCCTGGA</u>
<u>AGACCTGGTGGCCACGGGCACCATCGGGGTGGTGCTCTCGGCCATGGGTGTGGTAGGCATGGCAGGCAA[T/C]G</u>
<u>TGTACACGCTGACGGTCATGTGCCGCTTCCTGCACACCTCTGCCTCCATGTACGTCTA[C/T]GTCATCAACCTG</u>
<u>GCGCTGGCAGACCTCCTCTACCTGCTCAGCATCCCCTTCATTGTAGCTACCTACGTCACCAAGAGGTGGCACTT[</u>
<u>T/C]GGCGACGTGGGCTGCCGCGTCCTCTTCAGCCTGGACTTCCTGACCATGCACGCCAGCATCTTCACCCTGAC</u>
<u>CCTCATGAGCAGGGAGCGCTATGCCGCCGTGGTGAGGCCGCTGGACACGGTGCAGCGTTCCAAGGGCTATCGTAA</u>
<u>GGTCCTGGC[G/A]CTGGGCACGTGGCTGCTGGCACTGCTGCTGGCACTGCCCATGATGCTGGCCATCCGGCTGG</u>
<u>TCCGCAGGGGCCACAAGAG[T/C]CTCTGCCTGCC[A/G]GCCTGGGGCCAGCGCACCCACCGCGCCTACCTGAC</u>
<u>GCTGCTCTTCGGGACCAGCATCGTGGGGCCCGGTGTGGTCATCGGGCTGCTCTACGTCCGCCTGGCCCGGGCCTA</u>
<u>CTGGCTGTCGCAGCGGGCCTCCTTCACGCAGACGCGGCGGCTGCCCAACCCCAGGGTGCTCTACCTCATCCTGGG</u>
<u>CATCGTGCTGCTCTTCTGGGCCTGCTTCCTGCCCTTCTGGCTGTGGCAGCTCCTTGCCCAGTACCGTGGGGCCCC</u>
<u>ACCGCTCGCTCCCCGCTCCGCCCGCATCGTCAATTACCTGACCACCTGCCTCACCTATGGCAACAGCTGTGTGAA</u>
<u>CCCCTTCCTCTACACGCTGCTCACCAAGAACTACCGTGACTACCGCCAACGCTC[G/A]CTCCACAGCAGGGGCA</u>
<u>CCAGTGGGCCTGTGGGCGTCCGCAGCTTCCCACAGGGCACACCCGCTGCCAGCTCGGCTCGGGTCGCTCCGTGA</u>
<u>CCTCCAGCAGCCAGCAAGCCACTGAGACCATCGCA[C/T]TGTCCCAGGCGGTCCCCGGGAGTCTCTGCGTCTGA</u>
<u>GCGTCCCCAGCCTCCCTGTGGGCCCTGGGGTAGGCTGTGGGAGTGGCCCCTGGAGCCCAGGTCTCTCCT[G/C</u>
<u>]GACCACCCTCCCCACGGTCTGCCTCCCTTCCCCAGTCCTCTTCCAGAAAGCTCCTGGCTCTCCCTCACCCCTCA</u>
<u>CTCACTTCAGCTCCATCAGTGCAGCTACTTTCCTCATAACGCCAAGAAGTGCCCCCAACCCAGTCCATCTGTGAG</u>
<u>GGTCTGCAGGAGGCTC[A/G]GGCTCAGGGCCAGCTCCTGAAGACCGTGGTGAGTGGAGTCTTCACCAGCCCCCT</u>
<u>GCAGA[C/T]GTGACTGCGTACCTGACGCAC[G/A]ACAGG[G/A]TACACCGTGGCAGGTGACACCATGTTGCC</u>
<u>ACACAAGCTGCCTGTGTGGGACCCT</u>CCTCCTGGCATGAGCGTGGCCCCAGTGGCACCCATTTCTCCCAACTGCCA
TGTGGTTCCATCCCGCACAGCTTCAGCACCTGGAACAATAAACGCTGAGCTCCCTGAGTCTTGTCTGCAACAGCA
GTGTGAGTGGGGTGTCAAAGGAGGCAGGACCCCAGGACGTCCTCCTGCACTTGGAGGAGCCCATCTGCCTGACC
GGGCAGGGACATGTCTGGCCATTAGGCCTTCCTGACATGGTGGGTGGGTGCCATCTGGCCTGAGCCAGGCCCTG
GGTGTGGGGCCTGAGACCCTGGGGTGAGTGAGGCGGGGAGCCACCAGCCTCAACCTGCTCAGGG

FIG. 2B

A
Cattle: CO872879/AAFC03010889.1
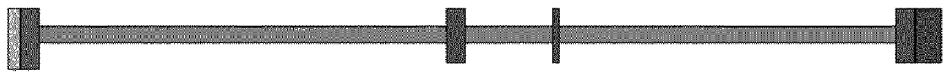

US 7,955,803 B2

UROTENSIN 2 AND ITS RECEPTOR AS CANDIDATE GENES FOR BEEF MARBLING SCORE, RIBEYE AREA AND FATTY ACID COMPOSITION

INCORPORATION BY REFERENCE

This application claims benefit of U.S. provisional patent application Ser. No. 60/910,180 filed Apr. 4, 2007.

The foregoing applications, and all documents cited therein or during their prosecution ("appln cited documents") and all documents cited or referenced in the appln cited documents, and all documents cited or referenced herein ("herein cited documents"), together with any manufacturer's instructions, descriptions, product specifications, and product sheets for any products mentioned herein or in any document incorporated by reference herein, are hereby incorporated herein by reference, and may be employed in the practice of the invention.

FEDERAL FUNDING LEGEND

This invention was supported, in part, using federal funds from the National Institutes of Health. Accordingly, the Federal Government may have certain rights in this invention.

FIELD OF THE INVENTION

The present invention relates to methods and systems of identification and management of beef cattle for production of healthy, yet flavorful product. More specifically, the invention relates to methods and systems relating to identification of single nucleotide polymorphisms (SNPs) and haplotypes associated with beef marbling score, ribeye area, amounts of saturated and monounsaturated fatty acids, and $\Delta^9$ desaturase activity $R_2$=16:1 to 16:0. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Urotensin II (UTS2) encodes a 11 amino acid mature peptide that binds to the orphan G protein-coupled receptor, GPR-14 (renamed urotensin 2 receptor, UTS2R) [Ames et al., 1999, *Nature* 401: 282-286]. Recent studies have indicated that both UTS2 and/or UTS2R have significant impacts on insulin resistance [Langham et al., 2004, *Am J Kidney Dis.* 44: 826-831; Suzuki et al., 2004, Peptides 25: 1803-1808 and Ong et al., 2006, *Peptides* 27: 1659-1667], which represents a core pathological character of patients with type 2 diabetes mellitus and obesity. For example, in Hong Kong Chinese, the GGT haplotype (-605G, 143G and 3836T) in the UTS2 gene is associated with higher plasma level of urotensin 2 and insulin, and higher homeostasis model assessment of insulin resistance index and beta-cell function, while the AC haplotype (-1640A and -8515C) in the UTS2R gene has a higher amount of plasma glucose 2 h after a 75 g oral glucose load [Ong et al. Peptides. 2006; 27(7):1659-67]. In human diabetic tissue, Langham and colleagues [Am J Kidney Dis. 2004; 44(5):826-3 1] found that expression of both UTS2 and UTS2R are increased 45- and almost 2,000-fold in comparison to control nephrectomy tissue, respectively (P<0.0001) using quantitative real-time polymerase chain reaction. In the healthy rat, infusion of synthetic rat urotensin 2 inhibits both insulin release induced by glucose and insulin responses induced by carbachol, glucagon-like peptide-1, and a calcium channel agonist [Silvestre et al. Eur J Endocrinol. 2004; 151 (6):803-9]. However, in streptozotocin-induced diabetic rats, long-term treatment with palosuran, a UTS2R antagonist, improved survival, increased insulin, and slowed the increase in glycemia, glycosylated hemoglobin, and serum lipids [Clozel et al. J Pharmacol Exp Ther. 2006; 316(3): 1115-21]. Therefore, the urotensin 2 system plays a unique role both in insulin secretion and in the renal complications of diabetes.

Studies have shown that the fat droplets accumulated in human skeletal muscle are a major contributor to insulin resistance [Goodpaster & Wolf, Pediatr Diabetes. 2004; 5(4): 219-26]. For example, in male Pima Indians, negative relationships were found between amounts of triglyceride in skeletal muscle and physiological and supraphysiological insulin levels, and nonoxidative glucose disposal (r=−0.44−−0.53, P<0.01) [Pan et al. Diabetes. 1997; 46:983-8]. In a European population, muscle lipid was correlated with percent body fat (r=0.50, p=0.028), waist:hip ratio (r=0.74, p<0.001), visceral fat (r=0.62, p=0.004) and insulin sensitivity (r=−0.53, p=0.016) [Forouhi et al. Diabetologia. 1999; 42(8):932-5]. In beef cattle, fat accumulation in muscle is usually measured as marbling, which describes the appearance of white flecks or streaks of fat between the muscle fibers. Therefore, the objective of the present study was to determine whether both UTS2 and UTS2R genes contribute to carcass, fat deposition and fatty acid composition in beef cattle.

There is a need for methods that allow relatively easy and more efficient selection and breeding of farm animals that have an advantage for an inheritable trait of beef marbling score (BMS), ribeye area (REA), amounts of saturated (rSFA), monounsaturated (rMUFA) and polyunsaturated fatty acids (rPUFA), $\Delta^9$ desaturase activities ($R_1$=14:1 to 14:0; $R_2$=16:1 to 16:0; $R_3$=18:1 to 18:0), conjugated linoleic acid (CLA) and cholesterol (CHOL) . The economic significance of the use of genetic markers that are associated with specific economically important traits (especially carcarss and meat quality traits that are hard to measure) in livestock through marker-assisted selection cannot therefore be overemphasized.

Citation or identification of any document in this application is not an admission that such document is available as prior art to the present invention.

SUMMARY OF THE INVENTION

The present invention relates to associations between SNPs of urotensin II (UTS2) and urotensin 2 receptor (UTS2R) with beef marbling score (BMS), ribeye area (REA), amounts of saturated (rSFA) and monounsaturated (rMUFA), and $\Delta^9$ desaturase activity $R_2$=16:1 to 16:0.

The application is based, in part, on Applicants' discovery that UTS2 gene was significantly associated with the amount of skeletal saturated fatty acids, while its receptor (UTS2R) gene had significant effects on amounts of saturated and monounsaturated fatty acids, $\Delta^9$ desaturase activity for converting 16:1 into 16:0, beef marbling score and ribeye area.

The invention encompasses a method for sub-grouping animals according to genotype wherein the animals of each sub-group have similar polymorphisms in UTS2 and/or UTS2R genes that may comprise determining the genotype of each animal to be sub-grouped by determining the presence of single nucleotide polymorphisms in the UTS2 and/or UTS2R genes, and segregating individual animals into sub-groups wherein each animal in a sub-group has similar polymorphisms in the UTS2 and/or UTS2R genes.

The invention also encompasses a method for sub-grouping animals according to genotype wherein the animals of each sub-group have a similar genotype in the UTS2 and/or UTS2R genes that may comprise determining the genotype of each animal to be sub-grouped by determining the presence of single nucleotide polymorphism(s) of interest in the UTS2 and/or UTS2R genes, and segregating individual animals into sub-groups depending on whether the animals have, or do not have, the single nucleotide polymorphism(s) of interest in the UTS2 and/or UTS2R genes.

The single nucleotide polymorphism(s) of interest may be selected from the group consisting of the follow: three SNPs in the promoter and two SNPs in intron 2 of the UTS2 gene: AAFC03010889.1:g.9408A>C, g.9552C>A, g.9628G>A, g.13294G>A and g.13900A>C, respectively, one insertion/deletion (INDEL) with two nucleotides of TA (AAFC03013715.1:g.2935-36TA>--) in the promoter region and 13 SNPs in the coding and 3'UTR regions of the bovine UTS2R gene, including AAFC03013715.1:c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively.

The invention further relates to a method for sub-grouping animals according to genotype wherein the animals of each sub-group have similar haplotypes in the UTS2 and/or UTS2R genes that may comprise determining the genotype of each animal to be sub-grouped by determining the presence of any of the above SNPs, and segregating individual animals into sub-groups depending on whether the animals have, or do not have, any of the above SNPs in the UTS2 and/or UTS2R genes.

The invention also relates to method for identifying an animal having a desirable phenotype as compared to the general population of animals of that species, which may comprise determining the presence of single nucleotide polymorphisms in the UTS2 and/or UTS2R genes of the animal, wherein the presence of the SNP's are indicative of a desirable phenotype.

In an advantageous embodiment, the animal may be a bovine. In another advantageous embodiment, the UTS2 and/or UTS2R genes may be bovine UTS2 and/or UTS2R genes.

The invention also encompasses computer-assisted methods and systems for improving the production efficiency for livestock having marketable beef marbling score (BMS), ribeye area (REA), amounts of saturated (rSFA) and monounsaturated (rMUFA), and $\Delta^9$ desaturase activity $R_2$=16:1 to 16:0 using multiple data, and in particular the genotype of the animals as it relates to UTS2 and/or UTS2R SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes and haplotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within the UTS2 and/or UTS2R genes related to feed intake and feed efficiency and associating those data with other data about the animal or its herd, and maintaining those data in ways that are accessible. Another aspect of the invention encompasses a computer-assisted method for predicting which livestock animals possess a biological difference in beef marbling score (BMS), ribeye area (REA), amounts of saturated (rSFA) and monounsaturated (rMUFA), and $\Delta^9$ desaturase activity $R_2$=16:1 to 16:0., and which may include the steps of using a computer system, e.g., a programmed computer comprising a processor, a data storage system, an input device and an output device, the steps of: (a) inputting into the programmed computer through the input device data that includes a genotype of an animal as it relates to any one of the UTS2 and/or UTS2R SNPs described herein, (b) correlating feed intake and feed efficiency predicted by the UTS2 and/or UTS2R genotypes using the processor and the data storage system and (c) outputting to the output device the feed intake and feed efficiency correlated to the UTS2 and/or UTS2R genotypes, thereby predicting which livestock animals possess improved beef marbling score (BMS), ribeye area (REA), amounts of saturated (rSFA) and monounsaturated (rMUFA), and $\Delta^9$ desaturase activity $R_2$=16:1 to 16:0.

Yet another aspect of the invention relates to a method of doing business for managing livestock comprising providing to a user a computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein such physical characteristics as feed intake, feed efficiencies, and growth genotypes are associated with the RFI genotype and haplotypes.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which:

FIGS. 1A-1C depict a genomic DNA sequence of the bovine UTS2 gene (SEQ ID NO:1, derived from AAFC03010889.1). Expressed sequences are underlined with exon-intron boundaries in bold. Single nucleotide polymorphisms are listed in brackets and bold underlined.

FIGS. 2A-2B depict a genomic DNA sequence of the bovine UTS2R gene (SEQ ID NO:2-TA insertion present at nucleotides 389-90; SEQ ID NO:3-TA insertion not present at nucleotides 389-390, derived from AAFC03013715.1(SEQ ID NO:28)). Expressed sequences are underlined. Mutations are listed in brackets and bold underlined.

FIGS. 3A and 3B depict genomic organizations of UTS2 (A) and UTS2R (B) between cattle and human.

DETAILED DESCRIPTION

Figure 4:
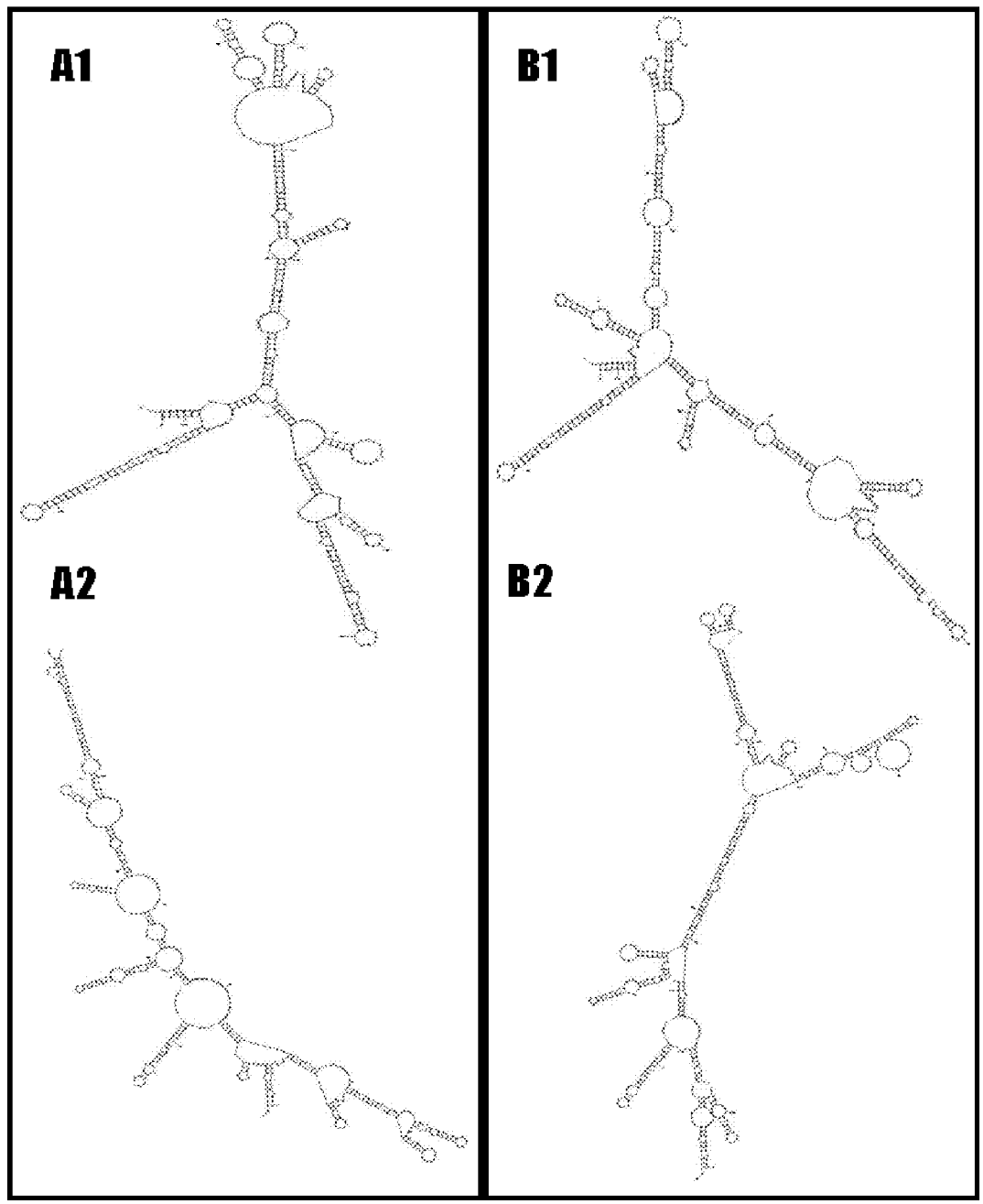
FIG. 4 depicts UTS2R mRNA local secondary structures between haplotype TCTGTAGCGACGG (SEQ ID NO:4) and haplotype CTCACGATCGTAA (SEQ ID NO:5) based on two-segment analysis (A1 vs. B1 and A2 vs. B2).

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("lnRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940;

6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/ oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as Thermus aquaticus. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product. "Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003;3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number (s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene(s) of interest is a bovine UTS2 and/or a UTS2R gene, the bovine UTS2 and/or UTS2R nucleotide sequences can be selected from, but is not limited to, GenBank Accession Nos. AAFC03010889.1 and AAFC03013715.1, herein incorporated by reference, (SEQ ID NO:28). In an advantageous embodiment, the gene(s) of interest include, but are not limited to, the sequences corresponding to three SNPs in the promoter and two SNPs in intron 2 of the UTS2 gene: AAFC03010889.1:g.9408A>C, g.9552C>A, g.9628G>A, g.13294G>A and g.13900A>C, respectively; the bovine UTS2R, one insertion/deletion (INDEL) with two nucleotides of TA (AAFC03013715.1 (SEQ ID NO:28):g.2935-36TA>--) in the promoter region and 13 SNPs in the coding and 3'UTR regions of the gene, including AAFC03013715.1 (SEQ ID NO:28):c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively, or fragments thereof or a region of the bovine genome that comprises said sequence(s).

The present invention, therefore, provides isolated nucleic acids that may specifically hybridize to the nucleotide sequence corresponding to three SNPs in the promoter and two SNPs in intron 2 of the UTS2 gene: AAFC03010889.1: g.9408A>C, g.9552C>A, g.9628G>A, g.13294G>A and g.13900A>C, respectively, one insertion/deletion (INDEL) with two nucleotides of TA (AAFC03013715.1 (SEQ ID NO:28):g.2935-36TA>--) in the promoter region and 13 SNPs in the coding and 3'UTR regions of the bovine UTS2R gene, including AAFC03013715.1 (SEQ ID NO:28): c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively.

The single nucleotide polymorphism(s) of interest may be selected from the group comprising the nucleotide substitutions defined in three SNPs in the promoter and two SNPs in intron 2 of the UTS2 gene: AAFC03010889.1:g.9408A>C, g.9552C>A, g.9628G>A, g.13294G>A and g.13900A>C, respectively, one insertion/deletion (INDEL) with two nucleotides of TA (AAFC03013715.1 (SEQ ID NO:28):g.2935-36TA>--) in the promoter region and 13 SNPs in the coding and 3'UTR regions of the bovine UTS2R gene, including AAFC03013715.1 (SEQ ID NO:28):c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively.

The SNPs advantageous in the present invention are associated with certain economically valuable and heritable traits relating to meat quality in bovines. Therefore, it is an object of the present invention to determine the genotype of a given animal of interest as defined by the nucleotide substitutions selecting from the group consisting of three SNPs in the promoter and two SNPs in intron 2 of the UTS2 gene: AAFC03010889.1:g.9408A>C, g.9552C>A, g.9628G>A, g.13294G>A and g.13900A>C, respectively, one insertion/ deletion (INDEL) with two nucleotides of TA (AAFC03013715.1 (SEQ ID NO:28):g.2935-36TA>--) in the promoter region and 13 SNPs in the coding and 3'UTR regions of the bovine UTS2R gene, including AAFC03013715.1 (SEQ ID NO:28):c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively, according to the present invention. It is also contemplated that the genotype of the animal(s) may be defined by additional SNPs within the UTS2 and/or UTS2R genes or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly with SNPs located within the UTS2 and/or UTS2R genes. The methods further allow, by computer-assisted methods of the invention, to correlate SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the UTS2 and/or UTS2R genes, advantageously of the region encompassing an UTS2 and/or UTS2R SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with an UTS2 and/or UTS2R gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}$=8; $N_{dif}$=2). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics TM Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in an UTS2 and/or UTS2R gene which are unique to an UTS2 and/or UTS2R gene. As to PCR or hybridization primers or probes and optimal lengths therefore, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e. g., $^3H$, $^{125}I$, $^{35}S$, $^{14}C$, $^{32}P$, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g , $^{3}H$, $^{125}I$, $^{35}S$, $^{14}C$, $^{32}P$, etc.), enzymes (e.g. horseradish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Georgia) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for desirable alleles of the UTS2 and/or UTS2R gene polymorphic sites associated with desirable beef marbling score (BMS), ribeye area (REA), amounts of saturated (rSFA) and monounsaturated (rMUFA), and $\Delta^9$ desaturase activity $R_2=16:1$ to 16:0., would lead to a breed, line, or population having higher numbers of offspring with desirable beef marbling score (BMS), ribeye area (REA), amounts of saturated (rSFA) and monounsaturated (rMUFA), and $\Delta^9$ desaturase activity $R_2=16:1$ to 16:0. Thus, the UTS2 and/or UTS2R SNPs of the present invention can be used as a selection tool.

Desirable phenotypes may also include, but are not limited to, feed intake, growth rate, body weight, carcass merit and composition, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF%, %), marbling score (MBS, 10 to 99), marbling score divided by days on feed (MBS/DOF), quality grade, less than or equal to select versus greater than or equal to choice (QG, <Se vs, >Ch), ribeye area (REA, $in^2$), ribeye area per hundred weight HCW (REA/cwt HCW, $in^2$/100 lb hot carcass weight (HCW) and subcutaneous fat depth (SFD).

One aspect of the present invention provides for grouping animals and methods for managing livestock production comprising grouping livestock animals such as cattle according the genotype as defined by panels of SNPs, each panel comprising at least one SNP, one or more of which are in the UTS2 and/or UTS2R genes of the present invention. Other SNPs that may be included in panels of SNPs include, but not limited to, SNPs found in the calpastatin gene, CRH gene, FGF8 gene, GHR gene, TFAM gene, GHR gene, FABP4 gene, ghrelin gene, leptin gene, NPY gene, ob gene, UASMS1 gene, UASMS2 gene, UASMS3 gene, UCN gene, UCP2 gene and/or the UQCRC1 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, feed intake, carcass/meat quality and milk production. The present invention provides methods of screening livestock to determine those more likely to develop a desired body condition by identifying the presence or absence of one or more gene polymorphisms correlated with meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or subgrouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), bovine spongiform encephalopathy (BSE) diagnosis, brucellosis vaccination, FMD (foot and mouth disease) vaccination, BVD (bovine viral diarrhea) vaccination, Sure Health pre-conditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are UTS2 and/or UTS2R sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the UTS2 and/or UTS2R sequences described herein.

Another embodiment of the invention is an oligonucleotide that specifically hybridizes under high stringency conditions to any one of the polymorphic sites of the UTS2 and/or UTS2R genes, wherein the oligonucleotide is between about 18 nucleotides and about 50 nucleotides.

In another embodiment of the invention, the oligonucleotide comprises a central nucleotide specifically hybridizing with a UTS2 and/or UTS2R genes polymorphic site of the portion of the nucleic acid molecule.

Another aspect of the invention is a method of identifying a UTS2 and/or UTS2R polymorphisms in a nucleic acid sample comprising isolating a nucleic acid molecule encoding UTS2 and/or UTS2R genes or a fragment thereof and determining the nucleotide at the polymorphic site.

Another aspect of the invention is a method of screening cattle to determine those bovines more likely to exhibit a biological difference in meat quality comprising the steps of obtaining a sample of genetic material from a bovine; and assaying for the presence of a genotype in the bovine which is associated with meat quality, the genotype characterized by polymorphisms in the UTS2 and/or UTS2R genes.

In other embodiments of this aspect of the invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the UTS2 and/or UTS2R gene or a portion thereof that contains the polymorphism. In other embodiments of the invention, the amplification may include the step of selecting a forward and a reverse sequence primer capable of amplifying a region of the UTS2 and/or UTS2R gene.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising an UTS2 and/or UTS2R genotype of an animal, (b) correlating growth, feed intake, efficiency or carcass merit quality predicted by the UTS2 and/or UTS2R genotype using the processor and the data storage system and (c) outputting to the output device the meat quality correlated to the UTS2 and/or UTS2R genotype, thereby predicting which livestock animals possess a particular growth level, feed intake, efficiency or carcass merit quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

Urotensin 2 and its Receptor as Candidate Genes for Beef Marbling Score, Ribeye Area and Fatty Acid Composition Several reports have shown that urotensin 2 (UTS2) and its receptor (UTS2R) are involved in glucose metabolism and insulin resistance, which lead to development of type 2 diabetes mellitus (T2DM) in humans. In the present study, both bovine UTS2 and UTS2R genes were annotated and 5 single nucleotide polymorphisms (SNPs) were identified for the former gene and 14 mutations for the latter gene. Four mutations were genotyped on a Wagyu x Limousin reference population, including 6 $F_1$ bulls, 113 $F_1$ dams and ~250 $F_2$ progeny. Among 12 phenotypes related to fat deposition and fatty acid composition, it was observed that the UTS2 gene was significantly associated with the amount of skeletal saturated fatty acids, while its receptor (UTS2R) gene had significant effects on amounts of saturated and monounsaturated fatty acids, $\Delta^9$ desaturase activity for converting 16:1 into 16:0, beef marbling score and ribeye area. However, in this population, these markers were not associated with subcutaneous fat depth or percent kidney, pelvic and heart fat. It was also found that mutations in the promoter regions altered the promoter activities in both genes and coding SNPs might affect the mRNA stability in the UTS2R gene. Overall, the present study provides the first evidence that both UTS2 and UTS2R genes regulate skeletal muscle fat accumulation and metabolism, thus contributing to insulin resistance in obesity and T2DM in humans.

Three members of the urotensin II family of peptides have been discovered in mammals, including urotensin 2 (UTS2), urotensin 2 receptor (UTS2R) and urotensin 2 domain containing (UTS2D). UTS2 is cyclic peptide with an 11 amino acid mature peptide in human, but it has been recognized as a hormone in the neurosecretory system of teleost fish for over 30 years [1]. In addition, UTS2 is a potent vasoconstrictive peptide that regulates both endothelium-dependent and independent vasodilatation [2]. The human orphan G protein-coupled receptor 14 (GPR14) was cloned in 1995 [3] and then confirmed to function as the UTS2 receptor (UTS2R) [4]. Interestingly, the UTS2R shares highest identity with the somatostatin receptor SSTR4 [3]. A novel urotensin II-related peptide, now named the urotensin 2 domain containing (UTS2D) were also isolated in human, mouse and rat [5]. UTS2D binds and activates the urotensin 2 receptor, suggesting that it is the endogenous and functional ligand for UTS2R.

Among these three genes, both UTS2 and UTS2R have been reported to affect glucose metabolism and insulin resistance, a core pathological characteristic of patients with type 2 diabetes mellitus (T2DM). In Hong Kong Chinese, the GGT haplotype (-605G, 143G and 3836T) in the UTS2 gene is associated with higher plasma level of urotensin 2 and insulin, and higher homeostasis model assessment of insulin resistance index and beta-cell function, while the AC haplotype (-1640A and -8515C) in the UTS2R gene has a higher amount of plasma glucose 2 h after a 75 g oral glucose load [6]. In human diabetic tissue, Langham and colleagues [7] found that expression of both UTS2 and UTS2R are increased 45- and almost 2,000-fold in comparison to control nephrectomy tissue, respectively (P<0.0001) using quantitative real-time polymerase chain reaction. In the healthy rat, infusion of synthetic rat urotensin 2 inhibits both insulin release induced by glucose and insulin responses induced by carbachol, glucagon-like peptide-1, and a calcium channel agonist [8]. However, in streptozotocin-induced diabetic rats, long-term treatment with palosuran, a UTS2R antagonist, improved survival, increased insulin, and slowed the increase in glycemia, glycosylated hemoglobin, and serum lipids [9]. Therefore, the urotensin 2 system plays a unique role both in insulin secretion and in the renal complications of diabetes.

Studies have shown that the fat droplets accumulated in human skeletal muscle are a major contributor to insulin resistance [10]. For example, in male Pima Indians, negative relationships were found between amounts of triglyceride in skeletal muscle and physiological and supraphysiological insulin levels, and nonoxidative glucose disposal (r=-0.44--0.53, P<0.01) [11]. In a European population, muscle lipid was correlated with percent body fat (r=0.50, p=0.028), waist:hip ratio (r=0.74, p<0.001), visceral fat (r=0.62, p=0.004) and insulin sensitivity (r=-0.53, p=0.016) [12]. Therefore, the objective of the present study was to determine whether both UTS2 and UTS2R genes contribute to carcass, fat deposition and fatty acid composition in beef cattle.

Animals, body fat deposition and fatty acid composition. A Wagyu-Limousin $F_2$ reference population was used in the present study, including 6 $F_1$ bulls, 113 $F_1$ dams and ~250 $F_2$ progeny. The entire core of the longissimus dorsi was sampled from these $F_2$ progeny and relative amounts of saturated (rSFA), monounsaturated (rMUFA) and polyunsaturated fatty acids (rPUFA), three indexes of $\Delta^9$ desaturase activity ($R_1$=14:1 to 14:0; $R_2$=16:1 to 16:0; $R_3$=18:1 to 18:0), conjugated linoleic acid mg/100 g dry meat (CLA), cholesterol mg/100 g dry meat (CHOL), ribeye area (REA in in$^2$) and beef marbling score (BMS) were measured. In addition, subcutaneous fat depth (SFD) and percent kidney-pelvic-heart fat (KPH) were also recorded in the population. BMS was determined at the interface of the 12th and 13th ribs and was evaluated by subjective comparison of the amount of fat within the longissimus muscle with photographic standards (*National Livestock and, Meat Board* 1981 ). SFD was recorded at the 12th rib at a point three-fourths the width of the longissimus muscle from its chine bone end. The amount of KPH was estimated and recorded as a percentage of carcass weight. Development/management of the Wagyu-Limousin reference population and measurement/definition of these phenotypes were described previously [13, 14].

Gene, mutation, genotyping and association. Both cDNA and genomic DNA sequences of the bovine UTS2 and UTS2R were retrieved from the GenBank databases using a comparative approach, as previously described [15]. Alignment between cDNA and genomic DNA sequences was used to determine genomic organization for each of these two genes. A total of 11 pairs of primers (Table 1) was designed based on the genomic DNA sequences and used to screen genetic polymorphisms in the promoter, coding and untranslated regions of both bovine UTS2 and UTS2R genes (FIG. 1 and FIG. 2). Approximately 50 ng of genomic DNA each from six Wagyu x Limousin $F_1$ bulls was amplified in a final volume of 10 μl that contained 12.5 ng of each primer, 150 μM dNTPs, 1.5 mM MgCl$_2$, 50 mM KCl, 20 mM Tris-HCl and 0.25U of Platinum Taq polymerase (Invitrogen, Carlsbad, Calif.). The following PCR conditions were used: 94° C. for 2 min, 35 cycles of 94° C. for 30 sec, 60° C. for 30 sec and 72° C. for 30 sec, followed by a final 5 min extension at 72° C. PCR products were then sequenced on ABI 3730 sequencer in the Laboratory for Biotechnology and Bioanalysis (Washington State University) using a standard protocol and polymorphisms were detected.

TABLE 1

Primers designed for mutation detection in the bovine UTS2 and UTS2R genes.

| Target region | Primer sequences (5'-3') | Size in bp | Tm |
|---|---|---|---|
| UTS2 | | | |
| Promoter | Forward: GCCTTGAGATTGAATTTTTGCTGTG<br>Reverse: AAATTTACTGTCTTGTTGCCTAGTG | 676 | 61° C. |
| Exon (relic) | Forward: TTTTGTACACTAGGCAACAAGACAG | 540 | 61° C. |

TABLE 1-continued

Primers designed for mutation detection in the bovine UTS2 and UTS2R genes.

| Target region | Primer sequences (5'-3') | Size in bp | Tm |
|---|---|---|---|
| | Reverse: TGAGACATGCCTTAAGAATCCTCAGA | | |
| Exon 1 | Forward: GGGATGATATGAGGTCATAGGATAAT | 409 | 57° C. |
| | Reverse: TCTGAGACATGCCTTAAGAATCC | | |
| Exon 2 | Forward: CTCCTCCAGGGGATCTTCTCAAC | 506 | 61° C. |
| | Reverse: TAATGCTCTTCTTCCCTCCCCTTG | | |
| Exon 3 | Forward: TTTGTGAACTCTGGGGGCTAGAAA | 557 | 61° C. |
| | Reverse: GGTCCTTGGACCCAGTGAAGATAA | | |
| Exon 4 | Forward: ATCCCATGAAACAGCAAGAAAACC | 404 | 61° C. |
| | Reverse: CAACCACTCATAGTATCTGCAAAACA | | |
| UTS2R | | | |
| Promoter | Forward: AGTCACCATCACCAAAATCATCCA | 676 | 61° C. |
| | Reverse: CGGACTCGGATTCAGATTGTCAGT | | |
| Exon 1A | Forward: GAGAGGCCTTTGAACTTGCACTGT | 631 | 61° C. |
| | Reverse: TAGACGTACATGGAGGCAGAGGTG | | |
| Exon 1B | Forward: GGCATGGCAGGCAATGTGTA | 599 | 61° C. |
| | Reverse: ATGCCCAGGATGAGGTAGAGCAC | | |
| Exon 1C | Forward: GTGGTCATCGGGCTGCTCTAC | 531 | 61° C. |
| | Reverse: CCACTCCCCACAGCCTACCC | | |
| Exon 1D | Forward: CAGCCAGCAAGCCACTGAGAC | 601 | 61° C. |
| | Reverse: GGGTCCTGCCTCCTTTGACAC | | |

A total of 5 mutations were identified in UTS2 and 14 in UTS2R gene, respectively. Two SNPs (single nucleotide polymorphisms), one in the promoter and one in intron 2 of UTS2 and two mutations, one INDEL (insertion/deletion) in the promoter and one coding SNP of UTS2R were selected for genotyping on a Sequenom iPLEX assay using services provided by the Children's Hospital Oakland Research Institute, Oakland, Calif. The phenotypic data for all measurements described above were analyzed in a fixed effects model that included the effects of year, gender, age at harvest (linear) and the genotype for each marker using the GLM (general linear model) procedure of SAS v9.1 (SAS Institute Inc., Gary, N.C.). Pair-wise comparisons of least squares means were performed using a protected t-test.

Promoter activity assay. Among the genetic polymorphisms discovered above, three SNPs were located in the promoter region of UTS2 and one insertion/deletion in the promoter of UTS2R gene, respectively. The effects of these mutations on promoter activities were then examined using a Dual-Luciferase Report Assay System (Promega, Madison, Wis.). The forward and reverse gene-specific primers that were used to amplify the promoter regions (Table 1) were then engineered with a 5' BglII and 3' HindIII site plus a 5' tail of CTTC, respectively, for directional cloning into the BglII/HindIII site of pGL3-basic (Premega, Madison, Wis.). Two types of haplotypes at three polymorphic sites in the UTS2 promoter: A-C-A and C-A-G; and two types of INDELs in the UTS2R promoter: TA insertion and TA deletion were prepared for the promoter constructs. The human lung carcinoma H1299 cells were transfected with each of the recombinant pGL3 plasmids containing the constructs described above. pRL-CMV plasmid was also co-transfected into H1299 cells as a transfection control. The human cells were collected 28 hours post-transfection and firefly luciferase and Renilla luciferase activities were measured with the Dual Luciferase Reporter Assay system according to the manufacturer's protocol. Light emission was quantified with a Multilabel Counter (Wallace 1420 Victor 2, Turku, Finland). Triplicate data were collected from three independent experiments. The ratios of firefly luciferase activity to Renilla luciferase activity were calculated and used to compare the differences in activity between two constructs for each gene.

Annotation of the bovine UTS2 and UTS2R genes. The cDNA sequences of human UTS2 (NM_021995, transcript variant 1) and UTS2R (NM_018949) genes were used in BLAST searches against GenBank "nr" database, thus retrieving orthologous cDNA sequences for both bovine genes (CO872879 for UTS2 and BT021614 for UTS2R). BLAST searches using the bovine cDNA sequences as references then obtained their genomic DNA sequences (AAFC03010889 for UTS2 and AAFC03013715 for UTS2R) from the bovine genome sequencing database (Build 3. 1). For the bovine UTS2 gene, alignment between the cDNA and the genomic DNA sequences revealed that it consists of four exons only, which correspond to the transcript variant 2 of the human ortholog (NM_006786) (FIG. 3A). However, alignment between the human transcript variant 1 (NM_021995) and the same bovine genomic DNA contig detected a relic for exon 1 of the variant, but it seems that its expression in cattle is totally destroyed by an unusual intron splicing site of CT instead of GT (see AAFC03010889.1: g.9800C). In fact, GenBank databases show that the UTS2 variant 1 does not exist in mouse either (NM_011910) and rat (NM_019160). The UTS2R is an intronless gene in mammals, including cattle (FIG. 3B).

Genetic polymorphisms. Direct sequencing of PCR products on 6 $F_1$ bulls identified three SNPs in the promoter and two SNPs in intron 2 of the UTS2 gene: AAFC03010889.1:

g.9408A>C, g.9552C>A, g.9628G>A, g.13294G>A and g.13900A>C, respectively. For the bovine UTS2R, one insertion/deletion (INDEL) with two nucleotides of TA (AAFC03013715.1 (SEQ ID NO:28):g.2935-36TA>--) was detected in the promoter region, while 13 SNPs were identified in the coding and 3'UTR regions of the gene, including AAFC03013715.1 (SEQ ID NO:28):c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively. Although the first eight SNPs in the bovine UTS2R gene are coding SNPs, none are missense mutations. However, the Mfold web server [16] predicted that these 13 SNPs do cause mRNA secondary structure changes in the bovine gene (FIG. 4).

Associations of UTS2 and UTS2R with body fat deposition. AAFC03010889.1: g.9628G>A and g.13900A>C in the bovine UTS2 gene and AAFC03013715.1 (SEQ ID NO:28) :g.2935-36TA>-- and c.6506C>T in the bovine UTS2R gene were chosen for genotyping on a Sequenom iPLEX assay. As two SNPs in the former genes had no combination in these $F_2$ progeny by forming two haplotypes AA and CG, only three markers were used in the association analysis. The phenotypes that had at least one suggestive (P=0.05–0.06) or significant (P<0.05) association are listed in Table 2. The UTS2 gene had a significant effect on one trait only, i.e., the relative amount of saturated fatty acids. In particular, animals with GG genotypes had 1.39 units (P=0.0365) less rSFA than animals with AA genotypes. For the bovine UTS2R gene, the promoter INDEL polymorphism was significantly associated with rMUFA (P=0.0452), $R_2$ (P=0.0177) and REA (P=0.0488) (Table 2). The homozygous animals with the insertion allele (TA/TA) had a 1.65 units higher rMUFA, but 10.52% lower $R_2$ activity and 0.56 in$^2$ smaller LD muscle area than the homozygous animals with TA deleted (Table 2). The coding SNP in the bovine UTS2R gene had significant impacts on both rSFA and rMUFA, plus a suggestive effect on BMS (Table 2). The TT animals had an additional 0.64 units of marbling and 1.82 units of rMUFA, but 1.75 less units of rSFA than the CC animals.

Figure 5:
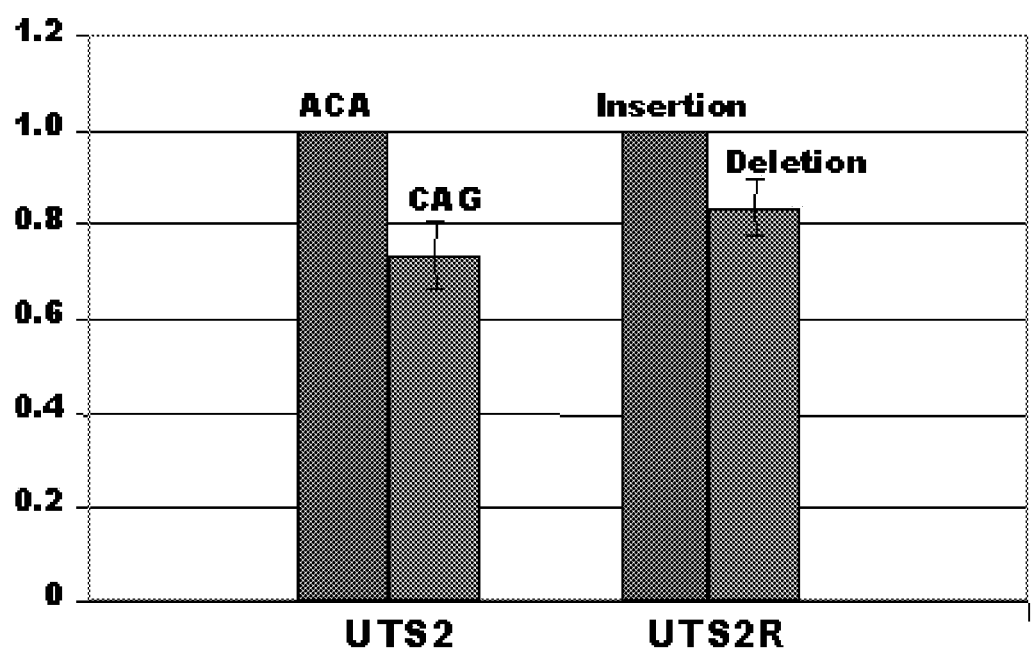
FIG. 5 depicts effects of mutations on promoter activity in the H1299 cells.

Mutations and promoter activities. As indicated above, two types of haplotypes at three polymorphic sites in the UTS2 promoter: A-C-A and C-A-G; and two types of INDELs in the UTS2R promoter: TA insertion and TA deletion were prepared for the promoter constructs to investigate how these mutations affect promoter activities of these two genes. In the UTS2 promoter, the C-A-G construct produced less promoter activities than the A-C-A construct by 27% in the H1299 cells (FIG. 5). In the UTS2R promoter, the deletion allele yielded lower promoter activities than the insertion constructs by 16% in the same cell lines (FIG. 5). A search for transcription binding sites using MatInspector [17] indicated AAFC03010889.1:g.9408A in the UTS2 promoter gained a site for FAST-1 SMAD interacting proteins, while AAFC03010889.1:g.9408C gained a site for neuron-specific-olfactory factor. At the g.9552C>A polymorphic site, the former allele had a transcription binding site for AP4 and related proteins only, while the latter allele possessed one site for MAF/AP 1 related factors and one site for octamer binding protein. There were a total of four binding sites for MAF and AP1 related factors, TCF11 transcription factor, TALE homeodomain class recognizing TG motifs and MYT1 C2HC zinc finger protein when an A allele is located at position AAFC03010889.1:g.9628. When the g.9628A is substituted by g.9628G, only one site was created for activator/repressor binding to transcription initiation site. Overall, the A-C-A haplotype in the UTS2 promoter had two additional binding sites than the C-A-G haplotype. However, the MatInspector program failed to detect any gain/loss of transcription binding sites for the insertion or deletion allele in the promoter of UTS2R gene although they showed a difference in promoter activities as described above.

In summary, the present study provided evidence that both UTS2 and UTS2R genes are involved in skeletal muscle fat metabolism, thus leading to abnormal glucose metabolism and insulin resistance in patients with T2DM. Such evidence is supported by the fact that none of mutations genotyped in the population were associated with neither subcutaneous fat depth (P=0.2074-0.9847) nor the fat percentage surrounding the kidney, pelvic and heart fat (P=0.3278-0.7059) (data not

TABLE 2

Associations of UTS2 and UTS2R genes with muscle fat phenotypes*

| Phenotype | | UST2 g.9628G > A | UST2R g.2935-36TA > — | | UST2R c.6506C > T | |
|---|---|---|---|---|---|---|
| rSFA | A/A | 43.55 ± 0.181$^a$ | —/— | 44.40 ± 0.618$^a$ | CC | 44.39 ± 0.311$^a$ |
| | A/G | 43.56 ± 0.224$^a$ | TA/— | 43.73 ± 0.238$^a$ | CT | 43.44 ± 0.168$^b$ |
| | G/G | 42.16 ± 0.518$^b$ | TA/TA | 43.24 ± 0.175$^a$ | TT | 42.64 ± 0.305$^c$ |
| | P | 0.0365 | P | 0.0823 | P | 0.0004 |
| rMUFA | A/A | 50.28 ± 0.193$^a$ | —/— | 48.95 ± 0.651$^a$ | CC | 49.49 ± 0.330$^a$ |
| | A/G | 50.44 ± 0.239$^a$ | TA/— | 50.28 ± 0.250$^{ab}$ | CT | 50.40 ± 0.178$^b$ |
| | G/G | 51.31 ± 0.552$^a$ | TA/TA | 50.60 ± 0.185$^b$ | TT | 51.31 ± 0.323$^c$ |
| | P | 0.2102 | P | 0.0452 | P | 0.0006 |
| $R_2$ | A/A | 14.90 ± 0.174$^a$ | —/— | 16.16 ± 0.585$^a$ | CC | 15.21 ± 0.306$^a$ |
| | A/G | 14.28 ± 0.215$^a$ | TA/— | 14.81 ± 0.225$^b$ | CT | 14.58 ± 0.165$^a$ |
| | G/G | 14.85 ± 0.496$^a$ | TA/TA | 14.46 ± 0.166$^b$ | TT | 14.45 ± 0.299$^a$ |
| | P | 0.0762 | P | 0.0177 | P | 0.1394 |
| REA | A/A | 13.18 ± 0.136$^a$ | —/— | 13.55 ± 0.450$^{ab}$ | CC | 13.40 ± 0.234$^a$ |
| | A/G | 13.21 ± 0.168$^a$ | TA/— | 13.51 ± 0.176$^a$ | CT | 13.25 ± 0.128$^a$ |
| | G/G | 13.14 ± 0.385$^a$ | TA/TA | 12.99 ± 0.128$^b$ | TT | 12.78 ± 0.229$^a$ |
| | P | 0.9847 | P | 0.0488 | P | 0.1187 |
| BMS | A/A | 6.10 ± 0.115$^a$ | —/— | 5.83 ± 0.382$^a$ | CC | 5.86 ± 0.197$^a$ |
| | A/G | 6.14 ± 0.142$^a$ | TA/— | 5.89 ± 0.150$^a$ | CT | 6.07 ± 0.108$^{ab}$ |
| | G/G | 6.16 ± 0.326$^a$ | TA/TA | 6.26 ± 0.109$^a$ | TT | 6.50 ± 0.193$^b$ |
| | P | 0.9669 | P | 0.1075 | P | 0.0558 |

*Each genotype was presented with LSM ± SE (least square means ± standard error) and means within a column without common superscripts are significantly different (P < 0.05) among three genotypes.

shown). Instead, the UTS2 gene was significantly associated with relative amount of saturated fatty acids, while its receptor had significant effects on relative amounts of saturated and monounsaturated fatty acids, $\Delta^9$ desaturase activity for converting 16:1 into 16:0, beef marbling score and ribeye area (Table 2). Although mutations in the promoter regions altered the promoter activities in both genes (FIG. 3) and coding SNPs might affect the mRNA stability in the UTS2R gene (FIG. 2), how these genes regulate fat deposition and fatty acid composition in skeletal muscle remains unknown.

References:
1. Bern H A, Pearson D, Larson B A, et al. Neurohormones from fish tails: the caudal neurosecretory system. I. "Urophysiology" and the caudal neurosecretory system of fishes. Recent Prog Horm Res. 1985; 41:533-52.
2. Ong K L, Wong L Y, Cheung B M. The role of urotensin II in the metabolic syndrome. Peptides. 2007; [Epub ahead of print].
3. Marchese A, Heiber M, Nguyen T, et al. Cloning and chromosomal mapping of three novel genes, GPR9, GPR10, and GPR14, encoding receptors related to interleukin 8, neuropeptide Y, and somatostatin receptors. Genomics. 1995; 29(2):335-44.
4. Ames R S, Sarau H M, Chambers J K, et al. Human urotensin-II is a potent vasoconstrictor and agonist for the orphan receptor GPR14. Nature. 1999; 401(6750):282-6.
5. Sugo T, Murakami Y, Shimomura Y, et al. Identification of urotensin II-related peptide as the urotensin II-immunoreactive molecule in the rat brain. Biochem Biophys Res Commun. 2003; 310(3):860-8.
6. Ong K L, Wong L Y, Man Y B, et al. Haplotypes in the urotensin II gene and urotensin II receptor gene are associated with insulin resistance and impaired glucose tolerance. Peptides. 2006; 27(7):1659-67.
7. Langham R G, Kelly D J, Gow R M, et al. Increased expression of urotensin II and urotensin II receptor in human diabetic nephropathy. Am J Kidney Dis. 2004; 44(5):826-31.
8. Silvestre R A, Egido E M, Hernandez R, et al. Urotensin-II is present in pancreatic extracts and inhibits insulin release in the perfused rat pancreas. Eur J Endocrinol. 2004; 151(6):803-9.
9. Clozel M, Hess P, Qiu C, et al. The urotensin-II receptor antagonist palosuran improves pancreatic and renal function in diabetic rats. J Pharmacol Exp Ther. 2006; 316(3):1115-21.
10. Goodpaster B H, Wolf D. Skeletal muscle lipid accumulation in obesity, insulin resistance, and type 2 diabetes. Pediatr Diabetes. 2004; 5(4):219-26.
11. Pan D A, Lillioja S, Kriketos A D, Milner M R, Baur L A, Bogardus C, Jenkins A B, Storlien L H. Skeletal muscle triglyceride levels are inversely related to insulin action. Diabetes. 1997; 46:983-8.
12. Forouhi N G, Jenkinson G, Thomas E L, et al. Relation of triglyceride stores in skeletal muscle cells to central obesity and insulin sensitivity in European and South Asian men. Diabetologia. 1999; 42(8):932-5.
13. Alexander L J, Macneil M D, Geary T W, et al. Quantitative trait loci with additive effects on palatability and fatty acid composition of meat in a Wagyu-Limousin F2 population. Anim Genet. 2007; 38(5):506-13.
14. Jiang Z, Kunej T, Michal J J, et al. Significant associations of the mitochondrial transcription factor A promoter polymorphisms with marbling and subcutaneous fat depth in Wagyu x Limousin F2 crosses. Biochem Biophys Res Commun. 2005; 334(2):516-23.
15. Jiang Z, Michal J J, Williams G A, Daniels T F, Kunej T. Cross species association examination of UCN3 and CRHR2 as potential pharmacological targets for antiobesity drugs. PLoS ONE. 2006; 1:e80.
16. Zuker M. Mfold web server for nucleic acid folding and hybridization prediction. Nucleic Acids Res. 2003; 31:406-15.
17. Quandt K, Frech K, Karas H, et al. MatInd and MatInspector: new fast and versatile tools for detection of consensus matches in nucleotide sequence data. Nucleic Acids Res. 1995; 23:4878-48.

Example 2

Flow Charts for Tracking the Rearing of Livestock

Figure 6:
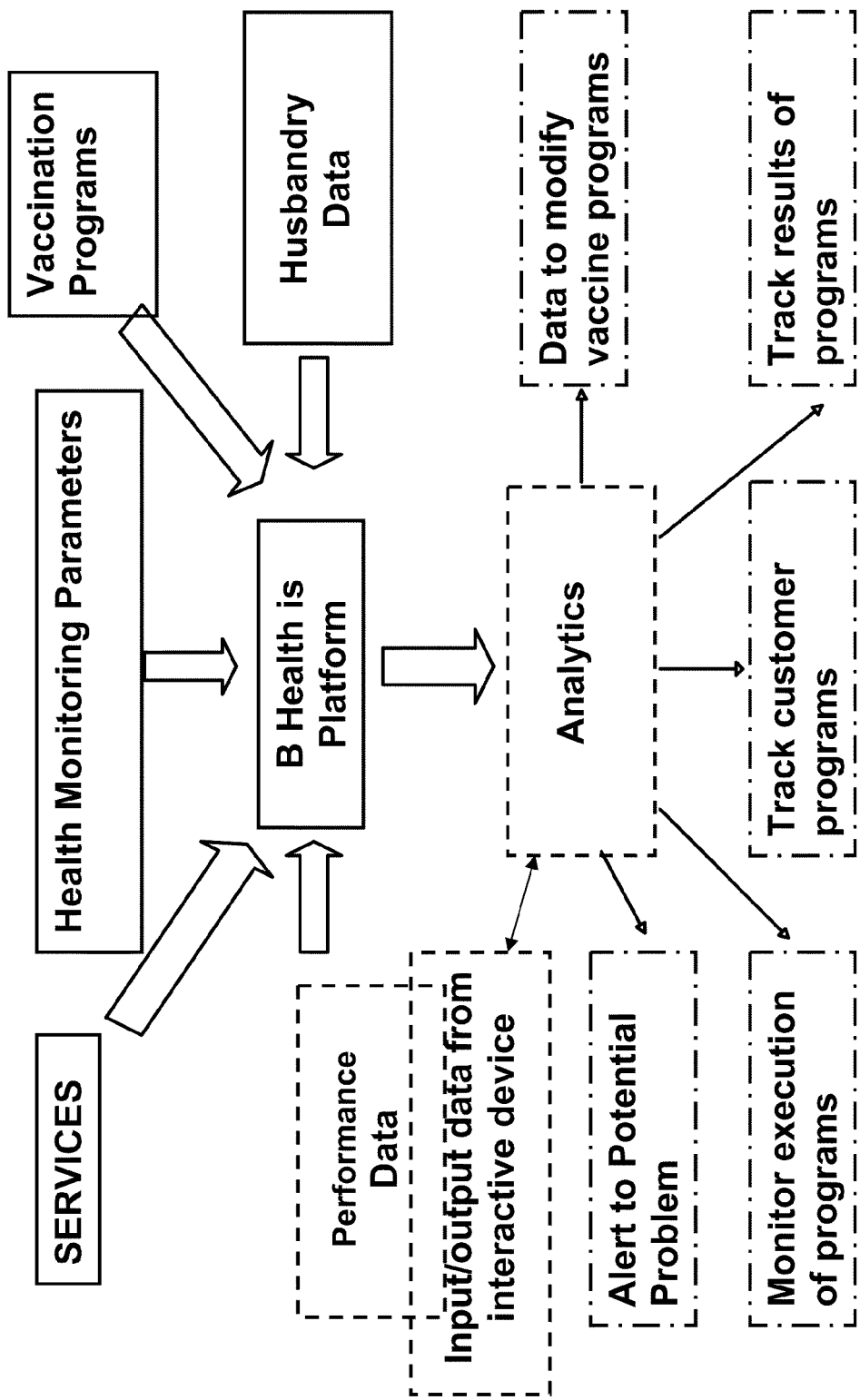
FIG. 6 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 6 shows a flowchart of the input of data and the output of results from the analysis and correlation of the data pertaining to the breeding, veterinarian histories and performance requirements of a group of animals such as from bovines. The flowchart illustrated in FIG. 6 further indicate the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 7:
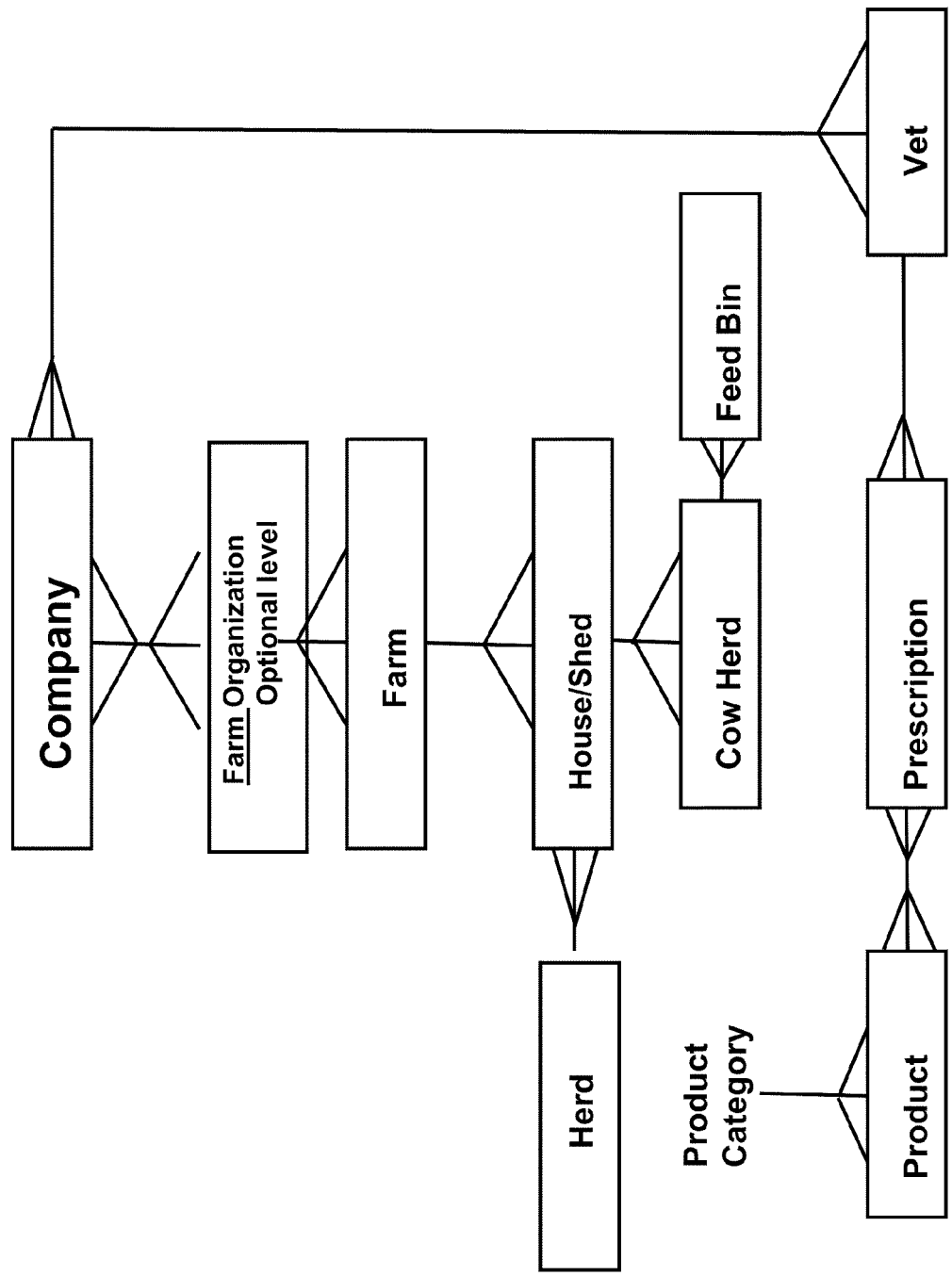
FIG. 7 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 7 illustrates potential relationships between the data elements to be entered into the system. Unidirectional arrows indicate, for example, that a house or shed is typically owned by only one farm, whereas a farm may own several houses or sheds. Similarly, a prescription may include have several veterinarian products.

Figure 8A:
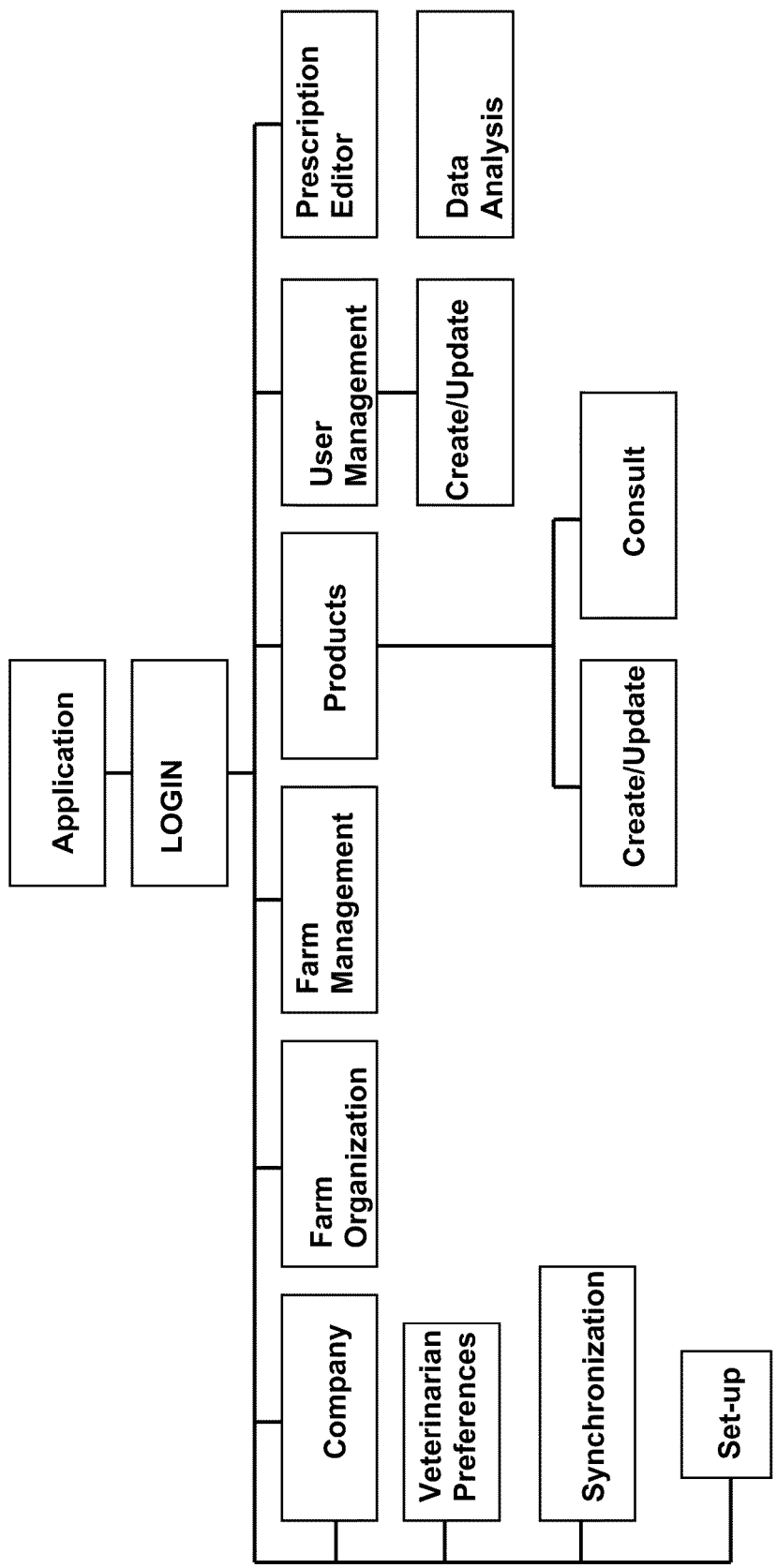
FIG. 8A illustrates the flow of events in the use of the portable computer-based system for data entry on the breeding and rearing of a herd of cows.
Figure 8B:
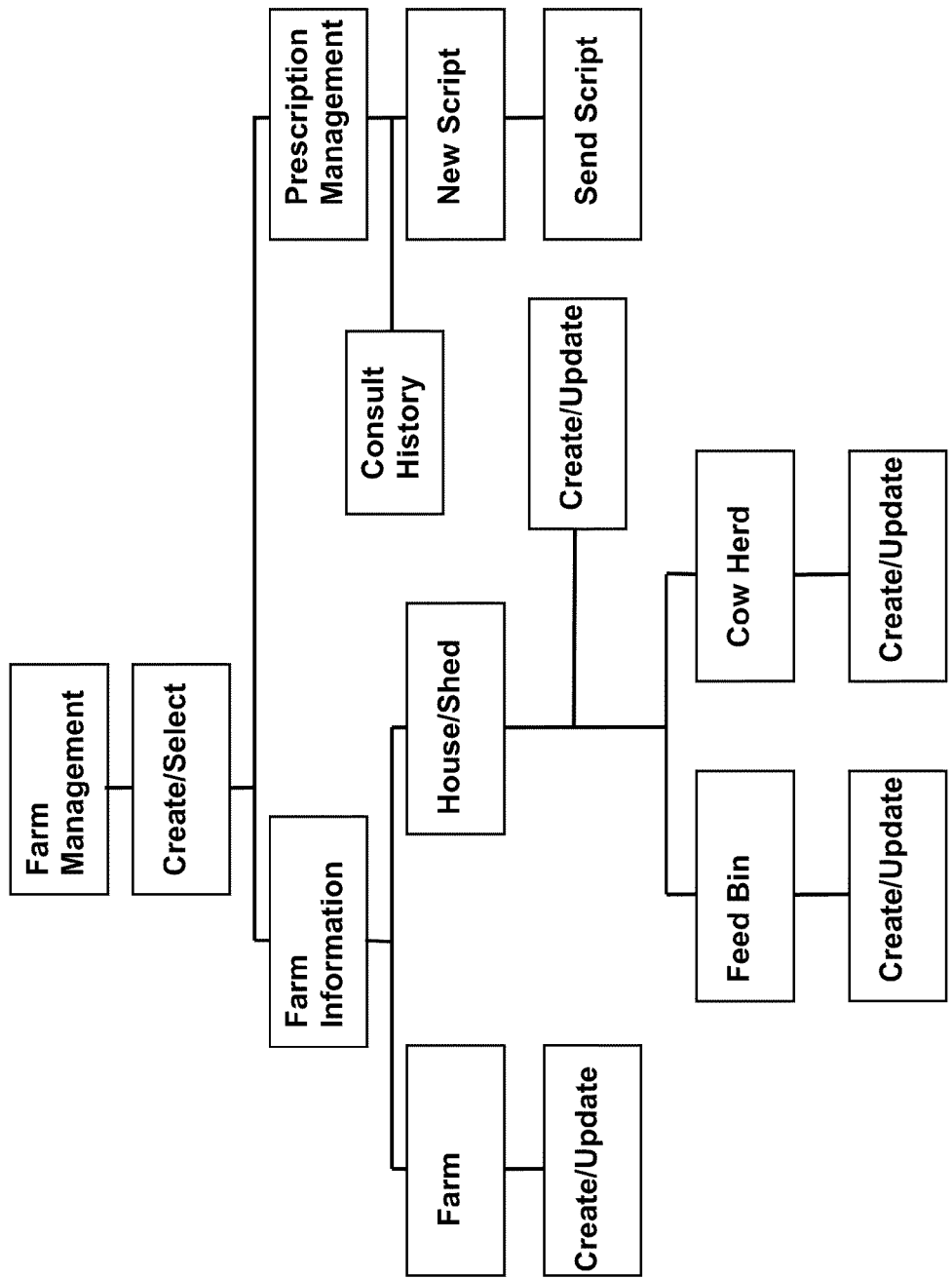
FIG. 8B illustrates the flow of events through the subroutines related to data entry concerning farm management.
Figure 8C:
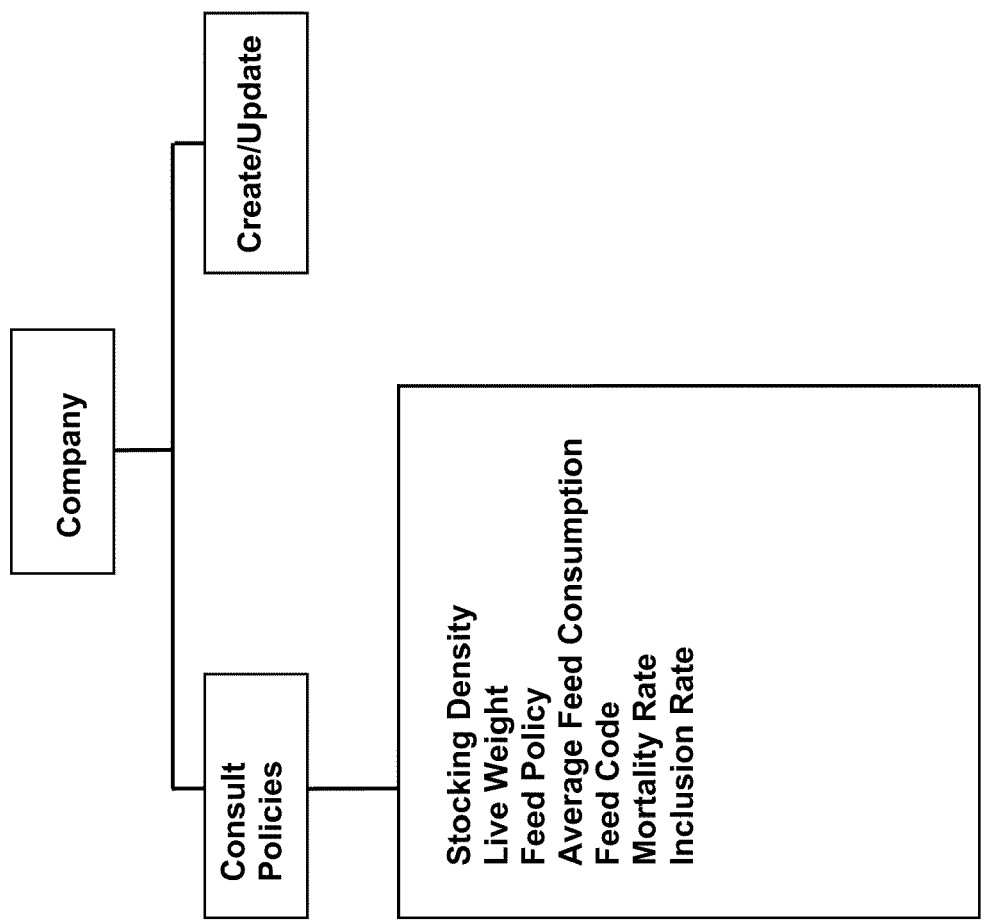
FIG. 8C illustrates the flow of events through the subroutines related to data entry concerning data specific to a company.

FIG. 8A illustrates the flow of events in the use of the portable computer-based system for data entry on the breeding and rearing of a herd of cows. FIG. 8B illustrates the flow of events through the sub-routines related to data entry concerning farm management. FIG. 8C illustrates the flow of events through the sub-routines related to data entry concerning data specific to a company.

Figure 9:
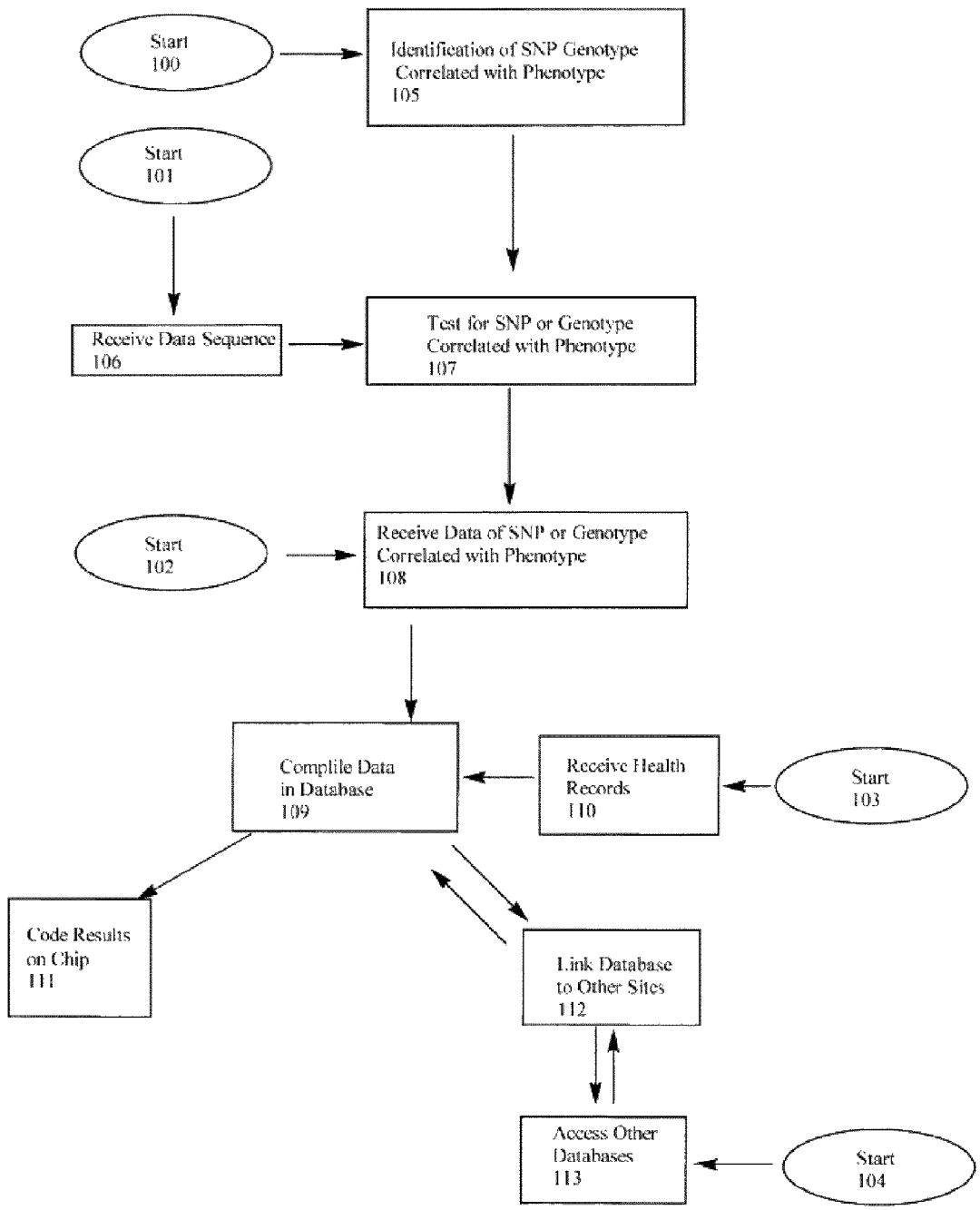
FIG. 9 illustrates a flow chart of the input of data and the output of results from the analysis and the correlation of the data pertaining to the breeding, veterinarian histories, and performance requirements of a group of animals.

FIG. 9 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have similar polymorphism in an UTS2 and/or UTS2R gene comprising:
  (a) determining the genotype of each animal to be sub-grouped by determining the presence of single nucleotide polymorphisms in the UTS2 and/or UTS2R gene, and
  (b) segregating individual animals into sub-groups wherein each animal in a sub-group has similar polymorphisms in the UTS2 and/or UTS2R gene.

2. A method for sub-grouping animals according to genotype wherein the animals of each sub-group have similar genotypes in the UTS2 and/or UTS2R gene comprising:
  (a) determining the genotype of each animal to be sub-grouped by determining the presence of single nucleotide polymorphisms of interest in the UTS2 and/or UTS2R gene,
  (b) segregating individual animals into sub-groups depending on whether the animals have, or do not have, the single nucleotide polymorphism(s) of interest in the .

3. The method of paragraphs 1 or 2, wherein the single nucleotide polymorphism(s) of interest is selected from the group, wherein the single nucleotide polymorphism(s) of interest is selected from the group consisting of the nucleotide substitutions defined in three SNPs in the promoter and two SNPs in intron 2 of the UTS2 gene: AAFC03010889.1: g.9408A>C, g.9552C>A, g.9628G>A, g.13294G>A and g.3900A>C, respectively, one insertion/deletion (INDEL) with two nucleotides of TA (AAFC03013715.1:g.2935-36TA>--) in the promoter region and 13 SNPs in the coding and 3'UTR regions of the bovine UTS2R gene, including AAFC03013715.1:c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively.

4. A method for sub-grouping animals according to genotype wherein the animals of each sub-group have a similar genotype in the UTS2 and/or UTS2R gene comprising:

(a) determining the genotype of each animal to be sub-grouped by determining the presence of a nucleotide substitutions defined in three SNPs in the promoter and two SNPs in intron 2 of the UTS2 gene: AAFC03010889.1:g.9408A>C, g.9552C>A, g.9628G>A, g.13294G>A and g.13900A>C, respectively, one insertion/deletion (INDEL) with two nucleotides of TA (AAFC03013715.1:g.2935-36TA>--) in the promoter region and 13 SNPs in the coding and 3'UTR regions of the bovine UTS2R gene, including AAFC03013715.1: c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively.

(b) segregating individual animals into sub-groups depending on whether the animals have, or do not have nucleotide substitution(s) defined in three SNPs in the promoter and two SNPs in intron 2 of the UTS2 gene: AAFC03010889.1: g.9408A>C, g.9552C>A, g.9628G>A, g.13294G>A and g.13900A >C, respectively, one insertion/deletion (INDEL) with two nucleotides of TA (AAFC03013715.1:g.2935-36TA>--) in the promoter region and 13 SNPs in the coding and 3'UTR regions of the bovine UTS2R gene, including AAFC03013715.1:c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively.

5. A method for identifying an animal having a desirable phenotype as compared to the general population of animals of that species, comprising determining the presence of a single nucleotide polymorphism(s) in the UTS2 and/or UTS2R gene of the animal, wherein the polymorphism is selected from the group comprising the nucleotide substitutions defined in three SNPs in the promoter and two SNPs in intron 2 of the UTS2 gene: AAFC03010889.1:g.9408A>C, g.9552C>A, g.9628G>A, g.13294G>A and g.13900A>C, respectively, one insertion/deletion (INDEL) with two nucleotides of TA (AAFC03013715.1:g.2935-36TA>--) in the promoter region and 13 SNPs in the coding and 3'UTR regions of the bovine UTS2R gene, including AAFC03013715.1: c.6446T>C, c.6506C>T, c.6593T>C, c.6749G>A, c.6830T>C, c.6842A>G, c.7232G>A, c.7359C>T, g.7466G>C, g.7632A>G, g.7692C>T, g.7714G>A and g.7720G>A, respectively.

6. The method of paragraph 5, wherein the desirable phenotype is beef marbling score (BMS), ribeye area (REA), amounts of saturated (rSFA) and monounsaturated (rMUFA), and $\Delta^9$ desaturase activity $R_2$=16:1 to 16:0. or any combination thereof 7. The method of any one of paragraphs 1 to 6 wherein the animal is a bovine.

8. The method of any one of paragraphs 1 to 7 wherein the UTS2 and/or UTS2R gene is a bovine UTS2 and/or UTS2R gene.

9. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

10. The method according to paragraph 9, wherein the computer system is an interactive system whereby modifications to the output of the computer-assisted method may be correlated according to the input from the interactive device.

11. The method according to paragraph 9 or 10, further comprising the steps of inputting into the programmed computer diagnostic data related to the health of the cow or herd of cows; and correlating the diagnostic data to the breeding and veterinary histories of the cow or herd of cows.

12. The method according to any one of paragraphs 9 to 11, wherein the veterinary data comprises a vaccination record for a cow or herd of cows.

13. The method according to any one of paragraphs 9 to 12 wherein the health data is selected from the group consisting of husbandry condition data, herd history, and food safety data.

14. The method according to any one of paragraphs 10 to 14, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

15. The method according to any one of paragraphs 9 to 14, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

16. The computer-assisted method according to any one of paragraphs 9 to 15 for optimizing efficiency of feedlots for

39 livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

17. A method of transmitting data comprising transmission of information from such methods according to any one of paragraphs 9 to 15, selected from the group consisting of telecommunication, telephone, video conference, mass communication, a presentation, a computer presentation, a POWERPOINT™ presentation, internet, email, and documentary communication.

18. An interactive computer system according to any one of paragraphs 9 to 15 for tracking breeding and welfare histories of cows comprising breeding and veterinarian data corresponding to a bovine or herd of bovines, and wherein the computer system is configured to allow the operator thereof to exchange data with the device or a remote database.

19. The interactive computer system according to paragraph 18, wherein the input and output devices are a personal digital assistant or a pocket computer.

20. A method of doing business for tracking breeding and welfare histories of livestock comprising breeding and veterinarian data corresponding to one or more livestock animals comprising providing to a user the computer system of paragraph 18.

21. A method of doing business for tracking breeding and welfare histories of livestock comprising breeding and veterinarian data corresponding to one or more livestock animals comprising providing to a user the computer system of paragraph 19.

40

22. The method of doing business according to paragraph 20, further comprising providing the animal owner or customer with sample collection equipment, such as swabs and tags useful for collecting samples from which genetic data may be obtained, and wherein the tags are optionally packaged in a container which is encoded with identifying indicia.

23. The method of doing business according any one of paragraphs 9 to 15, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

24. The method of any one of paragraphs 7 to 23 wherein the data comprises presence or absence of one or more of a single nucleotide polymorphism(s) of interest in the RFI gene (s).

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A method for identifying a bovine as having: a higher relative amount of monounsaturated fatty acid (rMUFA) in beef fat phenotype as compared to the general population of bovines; a lower Δ9 desaturase activity as measured by 16:1/16:0 ratio (R2) phenotype as compared to the general population of bovines; and a smaller ribeye area (REA) phenotype as compared to the general population of bovines, said method comprising:
   (a) obtaining a biological sample from a bovine, said sample comprising nucleic acids from said bovine including the bovine urotensin 2 receptor (UTS2R) gene;
   (b) detecting in said nucleic acids the presence of an insertion allele of the g.2935-36TA>--polymorphism in the bovine UTS2R gene in both alleles of the bovine UTS2R gene, wherein the insertion allele comprises TA dinucleotide content at the positions corresponding to positions 379 and 380 of SEQ ID NO: 2; and
   (c) correlating the presence of an insertion allele of the g.2935-36TA>--polymorphism in the bovine UTS2R gene in both alleles of the bovine UTS2R gene with a higher relative amount of monounsaturated fatty acid (rMUFA) in beef fat phenotype as compared to the general population of bovines; a lower Δ9 desaturase activity as measured by 16:1/16:0 ratio (R2) phenotype as compared to the general population of bovines; and a smaller ribeye area (REA) phenotype as compared to the general population of bovines.

2. The method of claim 1 further comprising sub-grouping bovine animals according to their genotypes.

* * * * *

SEQUENCE LISTING

```
<160> NUMBER OF SEQ ID NOS: 28

<210> SEQ ID NO 1
<211> LENGTH: 7435
<212> TYPE: DNA
<213> ORGANISM: Bos taurus

<400> SEQUENCE: 1
gccttgagat tgaatttttg ctgtgaattt atcttcattt tttaaaagta aataatctgt      60
tttgacttta atttcatgcc ttgtcattcc tcaggcattg ttgttcagtc actaagttgt     120
gtcagactct ttgtagccct atggattgca gtacaccagg cttcctggtc cttcattatc     180
tccctgagct tgctcaaact catgtccmtt gagtcagtga tggcatccaa ccatctcatc     240
ctttgtctcc ccttctcct cttgcctcca atctttccca gcatcagggt cttttccaat      300
gaggtggctg tttgcctcag gtggccaaag tattggagct tcagcttcag cmtcagtcct     360
cccaatgaat acttagggtt gatttccttt aggaaatctt caggcatgaa gccccaaaga     420
aaaaatgrca gttcatctat tcattcacaa aagattaaaa aagaaaatca acacatttca     480
cgcagtgctc cacaatactt ctgctgggta agactcataa atccatgtcc ctgtcttgga     540
cacttcaact cctgtctgat cctttcttta actagagatt tattgctctc aattactcct     600
ttttgccaga tttataaacg taactgttct ttatttaata cctattttgt acactaggca     660
acaagacagt aaatttattg tctatgagtt gctactttga aaaattacat caatgcagag     720
tgattgcttt tcagccttcc tagccaataa attcatttct tttttttttt tttgtagggg     780
atgatatgag gtcataggat aatatatata atcgctgatt acagaattag aagaagcaag     840
ttgcaggcaa ctgctctaac actggactct accccgaga aggagcaagt tggaagaagc       900
```

```
taagaaggaa gacttctatc tcctgccaat catgtataag ctggtctcct gctgtttgct      960
tttcatagga tccttaaatc cgctcctgtc tcttcctgtc cttgactcca ggcaagagtc     1020
cctgcagctc ttaggtaaga tgattttttt cccccttatgt tagtcttgaa caagtcttca    1080
agggtcttaa atgcaaagtt aaagatgaaa attctctctt aaaggagtct tgttaatagt    1140
cccagctatg aaaagaattc tgaggattct taaggcatgt ctcagagtca agaatggata    1200
cagttttttc ctttctaaaa tataaaagta aaggggaac attgcttatt taacgtgact     1260
tctgtaattc tgagttattt tggtcagtct tttttttctg ttttgaaaat agcactaaat    1320
ttaaaacacc attgctttta gtctttattt taagtgaact ggttgaatgt agaactggtt    1380
gttccaatta tagattaaag tattttgatt ttatcttata ttattttaag ttaaaaggca    1440
atcatctgac atgtgttaca tgaaaaaaaa atgttttta aaatataaaa aagtaaccag      1500
ctgggactag agtagacaca gatttccaag ttcattttat cttttccttc tggtttatgt     1560
ttcattcagt tcaattctaa gttgaatttt ttaaagtgta tcaatcaagg agatacttat    1620
tgtactttta gctcttcatt taacttaaga aatgaaaagg ttggggaaaa aaagaaaaga    1680
aaaagttgat gtttggggat tgtgttcata aacattttaa ctggattta acttgtcttt     1740 aattgtggat acttttagac attttttta aataaaggaa ataaaactct ggtaagccag     1800
taattttata atttctagtc cataagtttc tccaaagcag ctttcttttt tttttttttt    1860
tgataattta aattttattt tattttaaa ctttacataa ttgtattagt tttgccaaag     1920
cagctttctg ataatagtca agcactaatt cgtgcacaat taatcacttt ccagagtcac    1980
tgaactcaga agtggcagtc atcttaatgg ttaaaatgag cattaacttt atcgaatctc    2040
tgctatttaa aaaaaaaaa aaactttga aaagcataag gtgaaacgaa gaatgaatat      2100
tcagatatta ctgacatcct caaaaaatta catgtcatta ttatgatttt ttaaaaactt    2160
gagtgagtgt agcatcccct ttccaattct taataggtgg cagcttatct tagcattttt    2220
gcctgaattt ttttcctactt acttgtttct ccataaatga tccttccctg gtggctgagc   2280
aatgcaagag actctggttc aatccctggg ttgggaaggt ccctggaaa aagaaatggc     2340 aatctgctcc agtattcttg cttgaaaaat tccatggaca gaggagtctg gtgggtcgca    2400
gaagaatcgg acatgacttg gcaactgtaa acaaacaaca aaacaaatga tccttcatga    2460
caaaaatatt gatatgtagc caaactttgt agactttcat taacattctt cagaagtacc    2520
atgaagcctt catgatggct tgcttttat tctgcaatca aggttggagc tgagggtttg     2580
aaagccttag tgaagcaggc actccctgct tcactgcttt tacaggactc cctgggggct    2640
ctgatcaccg caaggcagaa acctgccaag agaacaatct gggcccagta tcactcacca    2700
gccctcacac tcacctttcg cacacctgac acaaacttac catccatctt ctatgctacc    2760
aagctgacca aattacatgc tgaaaatgtt gctatcaact tgttcaaaga atattgtaaa    2820
gctgacttgt ttctgatcat tgtatctaaa tcttagaggc cagagaagag gtgatgttat    2880
cctatttgct ttaggtgtgt gtgagtgagt cactcagttg tgtccaactg tttgtcatca    2940
ccatggatat tagcccacca gtctcctctg tccatgggat tctccaggca agaatactgg    3000
agtggtcacc attcccttct ccaggggatc ttcctgaccc cagggatcaa gcctgggtct    3060
tctgcattgc aggcagattc tttattgtct gaaccacccg gtcggaagaa cataaacaag    3120
cccgtctttt agaaaaccac tcctttactt ttcctctcac tccaatttcg ccacccctat    3180
atctaaaagc aaaaggcaaa tgatagcagt aggtaaacag agacgaagaa gaatcacttt    3240
gtaagtggaa atgttttttc actgatcctg tggctcagcc caatccttt tttttttttt     3300
```

```
ttgattttta acatttttaa tttctttact ttttggatca catgggatct tagttccccg    3360
accaggcatt gaacccacac cctctgcagt ggaagtgtga agtcttaagc actagaccac    3420
cagggaagtc ccagccctac cttcttattc agggtggtga gcatccagca aggctgtgca    3480
ggcaggagga gtcaggatga gaaccatgcc tcatgatttc ctgttctgct ggcttgcaaa    3540
ttggactgta gcgttcccac ttctctgtta aaatactgct aatgacaaac catgaactca    3600
gtatttgaaa tctgtctagt attagcttcc tgttcctggt gcatgctcat gctcagtcac    3660
tcagttgtgt cccactcttt gtgacccat gagcctcctc tgtccatggg atttcccagg    3720
caacaatact ggaatgggtt gccatttcct cctccagggg atcttctcaa cccagggatt    3780
gaacctgttt ctcccgcatt acaggcaaat tcttaaccac tgagccccct gggaagcccc    3840
tccctgtccc tggtacctcc ctaaagacaa tggggaacag aactgaagca ggagctgtca    3900
ctaatatcaa tcattgctct gtgtagcacc tgaagatgtc agatcaactc tggatgagct    3960
ggaaagagcg tctcttctgc agatgctgcc agagatgtca ggcgcagaga caggagaggg    4020
tcttaggaac acaggtaaaa tgactcgtgt ttacaggctg tctgatttct ttgctactga    4080
atttactctg agtratcaca ctctcccctc ctgcatacag tcttcctctg ccatcttctg    4140
tctccttttt ctcagcaact ccttgcaagc atccttctct gcttggcccc tcggcatatt    4200
tgttctctgt atgatttggg gggtgggagg caaggggagg gaagaagagc attatcccag    4260
ttttcaataa gtacaattta caatgctggt ttccctctta gatgagttaa tctatctgta    4320
tctcaaattc ttaaaccagt acacaggaat gattaaaaaa caaaattccc atcgcatggg    4380
gttattgaga agattcaatg aggaaatgca agtaaaatgt tcatcacaaa cacaaaataa    4440
cccatgtcag cttttactgt tttctcagtg acagcgttcc tcctagcaca gatacaaatg    4500
ctcagaacat tctggagtct tttaataaat ttggttttgt agaaagaaat tcatgtgtga    4560
taaagtattg ttgacaaact actgaactgc taactcactg aggaagatgc agtgcccttt    4620
gtgaactctg ggggctagaa aagagccagg tgcttgcctg tcctccatca aataaatatc    4680
actgcggtgt gaagaaaggm aaaccagaaa ctagacatga tttagtaata ttctatttg    4740 tatgttttaa ataagacaaa gataaaatgg aaataataga tctgatgatg aatggtttca    4800
aaatactgtt ttccagatcc cattaccaac atttttttacc caagaggaaa catgagaaag    4860
gtaagtaggt cctatatgag agttaggata aaaaggtga acatttctat gccttgactt    4920
tagaggagcc tcagtaggaa ccagtcaagc cttctcagta caaatcttaa cacccagtat    4980
tatttcaaag cattattttt tttccaaatt ttgatccatg taaaatgggg atacaacaag    5040
aacttaccta gtgttcatct ctgataaatg atgataacaa gttttagaga atcaaaaata    5100
gataaagccc ttgccctcaa gcctgtcatc cacttgcgct gtgtcactga ttatcttcac    5160
tgggtccaag gaccagcagt gctggtgtca cacggaagct tgtgagaaac gcagactcac    5220
cccaccccct acacctactg aatcaaaatc tgcatcttaa caggatttcc ccacgtggtt    5280
tgtatgcaca gtaaagtttg aaaagcactg tcatataata tctaaatgga agaaaggcat    5340
ggtcgaaaca ttgagaggga atatgtgtgg taaaggagaa tatgaaggag ataatttgg    5400 gtgcaaaagg cagactacaa taggacatga ttaatgaaaa tattaaatgg ttagaaatgg    5460
tgcacaatta atggaggacc ttaactgcta caagagaaat cggttttgat cattatcaac    5520
ccctcaaact aaactgagct cagttgttca gtcatgtctg actctttgga accccatgag    5580
ctgtagccct gccaggctag tctgtccatg ggatttccca ggcaagaata ctggagtagg    5640
gtaccatttc ctttccaggg aatcttgctg gcctaaggat caaacctgcg tcacttgcgt    5700
```

```
ttcctggact ggcaagtgaa ttttttacca ctagccccac ctggaaagcc ccaagctaaa    5760
ttagtgtttc ctaaaggatt ttctgtaagg tcctttgaat taccctgtag ctcttttggt    5820
aaagaacctg cctgcaatac aggagacccg ggttcaattt ctgggtcagg aagatcccca    5880
ggagaagaaa atggcaaccc acttcagtat tcttgcctgg agaatcccat gggtagagga    5940
gcctggtggg ctacagtcta tggggtcgta agagtcagac acaacttagc gactaaacca    6000
ccaaaggatt ttctgtgaat atcagtccca tagagtcagt ctacagggct gccctgcatt    6060
ctaacccctc tcctgtcctg gcaattcttt gtgtataaag cctccaggaa atgagataaa    6120
tgtatttaat tttaatcaag aatttcccaa atattttgac cagaaacatc ttcttttggt    6180
gtagtgccca ctaacctcct tgtaaaaata taccatgaaa gccctcaatt ctgaagatgg    6240
catacactgc ctgaggttcc caggtagggt agaccacaca gaaggggagg gtgtggctcc    6300
tattacatta aaagttatca ctcagatatt tatattcttc tgaatagaaa gattatggtg    6360
aaagactcta aaatcataaa ggtgattagt agagatgctc ataaaatcct agaataaaaa    6420
gaaaactaaa ggtccatgat taatttcaag acaaataaaa gacctgattt acacagaaga    6480
cattaaatgt acagaacatg ttactgagag atgaaataga aacaggtaaa tgaaggttta    6540
ggaaaattca tggcaatcac gaggctaaat agactggatg gaccacaggt tgggcacaag    6600
gagacctttc agagtctaca tactgggtgc tcactgcaat tctatcccat gaaacagcaa    6660 gaaaacccctt tttaaaaccc ttttaaaggt cctgtatctg agtaaggttc atttgtgtgt    6720
gtgtatggca ctcaattaat tgataaccta tttttttaat ttcaggcctt ctctgggcaa    6780
gatcctaagc ttttcctgag tgaccttttg tccagaatta ggaaacaatc taagaaacgt    6840
ggaccttcct ctgaatgctt ctggaaatac tgtgtctgaa gcaaaatgac cctctactag    6900
ttacctccaa gacgaccatc tgagaaaatg taaaataaag atgcttgatt tgaaagcagt    6960
atagatgaaa aactaggcaa gctagaccct gttcattatt atttggaaaa taaatcctct    7020
atgttttgca gatactatga gtggttgttt tacttaaaaa cgtatcctga aaacaaaca     7080 aaaaagtac cctgaaaatc tatactttt cttttttaaa ataattttat ttattttggg     7140
ctgttctgga tcttcgttgc tgtgcaggct tttctctagt tgacgtgagc ggggctgctc    7200
tctagtcgtt ttgcacaggc ttgtcactgt ggtggcttct cttgttgcag aacacggact    7260
ctggggcaca cgggcttcag ctgtggctcc cgggctctgg agcacaggtt cagtagctgt    7320
ggcacgtagg cttagcttct ccgcggtatg agggatcttc ctgatcaggg atcaatccca    7380
gtcccctgca ttgacaggtg aattcttttac cactgagcta ccagggaagc cccta        7435
```

<210> SEQ ID NO 2
<211> LENGTH: 5557
<212> TYPE: DNA
<213> ORGANISM: Bos taurus

<400> SEQUENCE: 2

```
cagcactagt caccatcacc aaaatcatcc atcagggatg aagggaaaaa caaagtgatt     60
taccttgaat cagaagatat tcttcagggc gcttccctgg tggtccagtg ctaagaccc     120 tatgctcccg gtgcaggggg cctcggttca atccctggtc ggggaactag atcccacatg    180
gtgcaactaa gacctggccc agccaaataa ataaatacat taaagaagaa aaagaagat    240 agtcttcagt cttctgaata cttcactctt ctgtcttcac agaatactct tcagtcttga    300
aaaggatgga aactcttacc cttgctacaa catgaaggaa gctcaaagac atcatagtaa    360
gtgaaagaag ccagacacta agggacgaat gtatgatccc actcacagcg ggtccttaga    420
```

```
gtagtggaat ccatggagac caaaggagaa tggtggttgt cagggggctgg gggaatggga    480 tgtggagttg tctaatgggg acaataaaag gtttgtgttg ataaaaggtt ttggaaatag    540
tgacgagtgc acattatgaa tgtctttaat gacactgggt cctggcctcg catgggtctc    600
tcagaaccac cctccaccca ctgcgtcccc cacaggtgca gaggagggtc cagggcttga    660
ctgacaatct gaatccgagt ccgaggctca gtgcttggga aactgagggg tggtggagtg    720
cagagggcga agggaagcag agacgctccg cggtggggcc agccaggctg gactgagctt    780
caccccatgg atgcgtctgg agtcccagct gcgccgtgat ctgccctctc gctttgccac    840
cccccgctcc cgcccctgct gccctcccgt ccctgggcct ccgtggctcc ccccaccgca    900
gcgcatcctc gcccccctctc tagcagcccc cctcccgcgg gttattaata tccgggccgg    960
gcgcagggcc gccgcgcatt cccagctggc agccgggcag gtggcgccgg cgacaggggc   1020
ctgggcgcgg aacgcggctc tccaggcgag accggcgggc gggctcccct ccaccacgcg   1080
cccctgggag cccccacgtc ctctgcgcgc ccctaccggg cagagccctc ggaaaggttc   1140
ccgtgccgcg ccgagtgttt ggagacgctt agcgactaag cgccggtcca gagcacgacc   1200
ccagggtgct cggcgcccac acctgacggc cggtgacgga ggtgggcgca ggcactgcga   1260
gggtgcgggg cgggagaagg ggccgggatc ctcccggggc ggggcgccct ccccgctggc   1320
ccgcacaatc ccctgcagga tcgctcggcc acgaagccct cccagcggac ccccgggaga   1380
tgcgtggcgc ttcggagggt ggagagggtg aggtgtgcgc ggtgggctcg gcggctgttt   1440
cgcgtccctc ccgggaggtc ctccgccagg ttcgcggtag ccctgcgggg agggctctgg   1500
aaccagaacc cactggggc tgcggccgcg gagggcgcct cgggccggta ggaaagaccc   1560 cagctccct cgccagaccc aaggctgagc caagtcccac gggcagggg cctaggacag   1620 cgtctctaca cccagcttgc ccttctgcac cgagtgctca gttggacgcc ccgagtttat   1680
ccatgttagt gcgaacgctg tacctgtaga gggaaaaaac cgggaaccag ttttatccgg   1740
ccacattatc cctagatgtg gggagattgg gccataaagg ggcctctcct ctcattcaag   1800
tattcaggtt ttaggtctct ttttttctcat gagggtaatt ttcacccagt aagcacgggt   1860
catgagtgtg caactccagg agtttttaca tgtccgtagt cgctaagtcg tgtctgactc   1920
tttgggaccc catggaatgc atagcccgcc agactcctct gtccatgggg agaatgctgg   1980
agtgcgttgc catgccctcc ttcagggat cttcccaacc cagggatcaa acccaggtct   2040
cctgcattgc aggcggattc tttaccatct gagccaccag aacacctgtg taaccagtgc   2100
cacatgagga catagcacac gtccgtcccg gagtgctctc cggtgccccc taccagttga   2160
caccctcttc aaccactcat agagattttt tcttttcccc agcttcattc aggtaaaggg   2220
aattatacag tgtgtacttt ttgtgtatgg tttctgtttc atccccccccc cccccccac   2280 tcaacagagc atatttgagt ttcatcaagt tgctgactgt tcaataattt cattttcttc   2340
atcaccttgg agcatttta ttgggggggg ggtgtcagtt tctttatcca tactactaat   2400
caccaacgtt tgggtggttt ccagcttctg actgctatga acgttctcac tcttgctttt   2460 tatgccatt tgcactaatt tttcttggca taaacctaag agtagaattg ctgaatgaga   2520
ggacagacgt gtgtccagct ttactaaggg tgccagattg ttcgccacag gcggctgcac   2580
tgttcttgtc ctccactagc agttcaggag ttcattcct tcatgtcctc ccagcagttt   2640
tacgaatttc ctgttcaaat tttgtctttt ttttcctttc agttgagtca ttgctcttta   2700
ttgatctgta gttcttcac atattttgat tactagttcg ttgtctgata tgtgtcttct   2760
gatgatcttt tcccagtcca tggtttacat cttttactct ctcagtgaag ttcttaattt   2820
```

```
tcatgaaatc caattggtgg gtcttttact gcaagcattt tttgctttt tttttttttg    2880 aaaaatcttc atttacccac agtcatgcag atattctcct gtatttcttc cagagcttga    2940
ttaattaatt gatttaatct attacataag gtacacagtc caccttgaat tgttttcttg    3000
tgtggtagga tataggaatc aggtttattt ccccatgtg aataaaggaa gattatgagg     3060
gctttcccct ctttaacata ttttcctatt tgaactttaa agtcggcaga tattactttt    3120
gcaatctgaa caaaatgtat tttcttaaaa catacaggag aactatatgg ggaggaagac    3180
ataggggtca gccgggcttc cctgcccttc agggatgagg aagtgagaag gcctagtgag    3240
aactcctggt tcatccagga gtgaaccatc ctggttcatg cctgctgtgc tctgattttc    3300
aggaaaggcc atccagctga gaggcctttg aacttgcact gtgggccag gtgagaatgc     3360 tactggggca tgcatggggg gcaactggtc tgggtggtac tctggtcccc ctggatagct    3420
ggggaactga agcagagtgt tagagttctg catggagagt cccccagggg gtatcacagt    3480
tggtgagcac tgtccctctg caggcctccc agcctggtgg gaactgtggc ctcttatggc    3540
ctcttgggag tgggaaaggg tgcctgacct gcatctttaa tgagcatcct ctcctgcagg    3600
acaagcttgt tgcccacaga tgccccctct ctacctaaag gagcagcagg ccccagcccc    3660
aagcccagtg tgaggtggca gagatggcac tgagcccaga gccatcgagc aggttcctgg    3720
tgccggctac aatgggcagc gccatgcccg agctgcctgg tgccccaat gcgtccctca     3780 acagctcgtt ggctagcccg acggagccca actccctgga agacctggtg ccacgggca     3840 ccatcggggt ggtgctctcg gccatgggtg tggtaggcat ggcaggcaay gtgtacacgc    3900
tgacggtcat gtgccgcttc ctgcacacct ctgcctccat gtacgtctay gtcatcaacc    3960
tggcgctggc agacctcctc tacctgctca gcatccctt cattgtagct acctacgtca     4020
ccaagaggtg gcacttyggc gacgtgggct gccgcgtcct cttcagcctg gacttcctga    4080
ccatgcacgc cagcatcttc accctgaccc tcatgagcag ggagcgctat gccgccgtgg    4140
tgaggccgct ggacacggtg cagcgttcca agggctatcg taaggtcctg gcrctgggca    4200
cgtggctgct ggcactgctg ctggcactgc ccatgatgct ggccatccgg ctggtccgca    4260
ggggccacaa gagyctctgc ctgccrgcct ggggccagcg cacccaccgc gcctacctga    4320
cgctgctctt cgggaccagc atcgtggggc ccggtgtggt catcgggctg ctctacgtcc    4380
gcctggcccg ggcctactgg ctgtcgcagc gggcctcctt cacgcagacg cggcggctgc    4440
ccaaccccag ggtgctctac ctcatcctgg gcatcgtgct gctcttctgg gcctgcttcc    4500
tgcccttctg gctgtggcag ctccttgccc agtaccgtgg ggccccaccg ctcgctcccc    4560
gctccgcccg catcgtcaat tacctgacca cctgcctcac ctatgcaac agctgtgtga    4620 acccttcct ctacacgctg ctcaccaaga actaccgtga ctaccgccaa cgctcrctcc     4680
acagcagggg caccagtggg cctgtgggcg tccgcagctt cccacagggc cacccgct     4740 gccagctcgg ctcgggtcgc tccgtgacct ccagcagcca gcaagccact gagaccatcg    4800
caytgtccca ggcggtcccc gggagtctct gcgtctgagc gtccccagcc tccctgtggg    4860
ccctgggggt aggctgtggg gagtggcccc tggagcccag gtctctccts gaccaccctc    4920
cccacggtct gcctcccttc cccagtcctc ttccagaaag ctcctggctc tccctcaccc    4980
ctcactcact tcagctccat cagtgcagct actttcctca taacgccaag aagtgccccc    5040
aacccagtcc atctgtgagg gtctgcagga ggctcrggct cagggccagc tcctgaagac    5100
cgtggtgagt ggagtcttca ccagccccct gcagaygtgaa ctgcgtacct gacgcacrac    5160
aggrtacacc gtggcaggtg acaccatgtt gccacacaag ctgcctgtgt gggaccctcc    5220
```

```
tcctggcatg agcgtggccc cagtggcacc catttctccc aactgccatg tggttccatc    5280
ccgcacagct tcagcacctg aacaataaa cgctgagctc cctgagtctt gtctgcaaca     5340
gcagtgtgag tggggtgtca aaggaggcag accccagg acgtcctcct gcacttggag      5400
gagcccatct gcctgaccgg gcaggggaca tgtctggcca ttaggccttc ctgacatggt    5460
gggtgggtgc catctggcct gagccaggcc ctgggtgtgg ggcctgagac cctggggtga    5520
gtgaggcggg gagccaccag cctcaacctg ctcaggg                             5557

<210> SEQ ID NO 3
<211> LENGTH: 5555
<212> TYPE: DNA
<213> ORGANISM: Bos taurus

<400> SEQUENCE: 3
cagcactagt caccatcacc aaaatcatcc atcagggatg aagggaaaaa caaagtgatt      60
taccttgaat cagaagatat tcttcagggc gcttccctgg tggtccagtg gctaagaccc     120
tatgctcccg gtgcaggggg cctcggttca atccctggtc ggggaactag atcccacatg     180
gtgcaactaa gacctggccc agccaaataa ataaatacat taaaagaaga aaaagaagat     240
agtcttcagt cttctgaata cttcactctt ctgtcttcac agaatactct tcagtcttga     300
aaaggatgga aactcttacc cttgctacaa catgaaggaa gctcaaagac atcatagtaa     360
gtgaaagaag ccagacacag gacgaatgt atgatcccac tcacagcggg tccttagagt      420
agtggaatcc atgagacca aaggagaatg gtggttgtca ggggctgggg gaatgggatg      480
tggagttgtc taatggggac aataaaaggt tgtgttgat aaaaggtttt ggaaatagtg      540
acgagtgcac attatgaatg tctttaatga cactgggtcc tggcctcgca tgggtctctc     600
agaaccaccc tccacccact gcgtccccca caggtgcaga ggagggtcca gggcttgact     660
gacaatctga atccgagtcc gaggctcagt gcttgggaaa ctgaggggtg gtggagtgca     720
gagggcgaag ggaagcagag acgctccgcg gtggggccag ccaggctgga ctgagcttca     780
ccccatggat gcgtctggag tcccagctgc gccgtgatct gccctctcgc tttgccaccc     840
cccgctcccg cccctgctgc cctcccgtcc ctgggcctcc gtggctcccc ccaccgcagc     900
gcatcctcgc cccctctcta gcagcccccc tcccgcgggt tattaatatc cgggccgggc     960
gcagggccgc cgcgcattcc cagctggcag ccggcaggg ggcgccggcg acaggggcct     1020
gggcgcggaa cgcggctctc caggcagac cggcggcgg gctcccctcc accacgcgcc     1080
cctgggagcc cccacgtcct ctgcgcgccc ctaccgggca gagccctcgg aaaggttccc    1140
gtgccgcgcc gagtgtttgg agacgcttag cgactaagcg ccggtccaga gcacgacccc    1200
agggtgctcg gcgcccacac ctgacggccg gtgacggagg tgggcgcagg cactgcgagg    1260
gtgcggggcg ggagaagggg ccgggatcct cccggggcgg ggcgccctcc ccgctggccc    1320
gcacaatccc ctgcaggatc gctcggccac gaagccctcc cagcggaccc ccgggagatg    1380
cgtggcgctt cggagggtgg agagggtgag gtgtgcgcgg tgggctcggc ggctgtttcg    1440
cgtccctccc gggaggtcct ccgccaggtt cgcggtagcc cctgcgggag ggctctggaa    1500
ccagaaccca ctgggggctg cggccgcgga gggcgcctcg gccggtagg aaagaccccca    1560 gctcccctcg ccagacccaa ggctgagcca agtcccacgg gcaggggcc taggacagcg     1620 tctctacacc cagcttgccc ttctgcaccg agtgctcagt tggacgcccc gagtttatcc     1680
atgttagtgc gaacgctgta cctgtagagg gaaaaaccg ggaaccagtt ttatccggcc      1740
acattatccc tagatgtggg gagattgggc cataaagggg cctctcctct cattcaagta    1800
```

```
ttcaggtttt aggtctcttt tttctcatga gggtaatttt cacccagtaa gcacgggtca    1860
tgagtgtgca actccaggag tttttacatg tccgtagtcg ctaagtcgtg tctgactctt    1920
tgggacccca tggaatgcat agcccgccag actcctctgt ccatggggag aatgctggag    1980
tgcgttgcca tgccctcctt caggggatct tcccaaccca gggatcaaac ccaggtctcc    2040
tgcattgcag gcggattctt taccatctga gccaccagaa cacctgtgta accagtgcca    2100
catgaggaca tagcacacgt ccgtcccgga gtgctctccg gtgcccccta ccagttgaca    2160
ccctcttcaa ccactcatag agattttttc ttttccccag cttcattcag gtaaagggaa    2220
ttatacagtg tgtactttt gtgtatggtt tctgtttcat cccccccccc cccccactc    2280 aacagagcat atttgagttt catcaagttg ctgactgttc aataatttca ttttcttcat    2340
caccttggag cattttatt ggggggggggg tgtcagtttc tttatccata ctactaatca    2400
ccaacgtttg ggtggtttcc agcttctgac tgctatgaac gttctcactc ttgctttta    2460 tggccatttg cactaatttt tcttggcata aacctaagag tagaattgct gaatgagagg    2520
acagacgtgt gtccagcttt actaagggtg ccagattgtt cgccacaggc ggctgcactg    2580
ttcttgtcct ccactagcag ttcaggagtt catttccttc atgtcctccc agcagtttta    2640
cgaatttcct gttcaaattt tgtctttttt ttcctttcag ttgagtcatt gctctttatt    2700
gatctgtagt tcttcacat attttgatta ctagttcgtt gtctgatatg tgtcttctga    2760
tgatcttttc ccagtccatg gtttacatct tttactctct cagtgaagtt cttaattttc    2820
atgaaatcca attggtgggt cttttactgc aagcattttt tgctttttt tttttttgaa    2880 aaatcttcat ttacccacag tcatgcagat attctcctgt atttcttcca gagcttgatt    2940
aattaattga tttaatctat tacataaggt acacagtcca ccttgaattg ttttcttgtg    3000
tggtaggata taggaatcag gtttatttcc cccatgtgaa taaaggaaga ttatgagggc    3060
tttcccctct ttaacatatt ttcctatttg aactttaaag tcggcagata ttacttttgc    3120
aatctgaaca aaatgtattt tcttaaaaca tacaggagaa ctatatgggg aggaagacat    3180
aggggtcagc cgggcttccc tgcccttcag ggatgaggaa gtgagaaggc ctagtgagaa    3240
ctcctggttc atccaggagt gaaccatcct ggttcatgcc tgctgtgctc tgattttcag    3300
gaaaggccat ccagctgaga ggcctttgaa cttgcactgt ggcccagggt gagaatgcta    3360
ctggggcatg catgggggc aactggtctg gtggtactc tggtccccct ggatagctgg    3420
ggaactgaag cagagtgtta gagttctgca tggagagtcc cccaggggt atcacagttg    3480 gtgagcactg tccctctgca ggcctccag cctggtggga actgtggcct cttatggcct    3540
cttgggagtg ggaaagggtg cctgacctgc atctttaatg agcatcctct cctgcaggac    3600
aagcttgttg cccacagatg cccctctct acctaaagga gcagcaggcc cagccccaa    3660 gcccagtgtg aggtggcaga gatggcactg agccagagc catcgagcag gttcctggtg    3720
ccggctacaa tgggcagcgc catgcccgag ctgcctggtg ccccaatgc gtccctcaac    3780 agctcgttgg ctagcccgac ggagcccaac tccctggaag acctggtggc cacgggcacc    3840
atcggggtgg tgctctcggc catgggtgtg gtaggcatgg caggcaaygt gtacacgctg    3900
acggtcatgt gccgcttcct gcacacctct gcctccatgt acgtctaygt catcaacctg    3960
gcgctggcag acctcctcta cctgctcagc atccccttca ttgtagctac ctacgtcacc    4020
aagaggtggc acttyggcga cgtgggctgc cgcgtcctct tcagcctgga cttcctgacc    4080
atgcacgcca gcatcttcac cctgaccctc atgagcaggg agcgctatgc cgccgtggtg    4140
aggccgctgg acacggtgca gcgttccaag ggctatcgta aggtcctggc rctgggcacg    4200
```

-continued

```
tggctgctgg cactgctgct ggcactgccc atgatgctgg ccatccggct ggtccgcagg    4260
ggccacaaga gyctctgcct gccrgcctgg ggccagcgca cccaccgcgc ctacctgacg    4320
ctgctcttcg ggaccagcat cgtgggccc ggtgtggtca tcgggctgct ctacgtccgc    4380
ctggcccggg cctactggct gtcgcagcgg gcctccttca cgcagacgcg gcggctgccc    4440
aaccccaggg tgctctacct catcctgggc atcgtgctgc tcttctgggc ctgcttcctg    4500
cccttctggc tgtggcagct ccttgcccag taccgtgggg ccccaccgct cgctccccgc    4560
tccgcccgca tcgtcaatta cctgaccacc tgcctcacct atggcaacag ctgtgtgaac    4620
cccttcctct acacgctgct caccaagaac taccgtgact accgccaacg ctcrctccac    4680
agcaggggca ccagtgggcc tgtgggcgtc cgcagcttcc cacagggcca caccegctgc    4740 cagctcggct cgggtcgctc cgtgacctcc agcagccagc aagccactga gaccatcgca    4800
ytgtcccagg cggtccccgg gagtctctgc gtctgagcgt ccccagcctc cctgtgggcc    4860 ctggggtag gctgtgggga gtggcccctg gagcccaggt ctctcctsga ccaccctccc    4920
cacggtctgc ctcccttccc cagtcctctt ccagaaagct cctggctctc cctcaccct    4980 cactcacttc agctccatca gtgcagctac tttcctcata cgccaagaa gtgccccaa    5040 cccagtccat ctgtgagggt ctgcaggagg ctcrggctca gggccagctc ctgaagaccg    5100
tggtgagtgg agtcttcacc agcccctgc agaygtgact gcgtacctga cgcacracag    5160
grtacaccgt ggcaggtgac accatgttgc cacacaagct gcctgtgtgg gaccctcctc    5220
ctggcatgag cgtggcccca gtggcaccca tttctcccaa ctgccatgtg gttccatccc    5280
gcacagcttc agcacctgga acaataaacg ctgagctccc tgagtcttgt ctgcaacagc    5340
agtgtgagtg gggtgtcaaa ggaggcagga cccccaggac gtcctcctgc acttggagga    5400
gcccatctgc ctgaccgggc aggggacatg tctggccatt aggccttcct gacatggtgg    5460
gtgggtgcca tctggcctga ccaggcccct gggtgtgggg cctgagaccc tggggtgagt    5520
gaggcgggga gccaccagcc tcaacctgct caggg                              5555
```

<210> SEQ ID NO 4  
<211> LENGTH: 13  
<212> TYPE: DNA  
<213> ORGANISM: Artificial Sequence  
<220> FEATURE:  
<223> OTHER INFORMATION: synthetic primer

<400> SEQUENCE: 4
tctgtagcga cgg                                                       13

<210> SEQ ID NO 5  
<211> LENGTH: 13  
<212> TYPE: DNA  
<213> ORGANISM: Artificial Sequence  
<220> FEATURE:  
<223> OTHER INFORMATION: synthetic primer

<400> SEQUENCE: 5
ctcacgatcg taa                                                       13

<210> SEQ ID NO 6  
<211> LENGTH: 25  
<212> TYPE: DNA  
<213> ORGANISM: Artificial Sequence  
<220> FEATURE:  
<223> OTHER INFORMATION: synthetic primer

<400> SEQUENCE: 6

```
gccttgagat tgaattttg ctgtg                                          25

<210> SEQ ID NO 7
<211> LENGTH: 25
<212> TYPE: DNA
<213> ORGANISM: Artificial Sequence
<220> FEATURE:
<223> OTHER INFORMATION: synthetic primer

<400> SEQUENCE: 7
aaatttactg tcttgttgcc tagtg                                          25

<210> SEQ ID NO 8
<211> LENGTH: 25
<212> TYPE: DNA
<213> ORGANISM: Artificial Sequence
<220> FEATURE:
<223> OTHER INFORMATION: synthetic primer

<400> SEQUENCE: 8
ttttgtacac taggcaacaa gacag                                          25

<210> SEQ ID NO 9
<211> LENGTH: 26
<212> TYPE: DNA
<213> ORGANISM: Artificial Sequence
<220> FEATURE:
<223> OTHER INFORMATION: synthetic primer

<400> SEQUENCE: 9
tgagacatgc cttaagaatc ctcaga                                         26

<210> SEQ ID NO 10
<211> LENGTH: 26
<212> TYPE: DNA
<213> ORGANISM: Artificial Sequence
<220> FEATURE:
<223> OTHER INFORMATION: synthetic primer

<400> SEQUENCE: 10
gggatgatat gaggtcatag gataat                                         26

<210> SEQ ID NO 11
<211> LENGTH: 23
<212> TYPE: DNA
<213> ORGANISM: Artificial Sequence
<220> FEATURE:
<223> OTHER INFORMATION: synthetic primer

<400> SEQUENCE: 11
tctgagacat gccttaagaa tcc                                            23

<210> SEQ ID NO 12
<211> LENGTH: 23
<212> TYPE: DNA
<213> ORGANISM: Artificial Sequence
<220> FEATURE:
<223> OTHER INFORMATION: synthetic primer

<400> SEQUENCE: 12
ctcctccagg ggatcttctc aac                                            23

<210> SEQ ID NO 13
<211> LENGTH: 24
<212> TYPE: DNA
<213> ORGANISM: Artificial Sequence
```

```
<220> FEATURE:
<223> OTHER INFORMATION: synthetic primer

<400> SEQUENCE: 13
taatgctctt cttccctccc cttg                                              24

<210> SEQ ID NO 14
<211> LENGTH: 24
<212> TYPE: DNA
<213> ORGANISM: Artificial Sequence
<220> FEATURE:
<223> OTHER INFORMATION: synthetic primer

<400> SEQUENCE: 14
tttgtgaact ctgggggcta gaaa                                              24

<210> SEQ ID NO 15
<211> LENGTH: 24
<212> TYPE: DNA
<213> ORGANISM: Artificial Sequence
<220> FEATURE:
<223> OTHER INFORMATION: synthetic primer

<400> SEQUENCE: 15
ggtccttgga cccagtgaag ataa                                              24

<210> SEQ ID NO 16
<211> LENGTH: 24
<212> TYPE: DNA
<213> ORGANISM: Artificial Sequence
<220> FEATURE:
<223> OTHER INFORMATION: synthetic primer

<400> SEQUENCE: 16
atcccatgaa acagcaagaa aacc                                              24

<210> SEQ ID NO 17
<211> LENGTH: 26
<212> TYPE: DNA
<213> ORGANISM: Artificial Sequence
<220> FEATURE:
<223> OTHER INFORMATION: synthetic primer

<400> SEQUENCE: 17
caaccactca tagtatctgc aaaaca                                            26

<210> SEQ ID NO 18
<211> LENGTH: 24
<212> TYPE: DNA
<213> ORGANISM: Artificial Sequence
<220> FEATURE:
<223> OTHER INFORMATION: synthetic primer

<400> SEQUENCE: 18
agtcaccatc accaaaatca tcca                                              24

<210> SEQ ID NO 19
<211> LENGTH: 24
<212> TYPE: DNA
<213> ORGANISM: Artificial Sequence
<220> FEATURE:
<223> OTHER INFORMATION: synthetic primer

<400> SEQUENCE: 19
cggactcgga ttcagattgt cagt                                              24
```

<210> SEQ ID NO 20
<211> LENGTH: 24
<212> TYPE: DNA
<213> ORGANISM: Artificial Sequence
<220> FEATURE:
<223> OTHER INFORMATION: synthetic primer

<400> SEQUENCE: 20
gagaggcctt tgaacttgca ctgt                                    24

<210> SEQ ID NO 21
<211> LENGTH: 24
<212> TYPE: DNA
<213> ORGANISM: Artificial Sequence
<220> FEATURE:
<223> OTHER INFORMATION: synthetic primer

<400> SEQUENCE: 21
tagacgtaca tggaggcaga ggtg                                    24

<210> SEQ ID NO 22
<211> LENGTH: 20
<212> TYPE: DNA
<213> ORGANISM: Artificial Sequence
<220> FEATURE:
<223> OTHER INFORMATION: synthetic primer

<400> SEQUENCE: 22
ggcatggcag gcaatgtgta                                         20

<210> SEQ ID NO 23
<211> LENGTH: 23
<212> TYPE: DNA
<213> ORGANISM: Artificial Sequence
<220> FEATURE:
<223> OTHER INFORMATION: synthetic primer

<400> SEQUENCE: 23
atgcccagga tgaggtagag cac                                     23

<210> SEQ ID NO 24
<211> LENGTH: 21
<212> TYPE: DNA
<213> ORGANISM: Artificial Sequence
<220> FEATURE:
<223> OTHER INFORMATION: synthetic primer

<400> SEQUENCE: 24
gtggtcatcg ggctgctcta c                                       21

<210> SEQ ID NO 25
<211> LENGTH: 20
<212> TYPE: DNA
<213> ORGANISM: Artificial Sequence
<220> FEATURE:
<223> OTHER INFORMATION: synthetic primer

<400> SEQUENCE: 25
ccactcccca cagcctaccc                                         20

<210> SEQ ID NO 26
<211> LENGTH: 21
<212> TYPE: DNA
<213> ORGANISM: Artificial Sequence
<220> FEATURE:
<223> OTHER INFORMATION: synthetic primer

<400> SEQUENCE: 26

```
cagccagcaa gccactgaga c                                           21

<210> SEQ ID NO 27
<211> LENGTH: 21
<212> TYPE: DNA
<213> ORGANISM: Artificial Sequence
<220> FEATURE:
<223> OTHER INFORMATION: synthetic primer

<400> SEQUENCE: 27
gggtcctgcc tcctttgaca c                                           21

<210> SEQ ID NO 28
<211> LENGTH: 93463
<212> TYPE: DNA
<213> ORGANISM: Bos taurus

<400> SEQUENCE: 28
cagcagaggt gcctccatta gtttggaggc ccaggccccc ctccccactg ctgttttcag   60
gggtggggct gaaggacccc acaaaggtgg ggccctgagc ttctggtttc caaggaggc  120
aggaaggagc gtgatggcca tgctgagggg agtggtgcct ctgtactctg ctccctggac  180
agaatcagga gttagagccc acggagaatg tgaggacgtg gccttggctg tcctgctttt  240
aggacagaac tggaggccct gggtttcta tccatctcct gcaccaactc ccattttgcc  300
atccccataa gggcgctcgg ggcctctgca tccagccttt tcactcagaa tacacagtat  360
gaaactgtgt attcatggat tctgaactgg ggcccttttc acaggctac caggcctgaa  420
tggcccctg gacctggga ggcagcagcg ccggacctgc agcacctctc ctctaggcag  480
aagtgccaca gggctcccct aggggcccca gtgtcaacag tgagagagac agtgttgtgt  540
gtacttgaca tttctcttcc ctctccctgc atccagcttt cccaaacccg aatatttata  600
gtcgggacct ctctgaactc tcatgagttc agtcacctgg actgctcaga tgctggaggc  660
tctctgctag tctacagggg cccgcctcca gctggagacc tggacaggtt ttaattggtt  720
tgattgcaat cctcatccct ccagctgggt ctcagatctt gagtatttga dacaaggatt  780
ggggaaattg tttctgaaat tgaaatcaag taacaacatt agcagcggca tcaagggaag  840
aatctcctgg aaaacagtta gctactgact gcagaagggc cctaagctgg ggagggaca  900
gccaagcagg tgtgtccctt ctgggacctc cttctggggc atgggccccc cggctgggcc  960
ctagacagtc tctgtcagtg actggtgagg ctatgtgggc catttctgcc caactctgga 1020
ctccttccac tctgctctcc tgaaggggct ggcctagact cttacaggtg cactgaggcc 1080
tgttttccct ccaccccag tcctactccc ttccctttct ctttccaagg catttttta  1140
ggggctgggg ggacaggaca gtgacaagat gtgcctctga caagtctgtg atcaggctgg 1200
gtgggcacct gtgaagagac cccacgaagc cagattcagc ctatggcatc tcatcttcca 1260
cctaatttag taatccagtt ggaaaagagt tcttgcagaa aaatgatcat ttaaaaatat 1320
aatgaaccca ttatatgaag agcaaagctt taaagtcaca tttgtggaaa gtgggagctt 1380
tataattatg atttatgatt taatggtcca taaaatgaat cagagacagg cttagtcatg 1440
cgactctttg tgaccccata gactataact tgccaggctc ctctgtccag ggaattcgcc 1500
aggcaagaat actggagtgg gtagccattc ccttctccag gacatcttcc cgacccaggg 1560
atcaaacctg ggtctcctgc gttgcaggaa gatttcttac tatctgagcc accagggaag 1620
ccccattaaa tgcagagcaa agtttaaagt cacatttgtg gaaagtggga gctttatgat 1680
tatgatttaa tggtccataa agtgaatcag agacaggcag agtttagttt gcaaagaaca 1740
```

```
cagtagatct tagggatgtg gtccactaac ccgaggacag cagcaccatc tccctgaagg    1800
atcctggccc tctttcctca agccccaagc cctgaccact ggagccattc gggtcctctc    1860
aggtccaggt taaggacagt gcaatagagg aagagtttca gataatctcc ctgatgatgt    1920
cccttgagag gacatatcag ccaccagcac cttcaggtct cccagagagg aggccatggg    1980
ctgtgtggcc tgtggctctg caggacgtcg tgaccaggag atgagaccaa ggctgctctg    2040
agatggggag ggagctgacc aacacctaaa cagatgctgt ccttgatcat ccatatttcc    2100
cagcctgcag ccctgagggc ctatgtcaag ccaggttgct cagtgacccc agcagctaac    2160
cctggtggtg ttcctggaag cttctctctg tgacctgggc atgcccttgg tcacagggtg    2220
tttggaccaa aggcagcaga tgagcctgaa caccatgagg ccgaccagcc tgaatcacct    2280
gcccacagga caggaggatg agaggaagac ctgcctatga gtctacctgt ccaagagaag    2340
cagtggggta actcaagcac acccccatgc caggggcctc caggctcagg gacaatgagg    2400
agtggagagc agtactctga gggccccagg gctcctaaaa acagagtcat ctggaaaaaa    2460
tctgacaact aaggacagtt aggatttttc aaagaaataa aggaaggacc atgacgcatg    2520
aaaggaacag aaaattataa atcaaaatat tcatagcagc actagtcacc atcaccaaaa    2580
tcatccatca gggatgaagg gaaaaacaaa gtgatttacc ttgaatcaga agatattctt    2640
cagggcgctt ccctggtggt ccagtggcta agaccctatg ctcccggtgc aggggcctc    2700 ggttcaatcc ctggtcgggg aactagatcc cacatggtgc aactaagacc tggcccagcc    2760
aaataaataa atacattaaa agaagaaaaa gaagatagtc ttcagtcttc tgaatacttc    2820
actcttctgt cttcacagaa tactcttcag tcttgaaaag gatggaaact cttacccttg    2880
ctacaacatg aaggaagctc aaagacatca tagtaagtga aagaagccag acactaaggg    2940
acgaatgtat gatcccactc acagcgggtc cttagagtag tggaatccat ggagaccaaa    3000
ggagaatggt ggttgtcagg ggctggggga atggatgtg gagttgtcta atggggacaa    3060
taaaaggttt gtgttgataa aaggttttgg aaatagtgac gagtgcacat tatgaatgtc    3120
tttaatgaca ctgggtcctg gcctcgcatg ggtctctcag aaccaccctc cacccactgc    3180
gtcccccaca ggtgcagagg agggtccagg gcttgactga caatctgaat ccgagtccga    3240
ggctcagtgc ttgggaaact gaggggtggt ggagtgcaga gggcgaaggg aagcagagac    3300
gctccgcggt ggggccagcc aggctggact gagcttcacc ccatggatgc gtctggagtc    3360
ccagctgcgc cgtgatctgc cctctcgctt tgccacccc cgctcccgcc cctgctgccc    3420
tcccgtccct gggcctccgt ggctcccccc accgcagcgc atcctcgccc cctctctagc    3480 agccccctc ccgcgggtta ttaatatccg ggccgggcgc agggccgccg cgcattccca    3540
gctggcagcc gggcaggtgg cgccggcgac aggggcctgg gcgcggaacg cggctctcca    3600
ggcgagaccg gcgggcgggc tccctccac cacgcgcccc tggagcccc cacgtcctct    3660 gcgcgcccct accgggcaga gccctcggaa aggttcccgt gccgcgccga gtgtttggag    3720
acgcttagcg actaagcgcc ggtccagagc acgaccccag ggtgctcggc gcccacacct    3780 gacgccggt gacggaggtg ggcgcaggca ctgcgagggt gcgggcggg agaagggcc    3840 gggatcctcc cggggcgggg cgccctcccc gctggcccgc acaatcccct gcaggatcgc    3900
tcggccacga agccctccca gcggaccccc gggagatgcg tggcgcttcg gagggtggag    3960
agggtgaggt gtgcgcggtg ggctcggcgg ctgtttcgcg tccctcccgg gaggtcctcc    4020
gccaggttcg cggtagcccc tgcggagggg ctctggaacc agaacccact gggggctgcg    4080
gccgcggagg gcgcctcggg ccggtaggaa agaccccagc tcccctcgcc agacccaagg    4140
```

```
ctgagccaag tcccacgggc agggggccta ggacagcgtc tctacaccca gcttgccctt     4200
ctgcaccgag tgctcagttg gacgccccga gtttatccat gttagtgcga acgctgtacc     4260
tgtagaggga aaaaaccggg aaccagtttt atccggccac attatcccta gatgtgggga     4320
gattgggcca taaaggggcc tctcctctca ttcaagtatt caggttttag gtctcttttt     4380
tctcatgagg gtaattttca cccagtaagc acgggtcatg agtgtgcaac tccaggagtt     4440
tttacatgtc cgtagtcgct aagtcgtgtc tgactctttg ggaccccatg gaatgcatag     4500
cccgccagac tcctctgtcc atggggagaa tgctggagtg cgttgccatg ccctccttca     4560
ggggatcttc ccaacccagg gatcaaaccc aggtctcctg cattgcaggc ggattcttta     4620
ccatctgagc caccagaaca cctgtgtaac cagtgccaca tgaggacata gcacacgtcc     4680
gtcccggagt gctctccggt gcccctacc agttgacacc ctcttcaacc actcatagag      4740
attttttctt ttccccagct tcattcaggt aaagggaatt atacagtgtg tacttttttgt    4800 gtatggtttc tgtttcatcc ccccccccc ccccactcaa cagagcatat ttgagtttca      4860
tcaagttgct gactgttcaa taatttcatt ttcttcatca ccttggagca ttttttattgg    4920 ggggggggtg tcagtttctt tatccatact actaatcacc aacgtttggg tggtttccag     4980
cttctgactg ctatgaacgt tctcactctt gcttttatg gccatttgca ctaattttc       5040 ttggcataaa cctaagagta gaattgctga atgagaggac agacgtgtgt ccagctttac     5100
taagggtgcc agattgttcg ccacaggcgg ctgcactgtt cttgtcctcc actagcagtt     5160
caggagttca tttccttcat gtcctcccag cagttttacg aatttcctgt tcaaattttg     5220 tcttttttt cctttcagtt gagtcattgc tctttattga tctgtagttc tttcacatat      5280
tttgattact agttcgttgt ctgatatgtg tcttctgatg atcttttccc agtccatggt     5340
ttacatcttt tactctctca gtgaagttct taattttcat gaaatccaat tggtgggtct     5400
tttactgcaa gcattttttg cttttttttt tttttgaaaa atcttcatttt acccacagtc    5460 atgcagatat tctcctgtat ttcttccaga gcttgattaa ttaattgatt taatctatta    5520
cataaggtac acagtccacc ttgaattgtt ttcttgtgtg gtaggatata ggaatcaggt     5580
ttatttcccc catgtgaata aaggaagatt atgagggctt tcccctcttt aacatatttt     5640
cctatttgaa ctttaaagtc ggcagatatt acttttgcaa tctgaacaaa atgtattttc     5700
ttaaaacata caggagaact atatggggag gaagacatag gggtcagccg ggcttccctg     5760
cccttcaggg atgaggaagt gagaaggcct agtgagaact cctggttcat ccaggagtga     5820
accatcctgg ttcatgcctg ctgtgctctg attttcagga aaggccatcc agctgagagg     5880
cctttgaact tgcactgtgg cccagggtga gaatgctact ggggcatgca tgggggcaa      5940 ctggtctggg tggtactctg gtcccctgg atagctgggg aactgaagca gagtgttaga     6000
gttctgcatg gagagtcccc caggggtat cacagttggt gagcactgtc cctctgcagg     6060
cctcccagcc tggtgggaac tgtggcctct tatggcctct tgggagtggg aaagggtgcc    6120
tgacctgcat ctttaatgag catcctctcc tgcaggacaa gcttgttgcc cacagatgcc    6180
ccctctctac ctaaaggagc agcaggcccc agcccaagc ccagtgtgag gtggcagaga     6240
tggcactgag cccagagcca tcgagcaggt tcctggtgcc ggctacaatg ggcagcgcca    6300
tgcccgagct gcctggtgcc cccaatgcgt ccctcaacag ctcgttggct agcccgacgg     6360
agcccaactc cctggaagac ctggtggcca cgggcaccat cggggtggtg ctctcggcca    6420
tgggtgtggt aggcatggca ggcaatgtgt acacgcgac ggtcatgtgc cgcttcctgc     6480
acacctctgc ctccatgtac gtctacgtca tcaacctggc gctggcagac tcctctacc    6540
```

```
tgctcagcat ccccttcatt gtagctacct acgtcaccaa gaggtggcac tttggcgacg   6600
tgggctgccg cgtcctcttc agcctggact tcctgaccat gcacgccagc atcttcaccc   6660
tgaccctcat gagcagggag cgctatgccg ccgtggtgag gccgctggac acggtgcagc   6720
gttccaaggg ctatcgtaag gtcctggcgc tgggcacgtg gctgctggca ctgctgctgg   6780
cactgcccat gatgctggcc atccggctgg tccgcagggg ccacaagagt ctctgcctgc   6840
cagcctgggg ccagcgcacc caccgcgcct acctgacgct gctcttcggg accagcatcg   6900
tggggcccgg tgtggtcatc gggctgctct acgtccgcct ggcccgggcc tactggctgt   6960
cgcagcgggc ctccttcacg cagacgcggc ggctgcccaa ccccagggtg ctctacctca   7020
tcctgggcat cgtgctgctc ttctgggcct gcttcctgcc cttctggctg tggcagctcc   7080
ttgcccagta ccgtggggcc ccaccgctcg ctccccgctc cgcccgcatc gtcaattacc   7140
tgaccacctg cctcacctat ggcaacagct gtgtgaaccc cttcctctac acgctgctca   7200
ccaagaacta ccgtgactac cgccaacgct cgctccacag caggggcacc agtgggcctg   7260
tgggcgtccg cagcttccca cagggccaca cccgctgcca gctcggctcg ggtcgctccg   7320
tgacctccag cagccagcaa gccactgaga ccatcgcact gtcccaggcg gtccccggga   7380
gtctctgcgt ctgagcgtcc ccagcctccc tgtgggccct ggggtaggc tgtggggagt   7440 ggcccctgga gcccaggtct ctcctggacc accctcccca cggtctgcct cccttcccca   7500
gtcctcttcc agaaagctcc tggctctccc tcaccctca ctcacttcag ctccatcagt   7560
gcagctactt tcctcataac gccaagaagt gcccccaacc cagtccatct gtgagggtct   7620
gcaggaggct caggctcagg gccagctcct gaagaccgtg gtgagtggag tcttcaccag   7680 cccccctgcag acgtgactgc gtacctgacg cacgacaggg tacaccgtgg caggtgacac   7740
catgttgcca cacaagctgc ctgtgtggga ccctcctcct ggcatgagcg tggccccagt   7800
ggcacccatt tctcccaact gccatgtggt tccatcccgc acagcttcag cacctggaac   7860
aataaacgct gagctccctg agtcttgtct gcaacagcag tgtgagtggg gtgtcaaagg   7920
aggcaggacc cccaggacgt cctcctgcac ttggaggagc ccatctgcct gacccgggcag   7980 gggacatgtc tggccattag gccttcctga catggtgggt gggtgccatc tggcctgagc   8040
caggccctgg gtgtggggcc tgagaccctg gggtgagtga ggcggggagc caccagcctc   8100
aacctgctca gggaggacag gcggctggga catcactcca gggcaggaac ttggagccca   8160
aactaaaatc atgagccaga attactctcc catttgcagc tcacctgcct ctccctcccc   8220
agaccttgag gggatggtgg gggtggatca tatacaacgc agtaggggat tatctcatgc   8280
ctcctgtgta cagcatccca gttggacctc ctatggacac caagaccatc aggccctgcc   8340
cacagagagc ccacccacag ggaaaggttt tggacctacc ccaaccccta tcccactctc   8400
cggtgaccag ttcactccac actgtacccc taattcacat cccaacctgg ccccagcca   8460 tggctgcaca cacatcagat tcaaggcctt gactggatcc taatgtgttg gcaggtggag   8520
atctggccgc taagtatgga gtgggaggct actggcccca cctgggaccc caatgttttt   8580
gggaagaaaa cagcccaaag tttgtacctt gatcaaggcc ccatgtctct gtttcctgaa   8640
tcctaattcc agaatgcacc cagaaggccc caaacttgga aaacagagac cctcccctac   8700
cccgagtgtc cctgcaatcc ccattcatct gcacatgtga aggtgctctt tgcactattt   8760
cttggcatga tactgaagaa cttacctttt tggccccaaa tttaagacct gagtaccctg   8820
gttagtgctc ccacatgggc tggctgagct tctactgcca ggcctgggac agctgcaggg   8880
gctgtcttcc cacctcccac ttagaagtgc tcccacactc ctgccagcct ctggggagcc   8940
```

```
tcatgataac accgtgagtg tttcagagtg cttaaaaatg tccagcaggc tctcatgcct    9000
gtgtactcac acacacagcc acgtggagac tcctactggc ctactacagc ttggccaacc    9060
tccctggacc caccgcccac agtccctccc tctcccctca ccacaggccc ccaggaccca    9120
acagtcaggg accggtgatt tatggaggcc tggtctggct caagacccac agtcagcagc    9180
ccatcaggca tggtgcctgg cccttggcaa gccggagagc agagagccct ggggtgaggg    9240
gccaaccggg gtgagcttgt gtgtggctag aatagggctc tagaatagca ggtcagggct    9300
cctgttcaaa tgctacagct ttattggggt agtttcacac cataaaactc acccactgaa    9360
aatacaagta atgattttca gtgaaaggac agtcatgtaa ccaacatcac agttcagtct    9420
cggggcatct gttaggccgg gtgtgcgtgc tcagtcgcgt ctgactgtga ccccattgga    9480
ctgtacagcc cgccagtctc ctctgtcctg tcaggcaggg agctccaaag aaatcaacca    9540
atagcacaga cgtataaata ttaaaaggtt ctttgaagga attggcatag tgattaaggg    9600
actggcatgt ctgggatcca ttggcgggtg gggcagcagg ctggcgggct ggaaactcag    9660
ggagaagacg ctgcagcctt ggggcagaat tccttctttc ccagaaacct ccgttttttgc   9720 tggaagaact ttaagcgcct ggagaagccc cacccaccat gttccgggaa cagacgccct    9780
tctgtagtgt gggcagagct gaatgtgccc ccgtggatga acacgtgttg gttgtgggca    9840
tttgaggtgc ttccaccttt tccctaaatg aacaggccca ccgtgaccac ccgtgtggcc    9900
atgcggctgc caccccctcca gccgccctgc atgagggctc ctggtctcct ggcttctcca    9960
tcctgcccac cctgccctcg ctctgggcag gcaccgtttt atgacaaaag agcagctgtt    10020
ctgggtaaac tcggattcga aacaggtggc tctgtgatgg cgaccgtctc tcagagtcac    10080
gcgtctgcag ggctggggcc ctaggccttg ctcaatgggt ggtggcaggc tggtgggggc    10140
aggggcaccc ccttcccatc cgcatcacct tggcttccaa caggagtgag tccaggcttc    10200
cttacctcca gctctgtccc aggaacctgg ggcgttccca cctggtaatg tgtaccgagg    10260
gaggggcagc cggcagggcc cctcagaagg agacatcgtc atggccacct tcactgtgga    10320
ttgtcctggt tctacgggtc atctgaaccc ttatgaccag tttcccatgt ccccagaaag    10380
gcactggata ggtcaccacc ctatccccac aacctgggga aggccctgac caggtctcct    10440 gtccctgtc cccagaaaga cactgaccag gcacatccac aggcctcaca tcctgctggg     10500 aggctgggggc ttctccaagt gctgagtatt ttccaatagt tcagaggcag ggaggagggc   10560
ttcgaaccca gggtttgctc tgcaaattgc cttgtgttat ctggggctta agaccacagg    10620
gctttgctgg agatctggtg gtgtggacac catgggaggc agtgtggatg ccatgggagc    10680
aggtcatagg gaacagagcc agcgaagccc caaagggatg ttcacccctg ggcgctgggg    10740
cactctgacg ttaaccccca cacaccccaa ccaccgttgg ggcctgtggt gaggggcctt    10800
gtcctgcagg gccctccctg gggtgggctg ctccctgcct gcctcctgtc ccttccctgc    10860
ctgccccaga atctcaggcc cccacagggg ccactgggcc tgggcctccg ctcaggcatc    10920 cttccccccgt tgtcagggtc cccagtgacc caacagtctt cactgacgt cctgcatgac     10980 agcctctgct cttcctgaac aggggaccac caggctgtgc acggagctgc tttccacgca    11040
accggggaca gagggagcag gacacggggcc accactccag aaaacgggga cagtgtccct   11100
ctccactcta caagcgtcag acccagagct ccggaaacca ggtggaggtc tcacctgggg    11160
ccaccgccct gctgggcaga ggggccagta gtgggtgtgg aaaagggagg tgggagggag    11220
ggaggagcga aggggatgga tggaggaaga gaggaggagg aggggatggg ggagagagga    11280 gtgggaggggg gtggaagtga gtagggagga tgggaggtgc agcgagtgct cctctcccac    11340
```

```
agcacagtat gtcaggagct aagaggacct gctgtctgag tccagcccag gcctccaggg    11400
cagtggtggt tagcggtggg gatgagcagg ctgtcgactg tctgatggat gagcattcag    11460
gctgaaggtc actcagggtg atggatgagg tctcggcatt taaatgccag acacccaacc    11520
tccagacttg cagatgagga ggcaaaacac caaggccagg ctcagcccac agtgctcttg    11580
acagcttaca aagcaccatt acactgactt gggtccctga ccactgccca ggaccacccc    11640
cagcccccac cctgcatcgg gggaatgaat ttcttttcag agaagattgc tgggatccct    11700
ctgtgagaca ctaactgtgc tccaatgaaa tgttttgtga atatggatt tgttccagcg     11760 gggctcccat gaatctgggt taatagggta cgggctggat ggggaggtct ttgctgggggt   11820 tggtgcgtga agctcctcta gaagaccttg ggcacagagc catggggact gggtgcccaa    11880
ctgcatcagg gccaggccta tgggcatgtc tccccatccc atcctcaccc cctgcaccct    11940 cttcctgag ttttcccacc ccactccccg cagttcctat agcgaaaaca aggagcgggg      12000
acagtgatca ggcaggctgt ggggcctgtg actaggacag tggtggctgg cacccactgg    12060
ggaatgaatg aatgtatgaa tggacaaact gtgtccctct gctagggacc tgctgccctt    12120
ccatattctg tcctctgtct tcctggagat ggtgagggg gaaggaacc agggccggat      12180 gagtgcacag ccgagttcac agccaagctc gcaggaggca ggggcatcca ggagcctagt    12240
ggtggaggct cgggtgatgg atttaccagg tgcaggcaca ttcctgcccc acaggccgga    12300
cagtttccaa gaggctcagc cttggccagg atttggttgc tgacccgcag gcttttcag     12360 acccaggaga gtggcctgtc ccagtccaca aacttgtgcc ctgagtcccg ccctccaatc    12420
tcccgtgggt ccccaggggt gggaggcaga gaaagcccag ctctcgcacc agcacacaga    12480
gtgcccgagt cgccggctgc aggcccaaga ccgcgcactt ggtgtaaatt tctcatcaac    12540
aaagaaacac acacagtcca aagtttccgc tattcctaat ttttttcagga actcattttt    12600 tgggaatcag gttgcaccta caaccagtag acaccgctgt ttacctgccc agggagctct    12660
ctctgctttt gtagaccatc cttatcaaat ggagttcggg ggtgggcagt accagcgaca    12720
gtggccctgc ctggtagggt ggcccagcca atttgtagag acctgaactc tgacctgatt    12780
ccatgcctga acacgcccac ctgaagggcc aggcttgggg ggcagaatgc tggggctcct    12840
ttccatcctg gagaaagccc tcagctcaca ggcacctcca cttacatacc caccaggcaa    12900
gacaggaggg acctcagtta gcagaagggg agagctccca ccccaggcag gaggtaggga    12960
tggccagagt ctagcctggg ccctatacac tcacagacca ccaaactggg aatctgagag    13020
ccccagggcc acctgcagga gcaggttttt ccattggcat tccagacaga tgacgctctg    13080
agcaggaaga ccgagaggct gccaacagcc agcagccaag agtaccagac tcctgccttt    13140
cccaggctgg ccgagggccc aggcccatgc agggggtggg gtgggggtt ctcctggggc     13200 caagctagga gagccccatc ccctgagctg cccaggcgg gccccaggc gggatggctc      13260 tgtcttgcca ccttttcccct cctggagctg tggagacgga ggcctggtgg gcctgagtgc   13320
tgagcgggat cagagccagg aggcagctgg gtgttctgcg gcccaggaac tccagtccac    13380
ccctctgccc ttcctccatg tgcaaattcc ttggccccc aggagggccc ctcaacaagc     13440
tcaccattgg gtcatctttt gtttttacaa aattctcttt attcccactt cacagctgag    13500
gaaccaggcc acgcgggacc cacaaggagc caggagcacc cattctcagc tcagtgggtc    13560
tattcccctt tgcccttcat ggcctgaggc accccgcagt gtgattgaaa gcccagagcc    13620
tgatctcaac ccaaaactgt gtgtcagtgt gaaatgccga ggctgcctgg gcatcagagt    13680
tggctgcccc gtgccaagat tcttctccag ggctgtgacg agttgaggcc aggcctgggg    13740
```

```
cctgatgggg gatggggaac ctccatttct gcccttggtc tcccaatgtt ccccactcct   13800
cccctcatcc tgcgtcctcc ccaagcgtcg gcagagctag gatggaccgt gtgtaccca    13860
caatacacca ggctggccag cgggcagctg aagcccggga gacgcggcca ggaggtagtc   13920
ctggtgcatg aatgactaca gggatggggg aggtgctaaa ggagtaacgt gagcctgcat   13980
ccccacctgt gacagatatg ggagggccgc ctgagctgac agtgaagttg gggtgccagc   14040
tggggtctcc tgggcaggtc ctgaacccag ctgagggtc caaatccccc tatgaggggt    14100
ctgtgcctga agcctggccc caggaggcaa gacccacaca ccatgaatgc aaggcctcag   14160
cgagggttcc gaggagctgg tgggcatgga gggcggggt ccccaggaaa cagcgacccc    14220
accccaccc tgcactgtcc tcacagagac acaggcacag gagaacatgc gatagggccc    14280
gcatgggtc tcattgataa gacggctcat tatgtcagcc tcacaaagaa taaatcacag    14340
tgatccgtga gactgaccaa attgcccaaa cggcatcctg ttatctcact ggcacctatc   14400
ttctcagagc tgcaagacca ccagattcca gacatctggc tatgtgacca tcccttcaga   14460
gaattttca ctggtggggt ataagaagga ctccgtcaga aagagagaac actggttctc    14520
cttaagagco agtcaccctc tctcttccct ctaataaatt tccttttctt gcctgactat   14580
cccgctcact ctcttttct ctgcgctcac cttacaacac ccactgctcg gcccctactc    14640
cctgccacat cccctccacc ccacaaacct tgctagtgcc tcagagtccc tacagggcag   14700
ggggaggggc aggtttggct atgtggggtg ggcagggagg gcgttggggg ctggcgactc   14760
tgggagcagg cagcaggtat aagcacacg cccgctttct cctgggaagg aggtcttggt    14820
ccaggaccca ccctgggtgt gcagagaccc tggacagcgt ccacccacca ccccttcctc   14880
tcccttcccc tcctcctcct ccctgttcac cagaattttt caggaatgag gtccttcctg   14940
agtgttcccc agctgtctgt tctttatcaa ggggaatgag aggagatgag tgagttcccc   15000
ccatgtctag gaaacccagg gacagttggc aggggcaagg ggctcaagct gggcacctgg   15060
ccaggtgtgt ggccacagca agattctaag ccccccgcctt ctgggtccac tgggatagag   15120
gttagtagcc atgaccccca agctgcaggt gggactggtg tccctgatgg cctcaggaag   15180
ggggcctgc accccaggt ccactgggat ctgcttggcc tcaaaggtgc tgagatggaa    15240
ggaacatcaa gatgggccca cagatctgca ggagatagag cacagccatc caccctggtc   15300
cagacccttc ccactactct gcagggcacg gtgtgctggc caggaggtgg gggttcaggc   15360
ccccaggggt gaacagttac agagggggtaa ctgaggggtg ggaggcgctg ggatggcaga  15420
agcctggagg gtctcctccg gggaggaatg ggggcactac acttctcctg aaactcaaga   15480
tcaagataag aaactggtat ttacatgtca gtgcgtccaa ggagacccca agatgggttg   15540
gatgtggact gaggatgtct ccctcttccc cgggggccacc aggagtctcc agtctgaagt   15600
gtgactgatg tctggttcac tggtattctg ccctgcttgg cctcaatctg ctattccatc   15660
tcatctgctt tcagttcagt tcagttcagt cgctcagtca tgcccgactc tttgtgaccc   15720
catgaattgc agcacaccag gcctccctgt ccatcaccaa ctcccggagt tcactcagac   15780
tcacgtccat tgagtcagtg atgccatcca gccatctcat cctctgtcgt ccgcttctcc   15840
tcctgccctc agcatcagag tctttttccaa taagtcaact cttcacatga ggtggccaaa   15900
gtactggagt ttcagcttta gcatcattcc ttccaaagta ttgctttgta atctgtcaat   15960
gtgtctcaga ttgtacacat gctagggat aaaatcttgc tgcccccacc tgctgcccat   16020
cccactccac cacagcccct ccttcctagg ctgagcactg ccaggcccca gagtttggtg   16080
tgactggctt ggtttctgga agaggctgcg tcactgggga ctcacatcac tagagtctta   16140
```

| | | | | |
|---|---|---|---|---|
| ggtccttggt | tgcctagtct | caggggtgag | cagaagtgtc | cccacactcc  tactctctgt | 16200 |
| gaaaacctct | agaaggtgtg | ggaggccctg | agatgctgtg | acttcagaag  gcaaataagc | 16260 |
| cagtacccag | tgggcagggc | agagatgcca | ccaattaggg | ggccggcaat  ggggaccact | 16320 |
| tccctagaca | gcatgagaaa | acccttggca | caagcccata | aggcccaccc  aaggccccac | 16380 |
| agtgcaagcc | cacaaggtgc | cgggagttg  | gtgctgcctg | ggggatgagg  gctgggggg | 16440 |
| acggggtgg  | cttggtccca | gtctcatgtg | aagaccatgc | tggaggggag  aacagggaag | 16500 |
| agaagtggct | ccaggattag | aagatccaga | ctgagaacca | gcatggatcc  caagacccttt | 16560 |
| caaggcgctt | ccagttgtaa | ctcgaagggg | aacaaacaga | ctggtgtttt  gctctggatc | 16620 |
| agccctgaga | tggggtggac | agctgtgag  | atttccgtaa | atcccttatc  cctccagtaa | 16680 |
| cagccctgtg | gccctgcaa  | caaccccctg | aagccacagc | cccctgctct  gcggcgcctg | 16740 |
| cccatgggcc | tcacacaaat | catggggatg | gcacagccac | gtccttcctg  cctgctagtg | 16800 |
| ctgacgcctg | gtcctgccat | ctgttgctgc | cgagcacctt | ccaagcttcc  ccaaacccccg | 16860 |
| agaccctcct | cctcccaggc | tgccctgagg | cccaggcacc | actgcattgg  gtgaggcata | 16920 |
| agctgcacct | gcccacccgg | taagaaggca | gaggcctggc | acagcggaga  tgccaggctg | 16980 |
| tgagaggcaa | agccagcctc | aaggtggaca | caagcgaccc | caccgtccct  gctctggcca | 17040 |
| agcccaactc | tcgcacaatt | ggtggggcca | cacctgcccc | ggaagccctc  cctggcacac | 17100 |
| tgcggccgct | tctgcaatct | cttgcccttt | tctcctgtgc | agggcaggaa  aggtaacttg | 17160 |
| cagctgaggg | aggaaggcca | gctcaggtcc | catcccactg | ggtcagctcc  agacctgacg | 17220 |
| tttcagcttc | aactctcatg | gaggctcagc | cgtgttcagg | cctggccctg  gtggctggct | 17280 |
| cgccagcaga | gccggagtgg | caagcccctc | tttccagcag | tgagaccaat  gctcaccttc | 17340 |
| tttgattcag | acgctaaaca | cttttttaata | ggaaataagt | cactcagcag  agggtatgtc | 17400 |
| gggacccccca | tttctccctg | gaacagacga | ctccacccctc | ggtcaggacc  tccctgcagg | 17460 |
| actgaggagc | tcacgaggcc | ccaggtgagc | actgctgggg | gccacccagc  acgtgcacat | 17520 |
| acatctccgg | ggcttacaca | ttttttcttt | aaatgaagga | catttttgtt  tttgcccaaa | 17580 |
| tcttttatttc | tttgtccaag | aacctctgtg | atgagtatga | ataggataag  tagcaaagac | 17640 |
| tgtcaatgaa | aaccagtatc | ttagttatt  | ctaaaacact | tcaaccacaa  cttaaccatc | 17700 |
| agacccacgc | ccgccccacc | acgaccgccc | tgagatgtag | caagtggcca  tgtgggccat | 17760 |
| ggaacaccca | gggacgtctg | cccatcctca | aactgagggt | acagcgtcac  tcagataact | 17820 |
| caaaagttac | agaacaaaga | gaggcccatg | ctgggcttcc | ctatcagagt  tcacagcatc | 17880 |
| ccattccgag | gccaaagcaa | ccaacctctg | aaaagccaaa | ctgggagaag  ccagaggaca | 17940 |
| acccggacgg | gaggagacag | cttttcctgc | acagactgag | gctgctggtc  caacctagag | 18000 |
| acagtgtgtc | caagcactgc | gaccctaagg | tcaccccggt | cttccaccca  gagcctgcct | 18060 |
| tcatccttcc | cagatctgcc | tgaagtcctt | tagaaatagg | aaccacgatc  caggctcctg | 18120 |
| tggggatgga | gggcccacct | ccccacaacc | tgtcgtcccg | atctagaggg  gagcacaccc | 18180 |
| cacgtcatcg | tctgcacgtg | gaagctaggc | ccacagtgct | gagacatgca  tatcatcacc | 18240 |
| caccagcagg | agggactccc | ggcagaccga | ggtgcagacc | caagggtccc  agcttccaga | 18300 |
| ccctcactaa | agccttacgg | gcctcacaag | ggctcatccc | agggtccaga  acctctgccc | 18360 |
| ctccctggag | cccagtggct | gcagagcttg | gggaacccgt | ggggttgtgg  tggccaaggg | 18420 |
| tgcagctttc | tgtaacacag | ggggcaagtg | ttcacactgg | gtgggcggag  gagaaggtgc | 18480 |
| tgcggttcct | cccgggtcag | ggtggccagg | agagtcctgc | ccccacagcc  atttctgggg | 18540 |

```
ctctctcaag gcaggtggag caggatgact aactcttctc ccagcaggta cccaaaccca   18600
aggccagatg ctttgtaggg cagccgtgaa accttgccca accctggcag aagccaactg   18660
atgaacacga ccttccccct gggctgtgct gcctaggcct cccccacggc tggtctattt   18720
accattcctg gctcccatga ccattacttt tacgaaaaag gcatggatgg ttctgagacg   18780
aggagggggt tgtaaagacc tgaacttgca cagacagacc ctcagctgga caggaaatcc   18840
cgggtgagct gaggatggcc acactgggag cacacttcag gcttgtgtca gggaccctgg   18900
ccggtgatgg agcagagccc agcctggcat gaacacagcg tcaggtgac tctcaggggc    18960 cggcagcatt ggggtgctct gcacagagct accagaatat cagatgctca cctgcatcca   19020
gaatccagca ctgttagccc tcccagcccc actattgctg ccctggagc tgcctgctcc    19080 cagaaccttc tcaaggtgtc atgatcactg attctgcttc cccgagcaga ggctgctggc   19140
cccacttggc ttcatctgca cttaagttgg tctccagtgg ccagggaatg accctctgtc   19200
tgctgacaaa tagggactcc accctgggca caggactcct tcctgagaaa ggagggagtg   19260
gctgccctgc cagctcccaa gccccacgtc agcacagtac agtcaacact gatccttgtg   19320
aggggaagct ggtcccctct acttactcac agttgaaaaa tgatcaaacg ttagcaaatc   19380
aaaatttggg atgattcata aggcaccttg ttcagtggaa atggtagaaa tgagttgagc   19440 aggagggag gggtgcacgt ccagcgtggc tgcttccggg cagggctgct gggcgggccg     19500
cctgaggggg ctacgtgagc gttgggtccg agatgccgtg gtcggggttg cagctgaagg   19560
caatggtgat ggcatagcgg gtgccccagt ggaccttctc cacccgatgc aggttctcag   19620
acccggaggt gaagaaggat acccgacctg ggagaaggga gaacaaagca tgacctcgag   19680
gtcacacgca tggccgggcc tcagaggacc tgcgttcagg ccgactcagg gacacaagga   19740
acctgcgggc tggagaaacc actgatgcag gaagtcaggg cttggagtca aacctgcagg   19800
atgaaggatg cccagtctg gccacagcct ctctgtgggt cagcctagaa ttgcagtgag    19860
gccctgccac ccacctcagg ggcccctaca agccatgtga cctccccagg cccacctgag   19920
gatcttattt ctaatcacac agggaacaaa accaaaccct ggagggtgat gacaatgttt   19980
taacagagaa ttaggaaaaa caggtcaagg caaacaccca acacctatag ctccctccca   20040
gggcaggagg gagctgcctc ctcctgccag gacaggacac aggagagggc ttctgaaggt   20100
cctggagtgg gcgggtcctc cagccatctg tgctcagaga acccagtgtc tatgtgctcc   20160
aatatttaac tggcctcaca tataccacta tagatttttt ttttttagga caaatggagt   20220
tgaccctaat ggagtcatta gggaggagcc ctgggatccc acagatgcca tgttcctacc   20280
acgtggccca gcaccaaatg ttccatgacg gggactttcc tggtgatcca gtaatccacc   20340
ctgcaatgca ggggacatgg gttcaatccc tggtaaggga actaagatcc cacctgaaac   20400
taagcctgca ggccacaatg aaagatccca cacaccacta ctgagaccac atgcagccaa   20460
ataaacaaac aaactaatca atttttaaaa attttccatg acaacttcat ttcccttcaa   20520
aggtcactgc caggaacttg accgctaaat ctttgaaaag aggagaaaag tctaccccag   20580
agtccactgt tttctggttg taaacaaaag aactgtgctc tgcctgaaaa tagcagaaca   20640
aaagaaaaca tgtaacacgc agaaacctcc gcacggggcc tggggacacc cggaactcag   20700
accctcctct ggaccagcca ggctgcccct gacctgaagg aaaacactct tcccagagca   20760
atctggagtc acaccacttc ctgaggccca agttgttaaa ggacattttg tccttggttt   20820
ctccagtttc aatcacacct gagacatcag acaagcagcc aggccagtct gcacagtggg   20880
ctcaatggcc tccttgccca tccatgccat ccgtgcactc ccaccccrgc acacacggtt   20940
```

```
atcaaatatc gctgacttgc agcaagagta gggggtctct aggggccccc agtgtttctg    21000
cacactttgc aaacagaggc accaaagaac agagaagaaa agactgagga aaagtcaatc    21060
tcctcatggc ctgtgggaca tcaggaaacc atccatccct caggttggac ctttggaggg    21120
aagagaagct catatcggta cagaaaaagg tgatttgaag aaataatgac cactttccct    21180
actgtgatga aaactttgac ttttaaccca ataagcttgt caggataaat acttccagtg    21240
ggataaatac aaattcacac tgaggcacat catagtcaaa ctgctgaaac cagagactag    21300
agagcagctt gcaggtggag agcaagagg cagctactac agggaggtga cagtggtgat    21360
ggcaacaagg gagccagagg aaaaggaaaa tggttttta aaaagaaaa acccaccaa    21420 tccagaattt cacctccagt gaaaatatcc tttagaaaaa agctgaaata agaatatttt    21480
cagaaaatcg tcaccagacc agcacaccat gaaatgctga ggcagaagag gaatgtacct    21540
gtaggaacct ggatgcgcag gagggaatgg aggggctgg aaagtgaata gatgggaaca    21600
ctgaaaaccc ttggcatatt tccctgttaa ttttcatagg agataatcaa ttgtaaactc    21660
agcatcccag gaaaggcaca gtcaagcacc ccagattcca cctgtgagtc ctacctgctc    21720
ttggctccac tgtcttgttg gcccctcct ccatgaacac aaaccgcccc ccaccgaagt    21780
cgtccaggta gtcggaaagg tacagtagtg atgtgtagtc aaaggaacca taggtcacct    21840
gtgggcaaag cacgagggta cgtcaccacc tgcttgcggg agggcttggt tctcaggaa    21900 ggacagaacc caggcctcac actgccctcc caatggcaga aaaccctctg ctgagcacca    21960
gcctgcgtag gtgaccaagg ccctgtcacc ttctggtgaa ttcagtaccg cactgtctgt    22020
ggagctggac tttctacaca gacctgggct ccctccacat tccccaccaa gaccccattt    22080
tggggctcct tatctggtat cagggcacca aacaaatatc agagtggctt aaacctgaga    22140
acagctcagg gcagtgccct tgagttgctt cagcagtgaa cctcacatcc actgagctgc    22200
acagaaccta aaagagaccg ggatgggggg tgtccagtag cctcaccctc tcctacccac    22260
ccagctcaga tactgcaaag gaaccacccc aaactcatgt gagcacagtg gcctgggaag    22320
gaggaaggtt ctggcagatc gtggggatgg cagaggctgt gggcctga gctgttctga    22380 gtcggaggct ggagagcttc acagccagga gcagacgctt cactcctgga gtcccctcat    22440
gggagaacac cttttgcca catccataca tgagcgaccc cttggctatg acaaccaccc    22500
aggtcctgta caccctgtca caagacctcc tagctctaac atgtctgagg ccaccctgct    22560
catcactact gacttgcttt ctctgcctga agaatatctc ccttatcttt cttccttcaa    22620
agtggatcaa ggaaccaggc taccttcagt gttgtctctt ctaaacccac ccttcacact    22680
atgcagaggg ttgctctttc ttcacgcagg gaaattctcc cagactccat cccaaactcc    22740
cttccccatt tgctgcatga acctatctgt cctcagcaca tgatgtcttt gccctgaacc    22800
ccatagaacc ttgttttccc ctctgcaatg tctatgatga tcttacactg aaggtctcag    22860
ccctggttcc ctaatgaaat aatgcatcta cagaatgatt attcaatgag gcaatggctg    22920
ctaaacctgt gaggtgagag tgaacaggaa gcttgatcat aaatggatga gtctgaaccc    22980
agtgatcaat cgtaagccca tgggagcacc cggggtgatg cccaaacttc caacctgagt    23040
cccctcgaac cccctgagct acactggctc agatgagcca ctggccacat gcagctgctt    23100
cactttagct taattaaata ctgggttcct cagtctcact aaccacaggg aagtgctcct    23160
tcctccgtca agctcagaca gttgagatta aataaacaca ccaatgtctg accgaatctc    23220
aggcagaagc ccaatctgcg agcttctgcc caaaccctcg gcttattttt cactttattt    23280
cctttgttcc ggcatcaagc aatgcagaga ttatctgggt cacctgagca cactcgcagc    23340
```

```
tggggtgacc gccaacagcc ctcagacgtt tctgtggcca actctcccct ggcgccatgc   23400
tgggcgtgct ggccgagcag gtcagggtgg ggctgagggg caggcgggag agggcttcag   23460
ttgtggctga tgaagacatt gatagattag gtgtcaccgt gtctagggaa caacaggagg   23520
tcaaagaaga ggaatccaca gaatccaaga gagtctggtc aagaggtctc tccccacaaa   23580
aaaagggggg aaaggggggcc tcctgggcag gggtggggga cgcatatcca aggggagacc   23640
acccaacaga aaggctgaat caaggccggg tcaggtgaca tttgatgaag ctcacggatc   23700
aggcagagac agctctgcat ctgggaacaa gtagcaaagg atggtcccca ccaggccctt   23760
cctgttccat aacatgcgtt tcaccatctt ctctcacctc accacatgag aaacaagtct   23820
tatttccttg acagcatcac cagagaggaa acatctaaaa ccccaactat gagaacagac   23880
agcacctcag tggacgggcc ccagctgcat tcaccttgtc cacgtgagca tgccaatact   23940
catcgtgagc tgtccgggcc tccgtgctgt tgatgcggga gaagaaggtg ggcttcgtca   24000
ggtgcagcga agacgcactg atgccaaacg cctgggcgat cgccagctgg accttctgcc   24060
gcacgtccct gccaagagga cacacgtgtc actcagagca gctggaagag gattctccac   24120
gggtccatgg gacccatatc aaaccatacc acaaaaagac atgaactgga gaaggaggaa   24180
aggtgagcag atacacacgt gggttcacac acatgtgaca gggtatcatg tgcaaaacca   24240
gaaacctgag tgccatttct ctgcagtact cacccccagca ctcccatgcc cccactacct   24300
tccccacctc tgacccgggc gttccttccc tcaccggtac aattggaagt cctcttctga   24360
gaagatagtt tgtattttat ccccaaagta tctgtgaaaa gaataaggag tattaacaaa   24420
tgagacattt tattaatgtt tccttatttc ctttgggtct tccctagtgg ctcagatggt   24480
aaagaatctg cctgccatgc aggagactca ggttcaatcc ctgggttggg aagatcccccc   24540 ggagaagaga atggctaccc actccagtat tcttggcctg gagaattcaa tggacagagg   24600
agcctggtta cggtccatgg ggttgcaaag agtcagacgt gactgagcga ctaacacgtt   24660
tcctttaaat tcagtctttc ctacagttaa ctagcaagtc cttgagaatc agctggtcct   24720
tcttatcttg cagctgctct ttctacaata accgtgtgag aagagggtgg ggggtgggag   24780
ggcagtacct tgcaggtgaa actgttagtt gctcaattat gtccaatgct tagtgacccc   24840
atggactgta gcccatcagg ctcctctgtc catgagattc tccaggcaag aatactggag   24900
tgagtagcca ttcctttctc ctggggatct tccagaccta gggatcgaac ccaggtctcc   24960
tgcattgcag gcagattctt tatcatctga gccaaacaag tggggtgaca tttattaagg   25020
ttgggagatc tcttgctttc ctggccctca ggaggcagct cttaggaacc tggcctgcca   25080
ctcacctctc cctccaccct atctctggcc ccttcccgac tagactgttt cgtaaagcaa   25140
ggtgagtgag tacccagccc ctcggaaaag cttaatctcc cagtcctcac ttggccacag   25200
cctgatggca aatgttgagg ttttccccaa gacttgaagc ccttctgatc catacacaca   25260
agcctcactc aggtgtcccc ggataaaaaa cgggcagacc ctctcacccc aggttctcac   25320
ctgtacaggt ttacaaagtg cttcccaaca gataaggccc ctgagtgcag gtccaggatg   25380
gatgcctgga aaagatgttg gcagagtagc atgagggctg cctggcagat gaccaagctc   25440
taaaagccat caacgttaaa cacaaattcc caagacgtat ccttgcacac acaggtcagg   25500
gtgacaatgc acacaggctg ggtttcaaga catttggaca aaggtgtgtg gggtgctggt   25560
tggtttctag aacaggagac cctggagtca tgcaggtaca ctcgctctca gcctggctcc   25620
tttcactgcg tatcacctcc ctgtgactag ctcacctgga gacggacatg tgggcggctc   25680
ctagttcagg gctgttgcaa ataaggcagc tctgacactg gcggacaatg tttttatcac   25740
```

```
gggagatgct ctcattctcc tgggtaaatg cccaggagca gaattgctgg gtcatcactc   25800
attaatgaac caccagtgtt tctgacccct gcccatccag cctccagaag gccttctccg   25860
tgtcttaaaa gaggggaagg ggcatgagca cggaccacct ctatcctgtt tgggcgtctt   25920
ttctcactga tgcgatgacc atcccagggg gtttgtttga acacaatctg ggcttaaaaa   25980
atgttaacgg cccttaaaga tattaaacct ggatgattca ctgcaacaga acttttcacg   26040
taaatgctga gcagagagta aaagatgagt ccacacacga ataggtttta ataaatattc   26100
cccttgaact gaatcaaaat aaaaggagaa gcttaatttt cagaactcaa aaggaaagag   26160
tctgcagaat aagagtcata gagataatga ctgaactatc cagaggagag cagatgttcc   26220
cctaggaccc acacactggg tgagaagatc cccactggga ccacgtgaga actccaatgt   26280
aaggtgctcg cacagatgga ctctcaaggc tacccaggaa gcggatgagt tacagagctg   26340
cactggcctg tctgagttcc ctgtggttgc tgtaaatggt aggcttaaaa cagcagggat   26400
tcattgtctc aaggtctgga ggccggaaag ctgagatcaa gggtcagcag ggtcccattc   26460
cttccgaagg caccagggga aaatctttcc ttgaatcttt gggcttctgg tggcaccagg   26520
ggtcccttgg tttgtggcat atcactccac tctgctccat cttcacatgg cctcttcttc   26580
agtctcaaac ctccctctgc cttcctctta caaggactct tgtcactgga tctagggcta   26640
ccttgataat ccaggatgat ctcatcttga gacccttaac ttaatgacat ctgcaaaata   26700
cccttttcct agataaggtc ccatcacagt tctgggtgga tgcattttc aggggccact   26760 gctggacccc ccgcagtctc actcagtgga caacagtccg tacactgcat ctgtgaggc   26820 ctgaacatcc tataccctca tttccccttg gagggagagc agagccaaag gggtaagaag   26880
aaaactgaag caggaacaac agacaactca cccctccatc ggatcctccc agggacaacc   26940
ccttctcggc tatgctgtag gggaagatct taagtcagaa ttcagttaac agcatcatct   27000
atgatacttc tagacacaca ccaatcacac agcgaacaca atgttaatgg attgcttaat   27060
gtttatgaca gaatcacatg tttagaccaa aggactcgac tttcaagttg agtaaatgtt   27120
agtattctgt caccacctca ctaacatcct atcacacggt ttggggacaa gtgggcttac   27180
tttccatctt tagttcagag acctggtgct gagctgaatg ggttgctctg ggctggaaag   27240
tctctctcct gtcatcacag gctgggaggc agactgtaat caccagctca ggaggcagag   27300
gccatgtggt actctgggct ggacctcaca ggaccaccca tgtcagtgaa gacgcagggg   27360
cttctggtcc tctgacagat gcttcatggc caccggaaa ctgattaggg gctggatcca   27420
gccctcacac cagtgaccac cccctaccc aactggcccc tacaaggtta tctagaaaca   27480
ggaggagagt ctcccttttgg gactcagctc aacacacaga ccagacactg ctccactagg   27540
cacatgcctg tgtctgaact ccatgtcgga aaagtcaaag caccaagatc tgcttctaaa   27600
agacaagaaa gaatccaatg ccaactactc gtaagtaaga cctcctaccc ggtcatgagt   27660
tatggcgagc tggtgggagg actgatccca atcagttttg gagaggagac tgaaatattg   27720
tctagcaact gcctggggcc actgggtaaa cccgctgtct ctatacaagt gtccattggg   27780
cccctcaacg gctgatggga gagcatcccc cccacctccc caatagacca aaacagagca   27840
tcccctctcc acctccgcag ctgtccctgg agagggcctg ggcctccaga aggttctatc   27900
agcaaccaca tcactgaggg caatagcctt tcctcctgga aatcagaaaa gcccatctta   27960
cccttggaag tatgccgggg aattcttagg gaattctaaa tgaatctctt gaaatcatcc   28020
ttttagtagt aattctctgc tccccgcccc agcctcaccc tcccacttgt tcaggacaga   28080
agctcggaga tgcgtgtacc tgcgaatcct tcgggcttcg tccctggtga tgacggcatc   28140
```

```
gctgatgccc cggccacact tcctcgggga gcagcctaga aagagtcaag tcaggatgac   28200
acacagcccc cactgaaccc cgacacagag aagcatgccg ttgtcaagga ctcacatgtg   28260
ggcccccctt ctcagggaca acagaatttt gtgggttggg gccttgcctt tcacaggatt   28320
agggggccag gtttggaaat tacaggccac gtggtcagag tgaatttcag ataagcaatg   28380
gtgactttcc agtacatgca cgtcccctac atcaaatttc actgtgaaac ttcccataca   28440
aatttcactg tgttcctggc agccctgcca ggcaggccac tctggaagca ccaggcactc   28500
tgcccagagg aggcatccac gacattcttg aacctgacca cagatccaga cctgttggca   28560
agtccctcct ggatgaccaa agctgtgcct gcaattgtag ctgctatcct tttgcagagc   28620
tgctttaagg tgctccccac ccactccccc ctgcctcctt ctgtcctaca gccaggactg   28680
agctgcttag agggagaagg gtgggggagc ttggatgggg atggggccag ggttggggtg   28740
aaagaggcaa agtgggatca gggtcagggt ggacaggatc agggccaggg cggacacagc   28800
cagggtcagc atgacaggcc cagggataaa gtggccaggg tcagggtgga cagggccagg   28860
gtcagatgga tgggcccagg atgaggcaga gcaccagaga tggatgagct cagcaagtgc   28920
ctgtgtcttg gtgcaaaggg caggctggct gtctcgagct gggtggacca caggatatgt   28980
ggctaatgga acactctcag gacacgctgg gctggctgac ctttagcttt tatcctcctt   29040
cccctcttcc tgcctggaac gtgcctggag gtgtcctggg accacataaa ccacacgctg   29100
agtgggagag ctgggggctc agtgcaaagg gctcacaggg agccagactg acctggggtg   29160
actttctctg ggtggataaa cttctacttg ggggtcatta gggaaggggt gcctcagttc   29220
catggagcta aatataaccc tactgataca agatctgtgt tctattaaaa cacaaaaatg   29280 cttttttgtaa gggttactcc ctaaaggtcg atgataaagg caaaaacgac gataaccaaa   29340
cagcagcttg gggagtgata tcatacaaag aaatacactt aaagacaaaa gaattatgag   29400
aggggaagag actgataata ggagcgattc accaggaaga tgcagggggca acagaagcac   29460 caagtgacat cagttcaaac acgtgaggca gccaccaggc ccaccactga ggtggagacc   29520
cgcctcgcag ctcccgataa ctgaacaagg caagacgtcc aagaagacag tttgcccaga   29580
ggagtgtaga ctaggagaca gtcagagctt cacaacaacc attcaaaaac agacattttt   29640
tcaggtacac atgcaacatt aacaaaaaca tattagccca acaggaaagt tggttctgta   29700
ccatacaggt gatggtctcc agctaccagg cagttagaga gaactcaagt tccatcaatc   29760
ttgaaacctt aaaatccagc aggacacagc acactgaata tgaatgagcg ttaaagagta   29820
tcatttgggc aagaaagtga gttgtgagtg gtggtgatgg ccgtgcatgt acacaagtgc   29880
acaggacaca agcacacaga tgtgcctccc agacacacaa gtccggtgca ggcagagccc   29940
ctgtcagcta tgggaggaga caagggtgag aggggggagt ccagagactt cgatgctgtg   30000
tttttctggt aaaatatata taaaaccccc aatttaccgt tttagccagt tcagggacat   30060
taactgcgct cacattgttg cgtgaccatc accaccatca tctcccgaac tttctcacct   30120
tcccaactga aatcccatct ccatctacac caactcctcc tctgccgcat tccaactgtt   30180
tttaatgtgg ataaattatt aaaggggtag gagaaataat ggctcagcgg taagaatcc   30240 gcctgcaatg cagtagacac aggttcgatt accgggtagg aaagatcccc tggaggaggg   30300
catggcaacc cactccagta ttcttgcctg gagaatccca tggacagagg agcctgccgg   30360
gctacagtgt acagggtcac aaagagccgg acacaactga agtgacttag cacaggaaaa   30420
acatactttt tcaaaagctg ggactttaca ggaaaaagc tcaccaagac agagagagca   30480
tgccgataac agaacctgtc cactcctgac ccccgagggg aaagggaacc ccagttcctc   30540
```

```
ggcatgtcca tttctgccaa ggagcccaca cacctccctt cactttaacc caacttgtgc   30600
gcatcacaac agtgcccctt ggtggaagga ctcagcaatc ttttcttgg ttcaagttca    30660 aagcgctgct ctgaatagaa aaataagtt ctgtctctaa gacctggtca ctctggctag    30720
gcttttaaaa ctgctgccct ccacagagca ggcaggtgcc aggatgggac aaacgccatg   30780
gtgggatgga ccctggtatc acgtttcctg ttgcaacatt ttctgattta caatcccct    30840 aagacagaaa atgcctcttc tcagttcaac ttgttcattg atatcttccc aattctgtta   30900
catctttcca ggcaaaccac ctcgtccacc agatggaatc cacactgagg tgggggggca   30960
cctcagtaaa atactggcca tagcctgggc agtgaagcct gggcctgccc ctgcactggt   31020
ggggcctgaa acactcacac tccccagaac aggtgtgagc taaccaacgt agtggggggg   31080
cagtggggag gaatgccgcc tgtacccca accccacatg actttcgacc tgattcccac    31140
caattcatca aagtaaaaac agatgcattt tgaacacacc aaattctatg ttaacatgct   31200
gctctttcct gaatcacctt ggcactgcgt accttcaaac cttcggtgac tgtcatagtc   31260
ctcagagcag ggcacctcga tgaacctgcc tggcaggatc tcgctgcggt gagccaggac   31320
ctcagtgatg ccgtcatcac cccccaggct gccccagaac aggcaggcgg cgagagcagt   31380
gcaggacccc aggacaacga ctcttaacca cctcttgcgc catcccgag gcgcccggac    31440 actcttggtg ctgagaacag aaaacagctg tggtcacccg aaggcaactg cgtgtgctga   31500
aaactcagat cacaatgacc agagaccaca cccacactta gttacagcct taaaggggtc   31560
ccacactggt catcatcaga gctactctcc atcaatccag aggcacttgc cagcatacga   31620
ggacatggtg gggaatgtgc ccctcgcccc atacgaccag acagggctca ctatgccccc   31680
gaggacaaga cgaactgcta gtcgcggtcc ctcccagcct ggccatgtcc atggagaacc   31740
atctgggaga tcctgacaga gcctgtgaca tcgatcacat tgcctgcatc cgaagatgac   31800
tgacacaacc ccatgcactg gccctagggt gcacactcac acacaacgtg aactaaggca   31860
gtgaaagtcg ctcagtcgtg tccatctctt ccaaccccgt ggactataca gtccatggaa   31920
ttctccaggc caaaacacta gagtgagtag ccttttcctt ctccagggga ttttcccaac   31980
ccagggatcg aatgcgagtc tcccacattg caggcggatt ctttaccagc tgagctacca   32040
gggtgaacta aggtaaacac gaatcaaact catttcactg aaaccaccag gcagccggga   32100
aaagaatgca agaaccacag aaatgattcc acactaagac actttctgta ccacctgggt   32160
taactgttgg attcacactg tctatgcaga agttgcaggc atgtctctgt gcgtgtgtgt   32220
gtgtgtgcat gcacacgtat atctatgtgt gtctgcatgg tgtatcccca ctcatatgtg   32280
tgtctgtgta catgtgtatg tgttttctca tatgtgtaac tgaacagtcg tgtattctat   32340
taactgagaa aaatgtgtag ggcttgaagg actggcagaa atgagaaaag cgatccagac   32400
attgtttcag gaggtgcacc tcatgtcttc aagtgtatga ttaattcctg aaaaccagga   32460
agtctgcctt ctatttttat atgtccctcc acatttcaaa gtgctatata tataaaacac   32520
acacaggctt ccctgctggc tcagagagta aagaatccac ctgcaatgga ggagaccagg   32580
gtttgatccc tgggttggga agatcccctg gagaagggat ggctacccac tccagtgttc   32640
ttgcctggag aattccatgg acagaaaagc ctggagggta cactacctgg ggttgcaaag   32700
agtcggacat gactaagcga ctaacacttt cacacttta ctttctaaca cacaaattcc    32760
gattaaataa gtctcaaggt gggcacagct gagtcagatc atattgggtg gatacatggt   32820
ccctttaaac agggagcata gatccccagg tcacaaagac cccatcctc cacctagaac    32880 tgctgtctag cctctagccc acctggtctc ctctaactag acaagggtgg gcccctaact   32940
```

```
ccaatggggc cagtattttc ttctccaata gggcagggag actgccagcc catctcagca    33000 gcagggggctg aaatcctact gtgggcacaa agctgttgac accttcgcct gggacacccc   33060
aggtgctgag acagaaaggg acagagaggg aggtagagac aagagggaa aaaacagcct     33120 cctggtccag atttggaagc tatacttccc tgaggtgtcc tcaaaataag caccctgtt    33180 cagggtaagc tggcccaaat gcagactgag aatcttgctg aaacataagt ggatttggag    33240
caaggtccat ggcccattgg gcaagcacga cgagaaggta atttatcctg aagtgaatac    33300
actccggctc tgaaagcttt aggcagaatc ccctcgaagg ctacctgatg agatcattta    33360
ttcattcatc gggtccccca acggagaacc gtcacgtgca cagccctgag aaaagcacac    33420
ggagaccaga cgatggggac ctctgagtgc cagtccccgt gcgtagtctc ggcacaaagc    33480
cttaggtaca aagccctcgg tccacactgg ggaggaagga ggtcaaggaa ggtttcccga    33540
cccgcagctc cgcccaaccc cttcctgcgc ggtccaggag ggattctgca ggctacgccc    33600
tccggacgac cacgcccctc taggcgcccg attcgcccaa ccacaaacca ggcccctcgc    33660
ggccaggcca cacccacact gcagtgcctt tccgggaaag gccctgcctg caccagatcc    33720
acctttttct gaccgggccg tgcccacagc cacccaacac cacgcccctg ttaggccccg    33780
cccctcggcc aggccccgcc catgccacca ttcgcgcgct cccggcgcta tctggtacct    33840 gctctgcgc cgacgctccg ctgccccgct gccctcgggg gccttgggag cacccctccg     33900
ctgaggtgcc attagctacg ctgccgcgaa actaggccga atgctggagc cgccacaagc    33960
ccgggacgag cgctgcgaga ggtagcgcga ggccggcgcg gccgggcacg cgaagcgaca    34020
ccctcagcct tcaacctccg agctggtgac caggcctgag caatcggagg tcgagcgccg    34080
agcggggcag ggcggggacc gagcgcgggc ctggcttgct ccccgcggcg cacctgcctt    34140
ggccgtaccc cgcctcccct gacctccgcg gaacctgagg agcctgcgaa ccttctacag    34200
aagtgtgtcc ttgccccgtc gtgcgtgctc taccggggtc tccaactcct cctagagtct    34260
cgaagccgtc tccccgcggt gtccaagccc tcctcccagg gtctccgcac cctttcctgt    34320
gggatttcca acgctcctct ccctgggccc atgccacacc tgagggcact gggtcctgtt    34380
ggtgcttagt atctgaggcc tgctgtttag tttacaacat tcagtttccc gtccagtggg    34440
caagaagtaa gatcttaacc agtcctgtca agatacctaa gattctgaat gagtggaatt    34500
aacagtgagg ttcattcata aagattaagt gtgaagaagg tgagtaattt attgatacgg    34560
ggcgggggga gggggaggga atctggactc attgaacaag aaaagagatc tgcccaacaa    34620
tccccaaact ggggaaatca gataccatcg cctggcaact tacctagaag cccaagagac    34680
tgggacaatt gcagatctac gtaccgggtt gtctgatagc aatagtggca agtctgaaat    34740
aatcatattt ctatagacct cgtgcaggag ggaatcaaag taaagaacta cacacttgca    34800
agagggaata ctgacttctc tgtctccttt ccctttagat tttgcagcaa cttacttttgg   34860 taaacaactc tgaatgtgtc tgaatcaggt aagatgtcgg tgttcattcc tgctgtaggg    34920
ctatagaaaa gtaagaagat ttctctctaa acacaaggaa gcacacccag gactaataca    34980
gacttctcag ctcaaaaatt tttcttttaa ctctattctc tggaaaatac atttgggtta    35040
tagcgggggc gggggggagg gttgttagag ttttctttt tattatttat tttttcaaaa     35100
tgtaaagcaa ctcagctttg aaacatttca gttttcaaa atgcttggtc ttaaactcat    35160
ccacttctca gatggcaatt taagtaattg ccttaagaac tttgtcattg agattgtttt    35220
gaatataatt ttttttttca atcaaactga tcgatttcta tgtgcattat attattgtct    35280
ctgctatatt ataaagtccc taaggtcagg gatttatgaa tccttgaaca gaatgagtag   35340
```

```
tttgaattgt ggagctgaat atatgatcaa tatacagaga ttttctttcc ttttcctgtc   35400
taattctatg tgttttatgc ttcatccaga tacctcctct agtttaacat aaactagtca   35460
gcactgataa acttgtgact tacttgtttt taaattatca atggcctatt ttaaatccta   35520
gacagttttc tctgacctag gataaatttt tacagtttct ccttccctgc aaccaagctg   35580
actcaaactc taaaaatgca aattatttct aatactattt aaagtagaat aaaattgagg   35640
atcagttttc tacagaagca tcatattgtg gggcctgaaa aatgtttaag agatatttgc   35700
ctgttttcac tggcatagta tatattggat aagacagtct ttaaaacagg aaattatttt   35760
gcagtcattt gtattattgt agattatagc catcttataa ggaaaccagt gctgtatgac   35820
aagggtcctt gtatttgaac ttggagacag acatcttgat atatttcgtg ttggtgaaat   35880
gagtttcctt ctagttcata tcagaattga aacagacatt ggaaggatat aactctgaat   35940
ttcttcacta ggaagaagtg cccagaaaag agatttttta gttatatgac ttctcaaaaa   36000
atagtgggat gtcgggttcc tcaccattta agatgcgact agttcatctg gacctgaaag   36060
gagccccgcc aaaggtctgc tacctctcgg aggtaagagc tcccttctt ctctagaaa    36120 tcgctttgcc tcgggtttgg ttatgaagtt gtgaacagta ttctgtacat acattttttgg  36180 aactcaacca tgggttctga gttgcggcgt ggtggcagca gcatagatct tgaatttccc   36240
ccatatcccc tcacaaagca gatagcaacc aggatggcaa aaggaaaaac agaaaagaca   36300
aaaccccaca acctctgttg tgaaccaaat cgcgtctcct aaaaagatat gtttaaatcc   36360
taacccagcg gacctgttaa tgtgacctgt gatttaaaga tagggtcttt gcagatgtct   36420
ctgacattag atgaggtcat atgggaacag ggtgagctct aatccaataa gtggtgtttg   36480
tataaggaga ggggacaata gacacagagg gaagaggaca tgaggacaga ggcagagact   36540
agaattgatg catctgcatg cccaggaggg taaaggatgc cagaaactcg cagaatctgg   36600
aagagacagg gaggatgccc cttacagcct gggagggagc acggccctgc tgacacctag   36660 atttttgggct tcatcctccc aagctgtgag agaacacatt cttactattt caagctcccc   36720
ggtttgtgat gacttgttat ggcagccaca ggaaaagcat gtactctaaa acaaatgtaa   36780
gttatcagga ttttcctgtg aatgccaaaa tgcaagggc ggggccaaac cacggacaga    36840
cagctcaaca ctcctgtggg gttagcagct gggcagggga tggtagagga aaggtaaaaa   36900
agaatttagg atcttccctg gtggttcagt ggctaagact ccaagtcccc aatgtggggg   36960
gcccaagtgc gatccccagt caggaaacta gatcccacat gatgcaaatg agagtctgca   37020
tgccacaacg aagatcaaag atcccacgtg ccgcaactaa gacctagtgc agccaaataa   37080
atacaaataa atattaaaaa aaaaatagaa ttcagatgac tccaagacca gggaatccac   37140
aaaatagccc aacaagtaaa ggtaagtcag aaactggagg agatgtcact ggctccagat   37200
tgagaatgag tgctcaagac ctcaaggcat tccaaaatac tttccagaaa cttcttccag   37260
aaggacagaa ccccacactc agaatgcaat gttgggaaaa gactccatct tgaactgggg   37320
agtaacattg aggtaaagga gagagaagtt tcaaatactg gagaaacagg atccagaggg   37380
agtgaagact gagtgctatg gaagtagctg cacaaagtcc gtaactgcta atcctttatg   37440
taacagctgc agagggagcc ctgggctggc ccagctccat cccaaacata gaacctgct    37500 ctccaaaata caagaaaaca aatctcattg taaaatgagc aataggaaag gagtgtggtt   37560
gtgccatatg aaaaaacatt gccagaaaat agaggaccat gatttgagta acagtgaagg   37620
cgcaccagca ccatgtgacc acaaagcaga tggcacagtt ctgtaatatt tcaaaacaag   37680
atcagagata ctaagaagct atggaagaac agcatgagtt agaaatagaa acgcccagtc   37740
```

```
ccacatgctg caactaataa cccggcgtgc tgcagtgaac atcgaagatc ccccatactg   37800
ctcttagaac ccacggtagc caaataaata ttttaaaaag cacagaaagc catagccaga   37860
caaaagtaga ttgtgaaaag attgcctcca gactcaggaa tgaattataa gaaaaaaaaa   37920
aaaatcagaa atagagacta aactagaaaa aggacaaaag tgaatagaca ccatgggaac   37980
cagtgttgag aaagcaacgg cagaaaagaa aaaaaagtca aacgtgaaga gataaaagca   38040
ctgtgacaaa tggataggtg tgagagacag gcaaagaaga cccagtttgt gtgtagctgg   38100 agcccctgc tgttgctaat ggacagagtc aggttcagac aacaatttct tattcatttc   38160
attacctgct gctgctaaca gacagtcagg ttcagacaac aatttcttat tccccctgtt   38220
tctgaggatt tgctgggtgg ctccctcagg ctgagcttag cagcctgtca gccacccagt   38280
gcaccgaaga tccctaccag ccccaacaga atgctaaag aggccaccca atagtcagat   38340
ggctaaaggc tgcaaggaaa accaggagca aaaatgctgc ggaaaatatg gaaatgctat   38400
aaccgttatg tttcatttgt gcaagtgact gacctgggtt agtttgactc ctttccacaa   38460
tcagcctcct cttataattt gcagtcaatt gtcaatgacc cactttataa atgatcttag   38520
ctaattcctg gtccgaagct gatttccttc tatccagcat gcttaataat gttcccatgt   38580
tcctggggaa agaaagcttt gacagcaaca tcagcgagag tgctacaaat tgtataaaac   38640
ttgtagtggc ccttgtctgg aggtggattt atattctaaa tagttacagg agccctcacc   38700
cctgcctgtg atgccaggct aaaagaaaat ctcagtgctg tgtacagtag atacagccct   38760
aaaagtcctg gaggatagga gtccatgttc ttgagataaa ggtggaaaaa agaagtggga   38820
gagaaccagg gcagggaccc tgtaagcaca gagggacaac ctctttcctc cttcatctac   38880
ctcctctagg cttcttccag gcgcccacca ctagccctcc agagcctata ggctcccatc   38940
gccccaggcc gcccttccc tgtgttctag gaggccccca tgctgcatgt ctcatccaga   39000
tgaggtgccg tctgaccctg cttgcccaac cgtccctccc cagctaagcc actaggcagc   39060
tgctattcta tagcaagcag aaaccctgcc ccttgtgtca agtgaacacg tcactacatt   39120
tgtgtttagt tggcataaca cagagtacac atttcaggtg gaaagtttcc aggagaatta   39180
tcagtccaaa gatcagctat aatgcatgtc catcagctaa aagaatgagt ctgtgacctg   39240
catgtgtgtc gttttccatt caaatagtca tgttttcatg acgtttctgt ctcctcccca   39300
gattttcccc ctgttccgtg ccctgggtgc aaatggcatc tcattgagt atgaagacat   39360 gtttccctac gagggccacc tgaggctgct gagggccaag catgcgtaca ggtatctgag   39420
gtgccaagca gggcaatgcc tctgtagaga agatgggatg tgcagggcag caacctggag   39480 gggaggggggg gcaggaatca taaaaataaa gcacgttcac tgaagagaat ttggaaacgt   39540
ttaaaagaat ataagcatcc atatagtcaa agctatggat ttttccagtag tcatgtacag   39600 atgtgagagc tggaccatga ggaaggctgt gtgccaaaga attgatgctt ttgaactgtg   39660
gtgttggaga agactcttga gagtcccttg gactgcaaag agatcaaacc agtcaattgt   39720
aaaggaaatc aactctgaat actcattgga aggactgaag ctgaagctcc aatacttttg   39780
ccacctgatg tgaagagctg atacgttgga aaaggccctg atgctgggaa agattgggga   39840
caggaggaga agtgggcaac agaggacgag gtgattggaa gacatcactg actcaacgga   39900
caagagtttg agcaagctct aggagatagt gatggtcagg gaagcctagc gtgctgcggt   39960
ccatggggtc acaagagaatc agacatgact tagaaactga gcaacaacaa ccacaaatga   40020
tcccccagaa ggaagcgctg tgatttgttt cagtcttgtc tgtggatatg aaatgcatgg   40080
aggacacttt gacaggtgtc catgcagaag aaggagggag ggtctttaag gccccaagtg   40140
```

```
ggatctttat cagaaaagtg aggattaaag gggaaaggat cagaatcatg gagaaggcaa    40200
tggcacccca ctccagtact cttgcctgga aaatcccatg gacggaggag cctggtgggc    40260
cacagtccat ggggttgcta tgagttggac atgactgagt gacttcactt tcacttttct    40320 cttttcatgca ttggagaagg aaatggaaac ccactccagt gttcttgcct ggagaatccc   40380
agggacggga gagcctggta gactgccgtc tatggggtcg cacagagtcg gacacgactg    40440
aagcgactta gcagcagcag cagcagcaac agatcagaat caggaaagtc agatagcatg    40500
gtcatgggca taccgcattt ggctttaaaa ttatgggtat ccatgtaaat caataacaaa    40560
tagcccaaaa gaaaattgga caaagaacat tttgatcccc ccaaaagaaa gaagtatatg    40620
gtaataataa aacaatgaaa tgccattttg gctaccaaat tggagaagct tttaaaacaa    40680
aatgatagtc ctctgtgtcc acaagggtga gcaaaaacta gcctcctgct ggtgggctgt    40740
agagcagcct aactgttctg gagggtagct tggctctgtg tgacagaact cccaacatgt    40800
gcctatgagt gggaagcagg aaaggcatga tccagagcat taatgtggtg atggcagagg    40860
tgtttgtgtt tcttttgtaca acgaacgtgt tctgttcctt tgttttaaa agtgaaaaag     40920 gtaccagggt tccagtgaag cttgaaaaag gtatatttaa agatagaacc ttatgtcatc    40980
agttcatttg taaaactgat taactttaga gatggttcaa acacagaaat tgagatgaat    41040
tcataaatga caccctcagag tagagtggtc cggggcccctt cccggatggc atcctcagta   41100
tctcagtagc aggacgttga cctggacgaa cactcaggcg tgctgacagt gacttccttc    41160
caagggtttt gtccatttgt agatggataa acaaatgcat gtgtgctcag tcatgcctga    41220
ctccttgtaa tcccatggac tacaatctgc taggctcctc tgtccatgga agttttccag    41280
gcaagaatac tggagtgggt tgcaatttcc tactccaggg gatcttccca acctggggac    41340
cgaatccacg tctcttgaat cttctgcatt ggtaggcaga ttctttacca ctgagccacc    41400
tggaaagcgc taatagatgc ggttactaac cccctcagat gagtcactcc acctagtctt    41460
ggtactctat taaaggggtc accagccttt tctataaagg gccagacagt agatatttca    41520
gtctgtacag cccatctcat ctctgttaca actgtttgtg gggcaaaagc agccacaggt    41580
gataataatg agtgggcatg gctatgaccc aataaaaccc tatttgtgga cactgaagga    41640
tgaattccat acaattttttg ttcttttgtt actcatttgt gtccgactct ttgccaccca   41700
tggactgtag ccctccaggc tctccagtcc atgggatttc ccaggcaaga atactggggt    41760
gggttgccat ttcaggaggg tcttcccaac ccagggatcg aacccatgtc tcctgcactg    41820
acaggtggat tcttttaccgc tgagccatca gggaagccct cccatatagt ttttgcaggt    41880
cacaaaatgt tattcttctc ttgattgttc tcaacaattt ttaaatgttg aaaccattct    41940
taggtcatgg gctgtacaga aacaagcggt gaatttaccc tcaggccctg tcttcccacc    42000
tttgttctag actatgattc cttgtgtggc ccagtttctg gtaaaatgac tttagcttct    42060
taaagagttt gagtcagaat agctggtcag aagtaaactg ttacttgatg acataacaga    42120
gcatcgtttt cctgaactgt agcatggaag ccttctctga aagcttaaga atacctgttg    42180
ggcttttcag agttagtgac cctactagtt tcctcagtag agtcccccag gaacctgaca    42240
agcggggatt gggagcctaa atggaagccg gcctgcacct cttagggtgg tctttgtctc    42300
tctagccctt cggaaatcaa agagatcctg cacctggcca cactgaatga gctggaggtc    42360
attcccttgg tgcagacatt tgggcacatg gaggtaagtg ggaggaaggg aagttacctt    42420
gcacccagct gtggggttca ggggtgcacg ggcagggcta gccacctgca gggaacagct    42480
cagcgctgca cagagaggct ctgtgaacag ctgaggagct gttgtctgat aaatccaaca    42540
```

```
tccaggccct ctcaacgtca gtttccatag actggttttt cctttgagtg tccatcccac   42600
ttgccagtta tttgcacgtc tcaattttg gttgacaact ggacatttca gatcatatgt    42660
tacagcaaat ctgactttt ccccatgggt agttgtaaat tgcctggatt taatctgtct    42720
ccccagatgt gtgtggccac aaatgcctct gttgggtttt tattcttgtt tttatttttt   42780
gctcttaggg ggtcactctt ctgtcttgac agctggtgat tccacgcagg ttgggcagta   42840
gttgtgccca agcccgtaag gctccacgtt atgcccagg ggctaggggt gccacacgta    42900
agagctcagc cagtgctcag tctgctgtgg ctcctgcttt ccacccagcc ctctcaggcc   42960
cgtgtgtgtg tgtgtgtgtg tgtggcccca gccagctggt gtgaaggaga acatgtgtca   43020
cctttgtggt cctgtgagga ccgcagaatt cagaacagtt tgccactctt actgacaggt   43080
ctccaaggac tgggtttacc cacatccagc tgctggtggg cacaggggt ggggccctgg    43140 gcagaagctg cagaatctct gttttacc aaagttgtgg cggtcttca tgaacaaaca     43200 tttctcagtt tgttgttcac ctttggttgg tttctgaagg cctgaaattg tttttgacaa   43260
atggttccac tttgtacttg ttgtgtgtgt gtgtgtgtgt gtgtgtgtgt gtgtgtgta    43320 tgggcagggc aatggggagt gggtagtttg ccagcctctt cacttgagca agaagtccac   43380
ccacatgtaa ttctgctgtg aagggagact gtcttgtcca ctttctcact cagcctagtt   43440
agaggtggaa gggagaaggg ctgttgacca agcagcctgg ttgctcagag ccctggctcc   43500
cgtgcccagg gcagtcccgc tggccccct gggaactcta atagacacga ggctggcagg    43560 gtgcagggc aggagcccag ctgtggggag ctcgggcata agcttctccc cagggttgcc    43620
agctttccta ttgtctccct gcagttcgtg ctgaagcacg aggctctcgc tcacctccgg   43680
gaagtggcac gtttccccaa caccctgaac ccccacaaag aggagtccct ggcactggtc   43740
acagccatga tcgaccaggt gatggagctg cacccgggcg cccggtggtt ccatgtcggc   43800
tgcgacgagg tgggtgcctc cccttgccag caggcaactc ccctaagtct gcagcagccc   43860
cttctcttca cctcaaggtc acctgctccc acctcgtggg gtcttctctt aaatagaaaa   43920
gtagctccag gaataaagaa aggctggctg aggagatgtg cccagtgag ggccgtggtc    43980 ccagctgaca agtgatctcc cgtgggcaaa cctgctgagc caagcagggt gcagtggggt   44040
gcaggcaccc acgggacagc agagcagccc ctagttactg cacgttcatg tcctgggc     44100 caaggtggcc atgagattga gccgggtact tttctccatg tgaagcagtg cagtttcaga   44160
cagtgggaga agggaaatac cactttaggg tcatggagca ctggctggaa aggcagttcc   44220
caggggtgcc ccaccttgtc ctcaagaaac acaggatctt aggaagatta tgagccaccg   44280
agcagtgacc caaagacctg tgctcgtctg agctcaggca tctgagctag acagtggtt    44340 tgtggacatt ttattccaga gtttgatcct cttcttcaaa aaacctttt tttaaaaaa     44400 aatacatgta atatagaatt tatcaccgaa agcgattgaa agtgaacagt ccggtaactt   44460
tttagtcatt ctcagtgttg tgcagccctc atccccgcct agtgcagggc ctctcatctc   44520
cccacccacc cccgccctc tacctctgca tccatctctc ctttgcatct ctgcattatc    44580
cccccgcccc agcacccgt aagtgaaatg ctgctccatg catgggcttc tctccctggg    44640
caccttctcc agcttcattc atctacatgg cagctgagtg atattccagg gtgtggacag   44700
gccacgctct gtttatccat cttgtgttgc tggacgtctg gtcatttta ccttctggct    44760 cttgtggtgc tcctgtgccc aggctcaagg gagtcttaga gctgagtttg ggtgttggtg   44820
aagaggcagg ggcgccctc actgccccct ccccatgggc agcttcccg agattctccc     44880 aggccacagc atgaaccttt gggtgaggat gagtggtccc ggggccaacc caccgtgtc    44940
```

```
tcctcctagg tctactacct tggagagggt gagacctcaa gacagtggtt gcagcaggag   45000
cccaacagca aagcaaagct gtgtctgtcc cacatggagg cggtggccag ccacatgcgg   45060
gcccggtacc ccactacaac gcccctgatg tgggatgaca tgctgcggga catccccgag   45120
gaccagctct caggtcggca gggcgtggcc ctggcgggcg gggggtggta gtggtgatgg   45180
tgcaggtcat gctcagcagt ggggcttcct ggtgccacga ggagtggaag ccaagtgctc   45240
cgagccccca gctgctcagg agagacctag accctgttgt agagctgcac tgcagcttct   45300
agttccagac catcccgtta ttaggaccac tttcatgtgt ttctcatatg acagtgccat   45360
ttccctaaaa ggtcttgcag gagtgtggtt gtgagagacc tgacctggag ggtagcatga   45420
ggccctgggg gcggcaccga ccgtcggag caggggatag gttcggagca ggggccccca   45480
gcagaccatg agagcaccca gtgctcacag cacctcacac gcctgtactg ccagcccgtt   45540
aggggctcca ctgaggttca cactggctgg ttgagggaag cagaggcccc ccagcccaa   45600 gcccagcaag gcctagcttg aggctttggg gtgagacagg gagattgcca cacatgcttc   45660
tgcaaggtcc aggtgtcctg gctgcggccg ttaccacgtg tggccactta agttttcatt   45720
cattataaat aagtccgctt agcaatgcat tcctactgca cctgggcctg cccgcgtgc   45780 agacacactg ccgctccctc ccttgaggga gcaccggggc ccatggcctt agcagctcca   45840
gcagtgtcca gtcacttcca gagctgactg gcctggcggc tgcggcgttt atgaccaaac   45900
gcttagtgca gtactgaatc tgtacttgct gctgctaagt cacgtcagtc gtgtccgact   45960
ctgtgcgacc ccagacagg gcgcccacca ggctcccccg tccctgggat tctccaggca   46020
agaacactgg agtgggttgc catttccttc tccaatgcat gaaagtgaaa agtgaaagcg   46080
aagtcactca gtcgtgtccg actcctagcg accccatgga ctacagccca ccaggctcct   46140
ccgtccatgg gagtttccag gcaagagtac tggagtgggt tgccagtgtc ttctccggag   46200
tctgtactta aatccatttt aatgcaagaa aggagggctg aaggctgaag ggacccgccc   46260
tcatggcctc tctccactcc cagggtcaag ggtgccgcaa ctggtggagc ctgtgctttg   46320
ggactatggg gctgacctgg acctccacgg gaaaggtcag taccagaacg gagccgggcg   46380
gtcatgggct cctcttggtt ttccccacag acaagcatgt atttcgggct tcacagctac   46440
acctcgtcag ggcatgccac tcacacctct tacttgctca cccagcgctc cttgtgggaga   46500 agtaccggaa gagcggcttc tcctggctct gggccgccag cgccttcaag ggggccacag   46560
gagtgaacca gagcctgacc cctatcgagc accacctcag aaaccacctg cagtggctgc   46620
aggtggcggg cagcgtgcca gcggacacgc ttcggggcat catcctgact ggctggcaga   46680
ggtgaggcca tgtggggccc agggatgccc ttgggagggt cgaagcggct cccatcactc   46740
aggacacatg gccctcctca gcccatccag tctgggcctc agttctcacc ttctgtcaag   46800
aggaagcagc cagcactctg aggagggtgt ggaggaccag ccgcacaaaa caagcacttg   46860
gggtcaagcc cctcacacca cactgctgag gggatgcggc tcagggtgtt agcaccccag   46920
ggcactgggc tcctggtgc acgctctgtc tgcaccgtgc gtgtctctgc atgttcacac   46980
caccccagcc actttgggag aggtatgaag acagacctca gctcattcag aatttcacac   47040
tatctgaaaa gtagagttac aagttaacgc ctagtcccag gcaagtcctg gcctcaggtc   47100
ccatcctgag ggggaggcca ggggcccaa caccaagggc aggaggccct gactccatgg   47160
gaggcaactg gaggcggggc tgactgctga ccctcagccc tcacttacag agctgagtca   47220
aagatgaact tcaaagaatt tcaaggtggc aactacagag cattcagccc aggcaggtcc   47280
ctctgggtgg gatctgagtg tgactgccag ctgcagaccc acaaaaccaa ggaagcttct   47340
```

```
ggaagcagca gaagcttctc gatccctgtc ctgtctcgcg gtggctcatg cccgagcatc   47400
cactgagtcc ctctcccacg gacttaggta tgaccacttc tctgtgctgt gcgagctgct   47460
gcccgtggga atcccgtccc tggccgtctg tctgcaggcg ctgctgcacg gtatggtccc   47520
ctgctcctcc caggaaacca agtgccagga cccccaactg ccacctccac ctggctggac   47580
tgtggtctta acagcctggg tcttcaagcc taaacccaag acagaggcca ggaaggtagg   47640
gggacgggct cctcaggcag agtgaaccca caagaaagct catcatggat agggtgcagg   47700
aaagggcccg tcttcactgg gtgaatatcc tgaatgccca gtgccagtgg gtgtggcccg   47760
cagctccctc acttctggtt ctcctgggag cagccaggtg caggcagaga tgcttagaga   47820
tggacgaaac cagcaggcgt gcctgatggt gaagccctgg ttaggtaaac tcccatttga   47880
gacctgatga taaatgtgct gttggagcag aaagatgtca aggtggttga ggaaagtgag   47940
gactgaacag tgaacatgtt tagaattgtg ctgagccaca gggatgtgga aggacagata   48000
ctgagactct accctttttct aaccttcccg caaggctgct gtggccttgg gctcatccat   48060
ccctgaagtc agcatgtgtg tggctggacc tggccagcgg tccttctcga ttgttttgcc   48120
cacgacccat gcccaaaggt cgggaggtcc agccagcacg gggtccaggc cacctcctcc   48180
aggggcctct ctgacctccg tctatggttg gtttcaggag actttgctga aaatgtcaaa   48240
gcaagagtgg agaactttct tgggatttcg agcctagaga aaatgagttt taggaggtaa   48300
cactctcact ccctgccctg cctctcccct cccatttgag ccttcctca gcacggcggc   48360 tccctgtgca gtgagggcgc cggctccttc cctggcagcg acatcctggc cctcgtcaca   48420
caagtcagcc tccacctgtg cagctccgtg gacgcgctgc tggagaggga caggtgagca   48480
ggccggggag tgaccccac cacctcctgg cagggcaagg gccagctaat actgcaagga   48540
agcttcctag gtggaagctt ttaaaaatct aacttgtaaa aatctttacc agattttcaa   48600
aggtcttatt ttacaaccac cgaggcagcc ttacaagcca cagtgcaccc acctatgtgt   48660
gtggatttgt cccccgcccc ctggccccca ccccactgca ggtatgtgac cggctggttc   48720
agcccctacc atcgccggag gaagctcatt caccccgtca tgatcgagca catccagccc   48780
caggcactca ggtagcccac ggcccgcccc actgtgtcca tccccggcac tgcccaccct   48840
ccactgcact gggagccttc tggacgagct gactaggtat cacagccaga gtcctgggtg   48900
gcccaactga atcagctgtg cccttaggtg tcacgagaag cttggacatt tcctgcctga   48960
gagggttgag ggtcaccaga tgccctgagc cggatctggg gctcctggta ggaccagact   49020
gcctagggct gtggccgcat gtgtcaccgt ggggacaggg tcccagccgg cctcccccg   49080 ctcccccagc tctgcaagca gaggccaaca cagactgtcc ccactgagta taagatgcct   49140
tcagctgcca cggcaggttc acgcaccaag aaaaaccctg ccagccagtt gtgaagtgcc   49200
tgctggttac aaggtcaaac tgacagtcac tcattgattc ccaacaacct tatgaggctg   49260
gtgcgaaggg cccagttcca tggatgagta aatggaagcc caggatgtcc tgacctgtgg   49320
ggttctggag gctctgaggt atgcccagg gccctcattg gcaggctaa ctgtctcgct   49380 ggtcctcagt ctcctggcca ggtggaacgc cctcgcaggg gagctggagg ctgccctgca   49440
gcgcatcttc tacccagaca cggtggagga gtggctggag gagaacgtgc accccagcct   49500
gcagcggctg caggctctgc tacaggacct gggtgaggcg ccagcccca ggcaggactc   49560 aggtcaggac ccctgagggg agaggccaag cacaggcttt cagcagccct gcacccttgt   49620
ctagctgtac ccagccccaa gtgccactcc tgagtcctgg acagccgtgc cagcgggcag   49680
cactcagagt aaatacggaa ggaaaaggcc ttctgggcct gtgcagtgat cagcattaga   49740
```

```
actttctttt gaaataaaaa agagagtgga atccagaaat catgctacta gaaatttgaa   49800
aggcttcatt actaccctgg cctgggctgc ttacagtgcg gccctcacaa tgctccagag   49860 accctttctca cccaacccag ctcctaggga acagagtcag ccaaacattt tccctccggt   49920
cctggagcct cctccagccc tgggacgaac acaccagaaa ccagtgtacg gcatgtcaca   49980
gcttttaaga gaaaagcact ccagatttaa ccatttggaa acctaacttt ggcatgttta   50040
aatgactgtc cccataggtc tggttggcag ccattactta gaaaggagag gatctcattt   50100
ctctgaagtt ccctgaagtt gctctcacac aggcagcctg agaaccctgg gtccatgggt   50160
ctaccaggcc attcccagtg tggaagcctt gtgggtttcc ccagagatgc tcttggcaca   50220
tgctgtacct tggagggacc tgggttcaga gaaagcagaa gaaaaccaac agtgcaggtg   50280
acggtcagtg tggctggcac ccagatgcca tgggggtggc tgcagccagc tgcccaggcc   50340
ctgctgaagg gcagtcatga gcctcgccca ttctggccac atacaaacag gcccaaccgc   50400
cagggtttga gagaagctgg gaatacgggt tccaaggat gggtgcaagt gtttaaatgc   50460
tgctagaagc tagaagagaa aacctctgcc tacactggga gcagggcag gttatcctcc   50520 ctgtgagagc ccagctgcaa tcctgattgt gatctggaca aggcagcagt gcgaggtggt   50580
atgaagtgag atcttaattc cctgcccaga actgaacctg gatatcctgg atgagagcca   50640
gcaatcctgg ccatcagacc agcaagggct agaaggctag aagttggttt tccatggatc   50700
tttgcctctg gtgaaaaatg catttatcaa ggaggcaaaa actgttaatg caggtacaaa   50760
gtttattgag acttagcata acaatgagcg gaagagcaca cagagaactg gtttgttaag   50820
agagaagcaa ggcagagatg cacacccaga gagaacaggt gtgggcatcc ctcttaggag   50880
gagcactgga aaggggcggt taagtcattt atataggtca gttcttccag gtcttttacct   50940 tcagccagtt atctggtttc ttttccacac ctgacctacc ctgagacgct cccttgggtg   51000
tgcatgcacc tctcagccaa gatgaatctc caactgaagg cttctgggag gagcaagact   51060
cattacggcc tagcattatc ccgaatttta accccctgac ttttgacctt tctgtgtatg   51120
tgcagtgtct cccttgtccc aaaagaggga ggagtggaca tcccttaatc ctttactcaa   51180
aacagggttt tgccccttttg tccttgcatg attattacct taaggtgttt aaaagagaca   51240
aacactggct atttaccctg ttgttacttc cattctggag cgcaaatagg aggctagtta   51300
tatgtataca tcctgaagcc cacttcttcc tgccccatga aatgcaaaca ggaggccagc   51360
atctgtctcc tgcctcatct ggactcgaga tgagccattt ggggttctag aggcctcact   51420
atggcaacag cacaccaatc aaatgggccc cttggcatgc accctgagca ccaggagctc   51480
acgggtgagc acctcacttc tgaccactga gaatgtctgg ctagtggaag gaatgaacgt   51540
ggggagcagg gaaggagctg ggatccacag aacaggcaga gacagcatcc tcagaggctg   51600
acccagccag gccccacatc tgcctgctga agcttgttg taacctgcag gactgagtcc   51660
tggcaaagac cctgacccag agagctcagt cctatgcttc gtgccctggg accctgggtg   51720
tccttcccat ttcagaagcc ttgagcccca catggctagc aggtctggcc tgtccacacc   51780
aggctactgc cccagtgggc tgattccagg aagaggcaca tcagtctgca gacaaggtcc   51840
cactgtggtt tcacttggag gacagaagca agcagcagga atggctgagt gtcctgccct   51900
ggggctgcca gggacacagc cgagagccga ggaggaagac tcccaggcgg cccatcagtc   51960
ctgccggggc cccatcagaa ctctgctgag gggtgccatg gaggtcagct ctggtctccg   52020
gggctgtcag cctcactgtc gctgctctga gacagctcca caggactctc caggcggtgc   52080
agctccagga aagtagtgat aagcttggca atgacttcca catcgctggt ccaggccggc   52140
```

```
accaggaggg aggacaggtc accatggcag aggtcctggc ctccagcagg agccagaaga    52200
ccacgccagc ctcctcacag gaactgccct ccaggacccc acaccttacc tggtcccac    52260
cctcacctga ccttagccca ggcctctctg ccactgggga cccctgatgt gcccctcccc    52320
tctccgtccc tgcagggacc cctgatacca cctagcaggt ggtaccatgc ctgtcccccc    52380
aagccccacc tcttccatgt tcctgaagcc tctgccctac cacagtccct tatgagggcc    52440
acttgcctgg gggcaagggc atagtgggca gccctgaccc atcgtctccc atccttggct    52500
tacctgcggt ggcccatgac agcactctgg gtgagagggt gggagaagcc tgtggcgaac    52560
cgaagcacca ccacatagcc cttcccgaag taccggacct tctcctcctc cacattcaca    52620
tcccggatgt cactgagcag gaccaccact gtgggcgggg ccaggtcagc agccatgtcc    52680
cctcccaccc tgcccctctc gcccggatgc tgacacagtg gctttggggg cacagtgcag    52740
agggtgagag cctgcttgtc atgaaggagt gcgtgtcact ctaggtcgga ggcccagagg    52800
atgccgggac ccagctttag atgtcatagg aagtgaccac agcacaggt cctgtgactg    52860
ccggttaaca tccagtctga gtgagaggga acatccagca ggcctattgc cttgaaaagc    52920
ccacctgtct aacacatcag gggctggcta agcatggac tgcccagctt tctgcttcat    52980
tttcctcaac tgctggaaaa tgccttcctg gtctctagtg gccagtcact gagctggggg    53040
ctaccaggca attttctttg ggccagggca catctgggga cacacagcat ccatgaggca    53100
ggacacagct ctggtcaccg agcagccagc ttccccttc caggtcacgc agacgctcac    53160
tgccttccgt ccaccccaga gtaacccatg tcctattcat gccccatgcc ttaccttggt    53220
catggcctgc tctgcagaga gtcagcagct tcctatacaa gctgaatgtc ttcagcacta    53280
ccttcccggt gctcttgttg aagatggctt cctagaacgc cagccacaag gcagtcacct    53340
ggttgctggc ccatgcgcca gtccaataca cgcgaactca ccaactgtgt ccccaccctc    53400
cccagagcag acacaaggag gcagccctct cccttcccat cccagtcaga accctggcc    53460
cctgcagcca gacccctcca ggatctcagg tgtgaagagg agcaggtact tctctccaca    53520
gttgagagag gtgagcactg aggataaggt catcaaatga gggaacaggg cagagagcaa    53580
tattggagcc aggcaaccca aaggcacatg aggaaggaca ggagggaggt gggctcgccc    53640
ttctaggaga acttctagga gagcagcttc agaagattgt gtggcccaca aatggtcaca    53700
aataggcaat gtccaggggc caagtcaagc tggccagaga ccactgggct cacatttcag    53760
gatgggttg agggaattag gcccctggaa tctttcttcc tttgacgagc cctgcaggga    53820
aacccaggag ccccaaagcc tgggcaccct tcctgcatca gcctcacctc ccagtcctcc    53880
aggttctgca cggccacaaa cagacagccc gtgacgtaga agagcttcca gcccagacta    53940
tctggggagc aaacacagga gacagccatg ggcaggtagc agggggcaa aagtcaacat    54000
gcctgcacag ggtgcctcct cccagaacag ctgcttccca gacactcggc aggagtggcc    54060
cctggggcc cagctgactg cccatgcctc caaggacacc ccaccctgc caaggccacc    54120
tggcactgtg ggccctgtca cacaggacag gacgtggtcc accagctctg ccctcagctc    54180
tccacctggg tgactccttg aggttactat catggcacca ggtgtgagag cagagatggg    54240
ggactacttc cagggagctg ctgaaagcat agactatacc tgccacaaga cctgaggcag    54300
acatgagaat gcctttctga acattttgac atgaaaatcc tgatgtaaat gaatgtaagc    54360
tgtggggac acaccagcac acgaaggtga gaccacgcct gcaaaccatt tagaggcaga    54420
aagtgaaagt gttagttgct cagttttgtc caactcctta tgaccccatg gactgtagcc    54480
tgccaggctc ctctgtccat gggatttcct aggcaaaagt gattttccag gcaaaagtgg    54540
```

```
gtagccattc ccttctccag gggctcttcc caacccaggg atagaaacca ggtctcccac   54600
actgcaggca gattctttac catctgagcc accagggaag ccccatttag aggtgggggc   54660
aatccccaaa atcatgcctg tcagattaca aatgacaggg tttccttttt ttctctattt   54720
tccaatcagc taaggaagct cctagggtg gggcggggca gatgacgttc ctcacctcca    54780
ctgtagtagg cagcagccag gccgatagac aagattcctg tggggagaaa acaggtacct   54840
tcccattggg ccaccactag cccagagacc acctcctccc aggacctgca gacccaagta   54900
agcagcccct tcctgttgcc agggatggct aagagcaggg agcaggggt aagaaaaccg    54960 ccaggctcag aagttgtgga agcaaccagg aagtctgttt accaaaatgt tctacatcag   55020
tcacagtatt cactggtcac atgtctttgt tgaggttcca cgcgctgacag gggaaccaga  55080 aagaggaacc tgatgtgggt ttcacccact gacaccacat tgtgtggaat gaagacaaga  55140
ctgcaggtga agagtcccga ccccgcatga gacagaacag gaagagtccc gggaaagaag  55200
gcccagagcc aggctgccga aggtgtagca gcacctcccc tcgtacctca gttcccgaca   55260
tgtgcagctg cccagggagt gcagggcaat ggggattgac agggatagag gaccaggggc   55320
ctccccaccc ttactcctta ctgtctccat cacagaggcc ctgacttaaa tcatatacag   55380
gagactgggt gtatgaaagc aagcaaaaaa ggaaatacag ggacctcaca ggagcatgga   55440
gactattaac caaaggatgt taaatggtga aaaacacaa gactgaccat ctgtacaagc    55500
actcgaaaag gataaaagct ggaaagacat aatagttgct atttcctggg gtagtagaac   55560
caaataaaat tttaatcttc atccttttt aaagttggat ttttaacttg agaaatatga    55620
acatccttac caaccagcag ggaccaggat ctgatgcctg gagccctctt cagatggagg   55680
cgggagctgg tgcgtgtctc cacctgcata tacatccctg aaacctgctg ccaccacctt   55740
caacaggaga ccagggcgcc tggggaagga cacagacagc tggagcccctt gggccactgc  55800 taacagacag gaacccagct cctctgcagg acaagatacc cagctgccca ctaacaaggt   55860
ccacacaggt tcaggaacca gtcagcctgt gctgactgca gtctctgtgg tcaggcaaat   55920 caaccccca gggacccatg tcctctgtaa ggaaggttct ttgcacagat gtaatggttg    55980
cactggggct atgtcccctg ctctggctca caaagcatca acacttgatc atcacctgtc   56040
cacttcctac ctggaaaacct cagtctcttg gaaaccgtta gccccagca gccttcaaac   56100 ttctggcacc ctatcagaac gtaccagaac accctcattt ccctgtatag gcctatgaaa   56160
aagagaactg aaagtctcat catggtttga tgagaggcac tgaccgaaaa agtcagctcc   56220
tgcagctgcg gagacaacag tccgcaccca gcggagggtt tggacggcca ggagcaccgg   56280
cttaatgaac gagtcagcaa aggggactga tcttcccttt gatcagtgga gaattctgcc   56340
ctgcacgatg caatacgttc aaaacgctgg ctccaggggc cccgttttgg gtagcttttc   56400
aggtattctt tgtaaagtta agtcaaattt ctgacaacaa agagtggatt cagttcacac   56460
aaacgaagcc aagatcctgc gatatccccg gctccctccc cttgacatgc ttcgcctgtc   56520
tccacaggcg actcggcccc ccgcggggcg agatcactcc tgtccccctgc aagagccact  56580 taggacactc tccactgacc ttgcggccac actgtgcacc cctctagcct cgagcgctac   56640
caggcccccg gggcatcgac ccgggccgag tcccaagacc gcgctcccgg aaggacctcg   56700
gctgcgggag ccgcccctca gcacacccg tgcccctcaa accgcaaccg tggcacggtc    56760
ccggcgctca cctcggacac aaacctgcag gcgcggaggc gggacgggcg ggaccgcaag   56820
acttcaaaac ccgccggcct ccaacttccg gagctggggg cggaccagc tgacttccgg    56880 acccgcgggg gcggatggga cagtagactt ccagactcgg gggcgggggcg aggcgcacgg  56940
```

```
gtcctcactt ccggggcctc cactctgccc tcgagaggag aggactggcg gggttctaga   57000
atgaggttgg ctatcaatca gtagagattg cggaggctgc cacgggtttt gcgcaccccg   57060
gcgctcagca cagagcgcct ggggttgcag tctttagaag atcagcagag gtaggtgaag   57120
ttgtaagcac gagacagcca tttaagatgg taagaaaacg ttaagtatgt atttaagctc   57180
acaacagata catacaaaca ttagggtaga ttctgtaaaa actttaatgg gaagcattaa   57240
aatagaacta aaatagttgt tcgtggtttg gaaaattatt gtaaaaatgt gaattctccc   57300
aacttgctct gcagattgaa ttgcaaaccc agtaagtgta tcaacagttt gaaaaatctg   57360
cacagcgctg caaggcactg tggaggaggg gagagatctt tgaccccca aaaaactcag   57420 tgtagctggg aaattcacat tttcgtgagg gcagttttc tgctcctcct aaacttgccc    57480
cattgttggg gaacgaggat tgtagtaaga gatcgtattc tccaggaata ccttgaaatg   57540
cccgcttagg tggcctccct gctcctctct tcagtaaaac actcataatg caccgccacg   57600
gcccccagat gaggctccaa gcaggaccct gatttgccta tttcccacta cagaaggact   57660
ctacctgaaa caggagagcc tccaccacac agccactgcc tgcatcagtg gcctccaaac   57720
tgggacagtc aagatgatct atagtgtgct ggaagaacat actagagctt gtattcctac   57780
ttattttatc tttttatgtc tattctcatg tgtcctataa tttacataag atttatacac   57840
agtgtataaa gaaatataca cacatgggca tgcctaaccc tagatgtttt accaatatag   57900
gcacgatgtc aaaaattggg ggatgacttt tctatttcac cagtctcgat gtactctctg   57960
cctgtggttc agaatcacct ggtggggctg ttgaaacaca gaccattgga cctgttcagc   58020
aatggatggg gcttgaaatg tactcatgct agtgcctgct gctctgggaa ccacacccag   58080
agaatttaag ctctgagctg taacaaaagt aggttctgcc tgaatgtggc aggttccctg   58140
atctgatgcc tcatcccaca ttccatttcc ttgaaatgcc ttctgaggta aaatcacatg   58200
ccatcttgaa ggtctatttg aattgcttag cacctccttt aagttctctc tgcttgtgat   58260
cttaattcct tagaatttaa ggagaactga attgataccc agaaaattcc actttgcatt   58320
gcagtccttg acataattta atcttttgta ccagaggaca agccatttaa aaatgaagcc   58380
tacactggct ttctattaat gttaagtgaa agaacaaatg atggctgatt tgattaaaac   58440
cctgctgaat acaggtaaga gcaaaagact ggaaataaat acaaaatcca taaatagggg   58500
actgagtgaa taaaatctat acatttttc cagttatcaa ttgttttaaa ttcaaactgc    58560
attgcccatt ctatgaaaat gcatctgagc cctttttct gtgctctctg gcatgatgtt    58620
aagctttgtc aatggaaggt gttggagaca cttcaagagg aagagttttt cttctcggtc   58680
tggttctgtt gtcctggatc cacagtgcac aaggtttctc tagtgttcag ctcttacagt   58740
acacactggc cagctgtacc cagtatcctc caccttcccc agcaacccat taagtggtct   58800
tgtagcagag tgcctccagt gagattgatg tcaggtctaa agtaagaatt gtacaaggaa   58860
atgtatcaaa aaggagagag actattagtg ttgtcagaag aattcaacag aataaccaaa   58920
tagtggataa gagaaatttc tcattatgga agcagtcctg ctaataaata aagaaatgat   58980
agtattaaaa catcaaccta atgaaactag gccatctcat caatggttga aaattaacat   59040
cacaaaagga caggcactag aactgcctga tgggatttca caataccacc taggaagtag   59100
tctttccctg gaatttccct ggcagtccaa tgggttgaga ctgtgctccc aataaagggg   59160
atacaagttt gatcctggtc caggaactaa gatcctgcta cacttactg aaaattcaga    59220 acaaggatat gctgaggaac tccacatgga tgcagtcagc aattgctgaa aaccctgcag   59280
tcaaacaatc tgagaagtga aattgctcag tcgtgtagac tctttgcgat cctatggact   59340
```

```
gtagcctacc aagctcctcc atccgtggag caacctgatt taacaatgat atgcaaggag   59400
agataggagt atgtgaatgg aacctgcgga tttaacaaac ccccaaaact ttagaactgg   59460
gaactcacta tacaatattt aactaagtga gactaatttt attttttagaa acaaaatttt   59520 tgtaagagaa acacacaaac caattgaaat acagactaat aaaacattga accttattta   59580
gatccagatt gaaactaaaa tgaagagacc tttggggaaa cctggacact aactacacac   59640
agcccaccag gcttctatgt tcatggaatt ctccaggcaa gaatactgaa atgggtagcc   59700 actcccttt ccaggggatt ccctgatagc tcagttggta aagaatctgc ctgcaatcta   59760 ggaaacccccg gtttgattcc tggatcggga agatctgctg gagaagggat aggctaccca   59820
ctccagtatt cttgggcttc ccttgtagct cagctgataa agaatccccc tgcaatgtgg   59880
gagacctggg ttcaatccct gggttgggaa gatcccttgg agaagggaaa ggctacccat   59940
tccagtaatc tggcctggag atttccatgg attgtgtata atccatggtg tcacaaagag   60000
tcggacagga ctgagcgact ttcactttct tccccttctc caggggatca tcccaaccca   60060
gtgatagaac ccaggggtct ccttcattgc aggtggattc tttaccatct gagccacctg   60120
ggaaacccct tgatgaaatt aagtaattgt aacttgcctt ttccacacat gatgatattg   60180
cattatagtt ttaaacatt aacaaatat aagtgacaac ctaaattctt ttatttaagg   60240
tgataactga aaatgtttc ttttttaagt aattaatttg gctgtcttgg gtcttagttg   60300
tggcatccag gatctttcct tgagtcacaa agactcccca gttgcggtgc atggacttca   60360
gtcgttgggg cacttgggct tagttccctg accaaggacg gagccagcac ccactgcact   60420
accagacaga ttcttaacca cccaaaccac cacggaagtc ccttgaaaat gttttccaag   60480
aggaggtgct gacatagatt tgaataatac aatatattaa tctgacagcc agataggacc   60540
tcctgaattt aactgacagc aggttgtaaa agagcgtatg caccaaaaac tataattaaa   60600
aaaaaaaagt tttaaagggg aatattttaa ggttttgaga cttggaatac tctcaaatgt   60660
tttgctgacc tgtgaccccca cccccaggtg aggagggaga aatgtccatt cctgagattc   60720
ccctgataga gacaccccag tgctttattt tccggaaagg cgcagttctc atttccgatg   60780
gtgctgggat gaccatgcac taactacata aaatgttacc aggggacaaa gctcaacgtc   60840
atcatttggt cccgcatcca ccttgatttg ctagaggtag cgtaggagaa ggaaatggca   60900
actcactcca gtgttcttgc ccggagaatc ccagggacgg gggagcctgg tgggctgccg   60960
tctctggggt cacacagagt cggacacgac tgaagcgact tagcagcagc agcagcgtag   61020
gacccaggtt tggcgaccta cgcttcacac gttcctcgcg ctcccgacgg cgccacccgc   61080
tcctgacggc gccacgtgct cccggcccgc cgcgcgtgcg tactgcctcc cgcgcggaca   61140
tacgtgacgc gcctcggggc ggaaatggcg gcggaccggg gcggcgccgt ctctaccagt   61200
ctaaacctgg aaggtggtgc gggcctgacg ctgagctgac gcaccagaac gtcccggtaa   61260
cgatctcggc ccgcccctg gggtccgtca gctaggctgc tcagagccgc agccagactc   61320
acacgccgcg gaaaccttcg gccacggcct ccgcaaggtc ccgacggggc gggccaagct   61380 ccgccctgc gcgctccgac tggctctagg tcccgatttg cccctttccc gcgttgtcat   61440
tggcctaggc agagcccagt agcgtggagc cgcaccgctc tctccgcgct cctattggtt   61500
cagggttgta gcgcatccgc tcccagagct ttcattggtc gagccgagcc actaggggta   61560
gggcagctct ggagcgacga caacaaaggg cggcaggcgg cggtgaccgc gtctcccggt   61620
gctctcctca ggctgcgcac ccggacctgc ccgcctggct ccagatgaag tgtgagcact   61680
gcacgcggaa ggtgggctcc acgcttttgg tccggggccg ggctggggc agggcccggg   61740
```

```
gcgcggagga gcctgagctc gcggagcccg gagccttggg ggtgtcagga gcttggcagc   61800
tccaagcgcc tctgcctccc tgtcagaacc tctgggcgct ggcccgcagc tcgactttc    61860
cgggggtgga ggcggctgag ggtgggccac caacgcgtcc ggttcctgtt ccgtgtcctg   61920
gaggcggcag taatgtcggg gcgcagatac agcctttcaa agtaccttag aagccaaaag   61980
ccgcgagaaa agcctaccaa catcagcgac cagtccacag tcgttgcaga caccgtcctt   62040
ggtgtgaatg agggacacgg tgatcaaaag tgattttagg ggattttatg ccacctaaaa   62100
actttcgtgt ttgacagcaa cgaaaacgat acagaagtgc aagaaggaaa cgggctgggc   62160
ctcctgccac ctgagtaacc atagtaactg tgatagcctt atccacttgt ttctacgctg   62220
taatgcacag ggagttgtct gttggttttt ttcaaaattc gatcctatca tattgttcca   62280
tcacttgctc tttctctcac ttaatgttat gcaagagata cattttctga gcaatacaca   62340
cagtcctaat ttgttgtatt ctaaatatac acgcgtccag gtggtcgggc accaatttac   62400
ctgtcatgag agaccacatt gcttctagtt ttcatttcct gcgaaccgtg cacatacaga   62460
gatgtgtatg ggtgtgtttg tgtgcccaca attataagtg cttctatttc tgtagaaaag   62520
atttctagat atgaaatgaa ttcatcaggt agtatatca  gttttcttag attaaaagtt   62580
gttcttttat atgtgccttt gccttttcaa ggaatgtagt aaaaaaacaa aaaccgatga   62640
ccaagagaat gcatcagtcg atgtaccaag tccagcccag gagaatggag aggcaagtag   62700
tttttcagtt tttgtgtcaa cctgcagtaa acagctgctg ctgttttttct cctctttggg   62760
ggctcatgtc accaggtaca tctttgcttc aagaaaaaaa ataagaaatg aaggggccaa   62820
aaaaccctg  ctaggggcca acatgcggg  ttagtcagtt ggaggcacac gatcttcaag   62880
gtaagaacat tttcttctca gagtacacca agccaaagca taccatgtta ggaacaaggc   62940
aaaatgtcat ccttggctgt ttttttagaa atagttttgt aacatttaaa cctctggttt   63000
tctgggtttt ttttttttt  ttaagtgaaa agacagggct ttaggtagga ttttataaaa   63060
taatttggat ttcatgattc tgtaagtttt attttttctac tggtttcttc tctaagttct   63120
tgagtttttta agttttttctt agctagtagc gatggtttac atttattgga cacatactct   63180
gagctaggca gtcgagaaag tgctttgtac atgtgatctc atgccgtgcc tagaatgagc   63240
atttcaggta agccctacag ttgtctccac tttacagaag gggacgcagt gctgggaggt   63300
taaggttcct tcttccctta aaaagttctg gtcccagttt tagaaaggga gaattggcaa   63360
cattggagaa gcaagcagca ggtgtcctct ttagtctagt ggttcccaat acaacattga   63420
gtcagacagg cattggtctg gtcctcttgt gtaccagctc tgctctgtgc tctggtgaat   63480
gtagggctta gtgagcagta ggggataaga caagcacccg ggacactgag gcagaagaga   63540
ggcagggagc accgagggct ctgcagcctc agagcagctg gcccggggcc tcccatgcct   63600
gcactctgtc cgcactacct tggacagaca tctcaccctg ggagcccag  tttccttatc    63660
agtgacatgg ggagttgggt tacttctctc cgagggccat ggtggccagg agataatgtg   63720
tgtacatagc ttcagtgggc atccctccag cacagtgggc ggactccctg acaggatgaa   63780
caggtcagga aggtgactac tggagtgggc cctgagggtg atgagacctg aaggtggtgg   63840
gtgtgggaat agggtgaagg cgcaccaggc acgggaaggt gtgaaaggta aggagacaga   63900
tcgggcacat gtcttagggc tggtggctta agctggctag agtcgggaa  gaataggaag   63960
gaagctactt gggaggccaa gggtggtggg cctgtatggg ccagccagag tggcggaagc   64020
aggaaagggg gagcagcaca gggagcagag tgcagtttga gctgcatgga cactgcagga   64080
tgtcagactg gatattggga gggagagaat ttcctagagg cagagattgg aggggttgag   64140
```

```
tgggggcctg ataactgctc tgagaagtgt ggctaattgg agagaaggag agatggacag    64200
gcttctgcag aaaatgccca cgattagaac ggaacaagag aaaggaagga ctgtgacagg    64260
cgggaaggaa ccagacctgg cccatgaggg gctctaggag gatgagcatg gggtgtggct    64320
agcaggccga gaggaagccc tgcttcccct ggcagctcag agtgttgtcc tgggcacctc    64380
tacagggcca gcggaggcag aactctcagt gcagctcaac agcgtctatt agacgccggc    64440
tgtgtgccag ggcacgtgct tcagacccett ggagcagccg ctctggcccc acctcagggc    64500
ttgttagaag gcagactct tgcctcccat ccatacctca tgaattagca tctacagcat    64560
aacaaggtcc cagagtgagc actgcacagt gacacaggcc cctggggagg agggaggtgg    64620
cagcgtgcat tcctgttcgg cactgctgtg gacaggaggg ccagcctacc gcccgagtcc    64680
tcgcttacca aatcgtgttt gaaagagcaa tgtacagcaa ccgtcagatt tcattaattt    64740
gttgcgatgg ctctaacggg cttcagaata ttcgtatgtt catccaccac atatttatca    64800
agcgccttct gtatacaggg gatgtcagag aacagaaggg catgagacaa ggttcctccc    64860
tcagagcttg tgtttcaggg aaaagagcca ccacataggt gccaggggt gctcagagct    64920 gttctggcag gtgtccatga gggtctgagg gtgaaccagg ctctctaggg agcgtttccc    64980
tcagggagac tcagggcaag gagggccagg gtgactggaa gttcgagtgg ggagagtgat    65040
ggggaagggg acctccagca gcatggtgtg gcttgtcttc tggtggacct cagcccaggg    65100
gagtgggctg cagggagcga gggcgcaggt gcagtcaggg gaagacaaag cagccgaggg    65160
ttgtcatctt ggtgtccagg ggaacagagt cactgagatg tgagtttgaa tgttccaact    65220
cagacttgga tgacgtgaca accctgatgc ccacaggtca gcactgagct atgccagttc    65280
taagcctgtc agggaggctt ctgaggagag tccaaggact aagcgagctc atcggggagt    65340
acagagcagg cccacgcagg agcccccaga ggcagcaggg agggctgtgg gggcaggaga    65400
agctgcattt gatggtgccg gtccactccc cacacattgc catctgtggg accctcagag    65460
aatttgtggc agttttctgt attatgcgtg tgctgttact ttccctcaag aagccagtat    65520
taaagagttc tgttaaagaa tcagaccata acatcatctt ttctttcaca gaagggagaa    65580
ttccataaat tggctgatgc caagatattt ctgagtgact gcctggcctg tgacagctgt    65640
gtgtctgcgg aggaaggaat ccaggtttcc cagcagaacg ccaaggactt cttccaagtt    65700
ctgaacctta acaaggtatg gcatcccggg cgctcactgg caccagaggt ggctggaggt    65760
caaggtgagg cgtgaagcct ctgctgggac ttagggagcg catcttggcc ctggcttgtg    65820 tccctgtga tagctgaccc tctccacagc ctctccctgt caacaaaacc ccacccacag    65880
tcacactgcc tcactgatgt gggcagcaac tgtggctggc accaccagcc aggctcccct    65940
ggctcggggg aggcctccgc gtgcttggtc atgggatggc gtggcagccg agctgctgct    66000
cctctgcctc tggggctttc tcagaggtta gggccacagt ccttcagccc attcctgcag    66060
acccctatac agatgaacta tccgttcctg ggtgaagaca ggtgaaaggg aaagacggag    66120
agacggaggc agatgaggct gaaaagcgtg tcttggtttg ccctcagtct gacctggtga    66180
gccgccctca cagctgtttt ccagaaagtg tttgtacggg ctctgaacac agtgctgggt    66240
gctctggccc atgtggcagt gcaggtacca cgtgaggccc aggttgcttt ctgggtgtac    66300
tgactgcaaa taacagattt cattcttcc aacctgtata catttattt tttctgatgg    66360 tatggtctag tacctttgga tcaacctgaa attacattgg tggtaaaaat aataccacca    66420
ctatcttgtt tccgatttca gtgggaatgc tggtgaagtt ttactattaa atagattttt    66480
gcataatctt ttactattaa agagatgtag atactcacac caatcagcat atcagctata    66540
```

```
gaaaatggat acccaagtca aactagacta aaaaggaaat gcttagttat ttcatgaaac   66600
tgaaagctta ggaatggaag aggttctgag tttggctgag tcagtcattc aaggctgcca   66660
caggaaaaag cagttcctat ttctctgctg gccgtggggc tctggggttc ctgagctctg   66720
gggctcaggc tgacctcttc gtcacagatc agctccctca gaggatgtga aatttaagtg   66780
agaatgaagt gaggggtgag cccttgaaat tccctgggca gggtgtcaga cagagggact   66840
ggaattgccg agtgtgactg ctgaagctgg ggacagacca ccctctgtcc ttcccccttc   66900
attagcattt gaaatttata ctctctttcc tgcttccaaa tttacattag gatgctcttg   66960
gtcacaaacc acagaaaccg tgcctggctg atttgggcat cataggaact tgtcagggag   67020
ctggaggtca gtgtatgcca ggttggtgcc ctgatggccg tgtcggtgtg gcttcccag    67080 gcatcacgtg aaggtgggag gggaccatca cgtgaatcca gagggacag gcagcctcag   67140 cattgtctca cctgagctgc taggcagggg caggcagacc ggaccagact gtcctgtctg   67200
tggccagtcc ataggtagat tgcagtggat ggtagccact gaacactgct gtccaagttt   67260
ccacttttcc taatgtgcag gtggtgtctg acctgaacac cctctgtcat gataatcctg   67320
catcttctgt ctgaccccag gccagggat cccactgctg actttctaat gcctgacatg    67380
ctcgctcaca ctgctcccca aggttgcatc ctgcatgtcc gtaatgagtc agcacgcctc   67440
tgaactcaat ctgttcatat ttttctaggg atttcttgaa ctgccagcat ctggttttgg   67500
tttcagggtg ttgataggct ggtttcacat ttgtttgttt ggtatttatt agaagaattc   67560
atagaagatg agaattatct atgacttaaa attttgctaa aatttaccac taagtgacct   67620
gggcttgagg cctcttgtgg acagacctcg gggccccatt tttatgtaac ttcattgtta   67680
tggatcgttt cagttattta tgtacctata aataataagt gtattttat ttttcctttt    67740 aagtgtattt gttttatcaa gatatttgca tttatatgta atattgatgt atatattcag   67800
tatttctgat ttaacattgt tcttaaaatt gacaaaatct cttgggatgt ctcattttc    67860 attctaattt tttttctcctt tttcctcaat tgtgcttgcc agtatcctgt gtattttatt   67920
agtctttcag actaattcag actaatttca gactaattca gactaattct ttcagattgg   67980
gcatctgtta cactctgttg tagacttttc atacaagtgt cttactttca ctcccttgtc   68040
atcaccacat acacggtgtt cctctctgtt tctcctagaa atgtgatacc tcggagcaca   68100
aggtgctggc agtgtccctg tgtcctcagt cttttgcctta ttttgctgct aaattcagcc   68160
tcagtgtgac tgatgcatcc agaaggctct gtggtttcct caaaagtctt ggtgagctgc   68220
cttttgatat tatttatagc aaataaattt ggtataattc gaatttataa cttgagtttt   68280
tatctgccct ttttatctct agagttcaat tttcaagggc acaggataga taagaacttc   68340
cttgagaatc ttgtggaacg taagaggacc atgcctctga tccacgtatg gtaggcaggt   68400
gtcacttacc cccttgccat gcagatgggt gttgtcttac ggccggcgct ggcccctctg   68460
gggacagcaa atgactgtct tagggcacgt agctggggac acctgggacc cacacttgcc   68520
cagcagtgtc gagttgctcg gctcacaggg gttacagtta tctgatggag gatcacgtct   68580
gccgtgactg gcgtctgatt tcccaggaag ctctgaaagg cagagcagga agggaatgga   68640
ctgtgttcct tgtgtgaaga gtgaaagcta gtcatttcag tacctgagga cgcaaatgtg   68700
aatgagtact agagtaacac tgcctcataa agagcggtaa ggttgcttct gtctagtctg   68760
tcacgtcaca ctctaacttc ccccccaaat taaagtgtcc tgcagggagg ctctgaagag   68820
gaaaacttga gctgtttgcc aagtaagagt tttagttgtt cctcaatggc ttttaaaga    68880 tgtaaataca tgaggttagc agtaagatga cccgtagact aaacgtcctc gcagcagcct   68940
```

```
gcctgcctcg ctgctgcatg ttgccttctg tgcagagcta tttcttggtg cacggcatgc   69000
cacaaccagc actacagccg cagctgcaga cgaggactcc ctaagtcagc cttcacgctt   69060
ctaatcttaa aagcctaagc ttagctgagt tttaccaaag atcagagttt taaaatgctc   69120
tgccttctca tagtgaaagg ccctattttg gagggggggag attttttttt taatagttgg   69180
atgttatatg ttaataaaat atatccacag tgaaactgac ttttttttaag gtaactcttt   69240 aacttgatat aatatttctt tttaagaata actggctgct cttaaggttt agactggttg   69300
cagatattaa aactatttgc tctatttact gtaattattt aaagcatatt tttttgtctg   69360
aggcttattt tccaatatta agaactcatt tgtagcaaca taaatgaact tggtgggtat   69420
gataccacca tatgaaatga gtcagacaga gaaagacaaa tactgtatga tatctgttac   69480
aagtagaatc taaagaaaaa tacaacaagc ttgtgagtat aacaaaacgg acaaagacag   69540
atgtagagta caaactagtg gttaccagtg ggcagagtgg aggggcgtga cagaggtggg   69600
ggattaagag gtacaagctt ttaggtataa aataagctac agggatatat tgtacaacac   69660
agggaatata gcaaaaaaaa aaaaaaaaaa ttgggggggc cgcgccatga gacctgcagg   69720
atcttattcc ctgacaaggg atcacagctg ggcagcagca gtgaaagcgc caagccctaa   69780
ccactggaca accagggaac gccctatagc aaatatttta taataactat aaatgcagcg   69840
taactttgaa aaattgtgaa ccactgcttt gcccatctgt accttatact gtatatcaac   69900
tgtagtttaa aaataaagaa gcatacattt atcaagaaaa agacaagtta gaaatttccc   69960
tggtggtcca gtggttacga atccgccttg cagtgcaggg gactcaggag cgatcccgc   70020 gcagggaact gagaccacat gtgcctcaga gtaattaagc ccgtgcgtgc aactgctgaa   70080
gcccatgcat gtgccctgga gccctcgatc agcaactact gagctggtgc agcacaacta   70140
gtgaaaaaga aagagaagtt agaactcaac atagtaatta atcaagacca ttgtaaagct   70200
atgctcagcc agtgtcctca tttatttatt ttagagctat caaagactgt tacagactgg   70260
agtttaattt agccagtgaa ttggaagaat gatacccgt aaaattacat taatttatgt   70320
atggaatatg gcaaggtgtc tgtaactata gatgtaaagg gaaagaaga acaggagaa   70380 tatatgcttt attgtgaaaa gtgatacgtg ctgttgtttg agagagcaaa gggcatcgtc   70440
ctgcacttgg gcatctagct atgtctgtgg agtctgcctt tcagtttgt cttcgaggcg   70500 aactgagggt cgatctcaca ttctgtgatg tggagcccaa cacgcctctc ttccccacag   70560
gggtgcatta tgtctttgat acaacgatcg ctgcagattt cagcatcctg gagagtcaga   70620
aagagtttgt gcgtcgattc cgccagcaca atgaggaaga gcctgcgtta cccatgctga   70680
cctctgcctg tcctggtgag catggggctg ctgctgggtc tgcaggggcc tgatgcacct   70740
tttctcgtca gtctgagtct gggggcaggc ctgggcaatg ggtgaggtca ggggcagcgg   70800
gtcttggaga ggagtttggg ccttgagtag ttttatgttg accaacatat ttattaattc   70860
tgggtgattt agtggggaga cctgacagct gagtattaat tgcttacctt catttatgca   70920
tatttctgag acaaacatat catatgttaa aggagaataa atctcttttc aaagtatgat   70980
gtgtttcaca catccaaaca attataggta atatggtgaa cacccatgga tcctttacca   71040
gcttaaatag aaattacata ataaaaaata ttactttaca ttaatactag attctgtctt   71100
ggaacacttt ttaaacaaat ctttaattat tatatagagc ctgatatctg aggtacagaa   71160
attttatcac aggttttta attctgaaaa aatagaaggt tttggaataa gaaaattcta   71220
aagatgataa gggaaggaag gctgtgctat actggtaagt aacatttagt gaaaaattat   71280
ttctaaatca atcaggtcta tgagagttgt ggtctactta atcttggggt tttgttcaca   71340
```

| | |
|---|---|
| tttccattct cagtttatcc ctcccggttc cagattttc tagcatttta tatgtcactc | 71400 |
| atcagtcatt gggattatga gttagtaaga tggaatgttg atatatggtt gcttagaatt | 71460 |
| tggaaatact ttccatccac ttgtaaaacc atggagagga aacttgccat ctgtctaaga | 71520 |
| agcacgtgga tcgactcatt aactgagcat gtttttcagt ggcccacagg ctggcaggag | 71580 |
| gtgctcagca tcaggtgggg cttatccttc tggaaagata agcccagggg gatgctccc | 71640 |
| acttctccag gcatgtcagg cagtgactgt atcagggtct acgcagaaac tgactaaaag | 71700 |
| cacactttgc tgggccatgg tgtccacctt tgtgtttatg tccttgtagg tgtttgcaca | 71760 |
| gctgctgagg agtaggtttg cacagcggag gcctcgggga accacccagc tccctagagg | 71820 |
| ccttgcagtg gtaccctgc ctctgggtc ccagcaccgg ctccttgcag ggctcttact | 71880 |
| caatggcaca cacagctggt cactgtggct cagtcccacc cacccaagaa agaggcagca | 71940 |
| taaaatgacc caagctcagc ctgtgccccc agagcagtgg ttccagaatt cccatccacc | 72000 |
| ttccagtcag caggatcaca gggattcctg tgctgtcctg acaccacccc agcagatagt | 72060 |
| gatggatccc ttacgtgggc agccctgttg gatggcgcct aaacgaaagc ctccactcct | 72120 |
| ggcaggaact agcaccgctg atgtgggtag tagacaggtg gtggattctt gtggaaagca | 72180 |
| cgagccgctc tgtccaagga gtgagggcag cgctggcgga gacctgggcc acctgctgct | 72240 |
| gctgcacacc agctgtccct gctccaccag cctggcattc gctgctttca gtggcctcct | 72300 |
| tgagctcttc agggctctca gatgattagg cttctcctc caggaactct tgtagctaa | 72360 |
| gccagtcgaa gctgtaactg ttcaggctta tgccccctct caaattcagg agatgaggt | 72420 |
| gagatctgct tcgaaactaa cccttttcta ggatttggcc ctgacgtttt gctttcctat | 72480 |
| gacagcttag agaaattaaa gcagcatcaa ggtcggatga tctgacctgg tgcagaatcg | 72540 |
| ggctgttgat ggccctggac tgactcacta gcttccgcac gcaggatccc tgtgcttcct | 72600 |
| cagactgctt ggagggcagc gcatcctggc tttgacaggg acatctgggt gggcccttgc | 72660 |
| tgcccacaag ccgatggagt gccacctcgc cagcgcacct ttgcctggtg ggggtgggtg | 72720 |
| ggcgagggcg tattgagctg ctcagctgtg gacgtgctca agggctttgg gctttgtgag | 72780 |
| aacctaccag gagcactcat tgaactggag tgtgggaagt aatttctcca atccagcagg | 72840 |
| gagaatagag agtgggcacc ttgtgccagg cacttcttgg agcaggtttc ttctctgcct | 72900 |
| tcagagaggg tttctgagaa aaggtggctg gactgacaga gcaggacaag ggtaccctgt | 72960 |
| ccacgctatg ctgccacaaa gctggacggc cagcagggct gaccaggccc caggctggtg | 73020 |
| ccagtagcaa gttctgatca ggggtaccag agcgcttgcc actctggtct cgtgccagtg | 73080 |
| ctgtggatcc tgtgacctgg ttcttcctcc tcatccctgt ttggtcctct ttgcttgcaa | 73140 |
| gctaggaggt cccccagggc ccttgccact accagcctgt gttctgcctg atattgtgcc | 73200 |
| atgccttcac ggcacacagc ctgcagctgg ggtctgcctg agagccgagt gtgcaggcac | 73260 |
| caagaccagg gtgcacaggg gccttacaaa gccagacctg tggtgggaat ggccttgggc | 73320 |
| ccccaagtgc tccatggcct ttgatagttt tccttttcc ttttatttat ttattttggc | 73380 |
| catcccatgc agttccctgt ccagggattg aacccagggc cctgacagtc agagcagtga | 73440 |
| gctctaacca ctggacagcg ggagaattgc ctagttttct gttttaacat gaaccattcc | 73500 |
| atgcacacgt gcagaggctg ggaacgaggg gagccatcct ccagcagcat ctctctgtgg | 73560 |
| ggcttctgct ggtgacagtg gacattccct gcgtgtactc aggccggcaa gcgggtgata | 73620 |
| gctgtggttt gagttcagat gagattgtct ggctggtgcc tgctgctcca ccctacagga | 73680 |
| gtgggcatgg ggaggtgggc tgccctgggg atctggtggg cagcgtgcct ccaggtttgt | 73740 |

```
tcaccatccc caccctcctc atgaagctgt ggtgtacgtg ccagtctgtc accagacact   73800
ctcattacct cacccagcgg gagaaggggg cgagctgtag cccctgcagg ttgagctgct   73860
ggctcggtgg tccactggcc tctccatcct gcgtcccctc tgggacccat gacagcagtg   73920
gtgcactcag agggcatggt gggagtcagc agctcagggg aaatgcccag gaccacgctg   73980
ggcatgccgt gggcacactg caggttgtgc tgttcattgt gttgcttgag ggggtgtggg   74040
tttctcgtat ttcattgtcc taaaagtggg aagttactgg gtggttaaat tccaatagat   74100
gagtgacgct tggtgggcct ggtggctgtt ggccctctc tgagctgtgg ctgtccatcc   74160
cggctgtgag agcagctcag cagctggcag ggtggatctg gagccaagct gcccaggaca   74220
gtgcctcgta gctgctcctc caagcttgtt ctcaatttg gggagcctgc tacccccgct   74280
cctgcctttc tcctgctctg tcctctctga tctggggccg agggaggcac ccatcccggg   74340
caccctccag tcttgtgaca catgcccctg gggttcccat ggccaagcct ctgaagagag   74400
gcggtttggt ggagggagcc tgtcatgcac gcctggggcg ccggaagat gagatgtccc   74460 ggctgtactc cggtggggca gccgtgagga gctgacatgc accccttccc tcctcaggct   74520
gggtccgcta tgctgagcgg gtgctgggtc atcccgtcac cccccacctc tgcactgcca   74580
agtctcccca gcagatcatg ggatccctgg tgaaggacta ctttgccaga cgtcaggtaa   74640
gctggccttt tccccaaggg cagcattcag gtcaggcgac aagcttccat gtgaggacag   74700
gtgctgacgg aaccgagggc gagcaaggga gggcggagga gggtccccca ggggtgtgca   74760
cagtggtctt gggcccaggt cctgatgagt gaggggggtg cccagacacc tagctccaag   74820
acggtcactc agctgccagc tcctggtggt gccagcgatt ctggctcagc cgggacatgg   74880
agaggggcag cctggttaca tgggaagcgt ctggaaagtg tggggaaatg ccaagcgct   74940 catttgcggc agcttgtggt caccgtgtgt gatcactgtg cacttggttc agggaaaca   75000 ggcggcaggc ctctccctga gcgtccgggc agtgggcctg cagcacggcg acaccgtggg   75060
tggacttggg ggcatcgcgg ctcaggaatg tggtctgggg gggatggggc ttggacccag   75120
gaaagcacca ggcccgttcc gttctggctg ccttctccct tctacacggc ccccatcatg   75180
ggtgtgctct ttctacacag aacctgtccc cagacaagat ttttccatgtc atcgtggcac   75240 cgtgctacga caagaagctg gaggccctcc aggaagacgt cctcacagcc tctcggggtt   75300
cccggggcac tgactgcgtg ctgacctcag gtgagggcgc agcctcggga aaggctgctg   75360
ggaggccggc cggcgcgtgt ccagaatgag ggcctgacag ccacacccac actggagaca   75420
cgtggagctt cctccttcag agcaaagcat aaagcacacg cgtccccggg gacgctgctg   75480
gcgtcttaat gtcccttctt tgcttgtagg tgaaatagct cagatgatgg agcagagtga   75540
cgtctcagtg agagaggctg ccctggacac gctgtaggtg cctctgcagg gagggcgct   75600 cttgcacctt gggggcttcc agcatgacct tgtgacctct accaggttat cccaggacct   75660
tcctcctcca tgaggccacc tgctctgctg aggcacgggt gtggtattgc ccctggtgtg   75720
gcgggctacc ttgtcgcccc tctacaaccc ttggctctga agagcatg gccagtacca   75780 tgctgagtgg atgccgttca gcctgtggtc tggtgtggat accaacaccc tccttcccga   75840
cgtcacacct gggccctat ggggtggagg cggcatcccc acacagtggc tccctcaggt   75900
ccctttgccc aagagcagca gctgggttt ctgccatcag cggtcgcccc aaccaccagc   75960
cacactcctg ctgcatcctg tgccccaggg cacggacttc atggcaggtc ctccaaacag   76020
tgatgtcagg accacatgtg gaaggcggac tgaggtcctt agaacataag cagctggtgt   76080
ccttacggcc agagcccatg cttgggccta agcggaccca acagtctacc cctggctggc   76140
```

```
cacagatggt ggcattctct cttgtgtgcc tcagatgccc agttctcatg ctccgagttc   76200
tgaggttctc agggttgagc cttgacacct gtgcactcag aggagtcact tgggcagcgg   76260
tgggcatgct tgcaggcttc ttgttggcca gtgaactcca gcacagagga ggtttttgcc   76320
caaagtctaa gtacttgtaa agggttttgc aaccttggat cgtaaaactt ggagagtcgg   76380
atttaacttt tgccctcgct tttcctgcct ggtgaggttt ggcgacgtga aggaggagga   76440
gctgaggcgc cacgatggag ccggctctga cgggtacctg gcacacatct tcagacatgc   76500
ggccaaggag ctgttcaatg aggatgtggg ggaggtcacc taccgggccc tgaggtgcgt   76560
ggggctgggg cggcctctgt ccgtctgcct gtgtggtcag cactgcctgt caggtataaa   76620
ctgtgtaata ggaccccgc cccccacagc cagctgcagg tctgagggga gatcctattt    76680
atagagttca caccggtcaa gatcgaaagg ccttggatgt gttaactcac agacttaaat   76740
tttgctaaca tccctaactt agattggaat agtcctccga ccacagagga aggacccgt    76800 gggtcatagt ttgtattgtt gatttcatag gaacaaagat ttccaggagg tcaccctcga   76860
gaagagcgga gaggtcctct tgcgctttgc tgcagcttat ggctttcgaa acatccagaa   76920
cgtggtccta aagctgaaga agggcaagtt cccataccac tttgtggagg ttcttgcctg   76980
tgctggcggt aagactcgag aggccaggct gagcttggcc cctctgagcc ctgcaggaaa   77040
tgaggggtga gatgtgaggg ccagagggta gccattgggt gcggccaagg ggtcagggga   77100
gagaggttgg gaaatttgct gcaagttctt ttaaatgaat ttttatttta gaaatcacat   77160
tatctacacg tttgagaata agtagcacag atggcgctag tggtaaagag cccacctgcc   77220
agtgcaggag ccgtgagaga ctcgggttca atccctgggt caggaacatc ccctggagg    77280 agggcatggc accccactcc agtgttcttg cctagagaat cccatggaca gaggaacccg   77340
gcgggctgcg gtccatagtg tcacaaagaa ttagacatga ctgaagcgac ttagcacgcg   77400
tgcacacgta tagcactagt atgtagaagg catgtccttc atgcagtccg aggtgtttgg   77460
gtttgggtcc cgtgtggctc atgggtcccg ggccccctcc ccgatgcagc ccacgtgtgg   77520
attcacacac taaggcttta tgcagacacc agtgatctag ctgttcatta atactttctg   77580
tgctctcctg gttttgatga attccaagag aaactggaaa tccagatagg cgtgcatagc   77640
catccagttc taaaaggttg ccaagtaatt tcagctttag gtaaaagcat ttcctgggta   77700
gtataaagag gagagaatag gaagcacctg gggttgtgag cctgtgcccg gggtcttggg   77760
gcccaggctt tggccacaag acactgcaca ctgccatcat tgctctgctc ttccagaatc   77820
gtctcccctt taagatgaaa gcaggggaag agtaagctcc ctgtgttttt caggatgcct   77880
taatggcaga ggccaagccc agaccgcgga cgggcgcaca gacaaggccc tgctgcagaa   77940
gatgaaaggc atctacgccg acatccccgt gcagctcccg gaggccagca cccacgtgca   78000
ggagttgtac caggagtggc tggatggcac cgactcccc cgtgtccagg aagccctgca    78060
tactgcgtac cagggcccag ggcagcccgc tgacagccga gacatcaagt ggtgaagatc   78120
gaggagactg ggaggcaggc ctgtcagctg cctgaggaca gaggagctac cctgtgtggg   78180
tatcagagac acctgaagaa aacagctcag cttttccttt taccactttgg tttttcagaa   78240 tcctctgcta ccccccatttg tcagcagccc cctccctcag ttcgatgtgg tgctatcttc   78300
gtaatatgtg tgtaattgga atattttaac aggagagaag ggttgcccca atctgagttt   78360 ccttttaagac taaaaaattc caaagaacaa gaatggagac agactactgt cttttaggct   78420
tgaaaaaaaa atccaaaaag tgtcctgtga agagttaaga cccagaagt tgtgattcac    78480 atacctcaga gatttgatgt ggaaatgaca ggaagcaggc aggccgcggg ggttgtgggc   78540
```

```
catggtctgt ggtcttccca gttggctctt gttttacaa accacgtttt ttattcctga    78600
gaatggtttt gccagaatgt gaataaactg catccttttg gagtcgggga gctcatatga    78660
atctggcttt tcagtttctc tagagaaaaa gttctggcaa cagtgggccg tgtttctcac    78720
tgccgcagtg gccagattgc agtggcagcc gctgcctggg accagcccct ctaactgcgg    78780
gcctggcagg ctctggcagc ttataccca cactcatgct ttcacattca gtctttaggt    78840
gaactcacct cgaagcagag ggcggcctgc gaagggtgac aggtgttaca catggaagga    78900
tggtagaggc agctgacctg cttaggccaa actggtcagg agtccgcctg ctccattctt    78960
ctctgggtgg gatcagacag gtgacagcca tcctgtcccc aacctcagat gaggcagctt    79020
ctcaatggtc ttgcctctcc ccgccgcccc ccacccacc atcctcctca cgtactgtgg    79080
gccaggctca tccacgtggc tcctgacggg acccctgccc ccacccccca aaccccgcc    79140 acctggcatg tagtgctcat gtgagcttgc cttaaaggta aacggaagag aacagttttc    79200
ccatgaacag aaagggctag caaagaattg gaaattacag aatcacaaaa ccatatcagg    79260
gctcatcctg tgaaacgaag acgtctgtgg ataggcctcc agttgattct tcaaagcact    79320
tgaattttgt taacatggat ggtagcagcg ttcttggatt cctcagtgct tatgaagcct    79380
gagctgttag atttccttca ctgactctgt tgtattgtac ctgtatacct attggggttg    79440
aaaactggat atattgtgtg aaattgtata ttttttgctt tcaacctatg tacaattaat    79500
tgggtttctc tcctctgcag taactgatga tggaataaac acttgaggag tgtctgagtg    79560
tggagagtgt gtgaaccaga cactgactcc ccagtcaggg gcctgtgtgt gccctccctc    79620
accagcaccc ccaggcggcc tccctcgtgc tttcagagcc agcacagccc cagagggcca    79680
tctttgcttg aagccttctg tgggccgggg atgccaggag tcgtggtggg ctcttcctgc    79740
ctcaaaagcc acccccttctg gctaaaacga aggcactcct tggctggggg accgggtatt    79800
ctcacatgtg gtgtcaggtc ctacccgcag ctgacctttg gttatgggcg catgggagga    79860
aaggaggagg agggtttgtt ttccttcatt ataactcaca tcatacgagc agtcaggcag    79920
ccccacagtc gggctagggc ggggtgtggg agctgtctgc tagtgagcag tgtgtcctgg    79980 cgtgagggg cgggtagact aggtccagat ttgcaccaca cccagcagct gccctccagg    80040
agtgctgctg cctgagttct ggtgtcatgg gcacctcctg tgggctctga tcatgttgcg    80100
tgtgtgtgtg tgtgttggcc atactggtaa gtagctgctc tcctgtgccc ttgccctggg    80160
ccagttttct cagagtccag atttctcagc tccatttctg cctggcctca gcttgggcca    80220
gttgtagcca gtatacatga tggtccttca cagctctgct gaagtgagaa ttcgagttca    80280
tgcgctgctc acacaccagt ttgctgctgg cctcgggtgt ggagcaaggg cactgtctgt    80340
ctagaggctc ttaagctctg ccactgactt aaaggtgttc tgtggcctcc cctcctggcc    80400
caaagctgag caacagaagc ctctggacac accacctgca gtgagacctc aggtcttcac    80460
tcacagtcta atcagatgca ttaggcgagg ggactgcagc tcaggcaggc aactcacatg    80520
cttgaggcca cttggccacc aaatgtgggc ttccacctcg ggcccaactt tggcacttag    80580
atgccacctc cttccacaca ggcactggcc ttgctcccaa tcagtaacag caagcacaga    80640
gtcttcctaa agcaagtgaa ccctcaactc tgatgttcag ggacatggca tcaaatttga    80700
gcaaaggccc ctgactttc tgaataagga taatcatgt gtttggggat ttttttgggg    80760
gggggtcttt ggtgttttg agtcataggt gtacggtatt ggataaagaa ccaggcactc    80820
attgaaggct actacttacg aagctgtgaa aagcctggct tttaacaga aaaacagtat    80880 tttcttccc atgtccctgt aagaagtgtt ccacattagt tttacgtgga cgtttccaaa    80940
```

```
accttgatga aagaacttgt aagcacagtt gtaagggtga agggtagtta ctcttagtga   81000
gtcatgcaag tagtgaattg tatgagacac agcactagta tttctaaagc tacactgaag   81060
ctgcagaaaa cttggattta ttcaaggaaa aactatcttc ctgtctcctt gtaaagactt   81120
gcttttaaat cagatctata tagacgtttc ttacacgttg catgaaaaat ttgaggcatg   81180
atgttcttct gtatgacagt agccacccag gtgcccagtg ggcagtacct gaaaggaccc   81240
ttttatgtgt gtgtatgaag agtaaacagc ctgcgctgaa agctcgtcag tggagaaggt   81300
taagtaattg tcctgacgtg ggattctaga gattagagtg catgatgagc catctcagga   81360
caagagtatt cgctcctttg gtctcttttt tattttactt tttattttt ttgccacacg   81420 gcacaacctg tgggatccta gttcgctaac cagggaatca aacctgggcc cttggcagtg   81480
aaaatgcaga gtcccagcag ctggactgct ggggaactcc cctggtctcc tttaaaaaaa   81540
aaaaaaaact gggcagggag gacattaaaa agaacaaaga cattcctaat gtggcttctg   81600
ggggaagggg agcactggcg atcagatgga ccagggctc agagttgctg cctgtcctgg   81660
gccagatcgt gtccccgtgt cccactgcct gggacacaag aggggaagac aaaaatggcc   81720
acaggcaaaa caggttctac cgagatttga actcggatcg ctggattcaa agtccagagt   81780
gctaaccatt acaccataga accatatgcc attatgtccc cttgcaggtc actcttggcc   81840
taagtgcccc tggatgggga caagaggggt acacagttcc cactaagatt ttgacatctc   81900
tggattcaga gtccagagcg ctgatggtga cgccatagaa ctagctgcca ctcctggaca   81960
ccagggtcca cagcccaacc tagtcccaca gctggggacc caaaagctat agagcaggca   82020
aaaatgtgag ctcatagcag aggatggttt cgatccatcg acctctgggt tatgggccca   82080
gcacgctccc gctgcgccac tctgctgtaa tgtactcctt tcctgagtct gtctctgact   82140
accccaagct tccctgggca cagatcagca gacaaaaccg gacttggaga aggaccctct   82200
tgccagtgtc catttatgaa taaagtggat ttttgctctc cctctctcaa ctgcttaccc   82260
agagaaattt ctgtcctttc tgctgtttag taaaagtcaa gcagcacaat ctttacccag   82320
agtgtccttg gacaatggta gcaggatctc tattgcagtg atgctggctg gatctcggaa   82380
aaaagcaaaa gcagcatttc tctccatcat ttgaaagatt cctaatctgt ccaattgtca   82440
ttaactttcc ttttaatcca gtttcttctc gacctacttc ttcccccata gccaaggaaa   82500
ctgtttcttt catatgaaac tgcttaaagt gttacaaaat cttgctgttc agcttttctaa   82560 ttcgaaggaa aacatttaaa ataactttgc atttccaaga ggtaaaaatt gttctcccaa   82620
gtatatcctg aatataaatc ctttgggagg gggggaatc tttgaatttg tgttgaaact   82680
tttcatgtaa aaactgtcca tgaagcttac tgttgcagat agtaagctgt ctcctttctc   82740
acaccaacag aatcatcagg aaaaagaaat acagagactg aaactactgg aattctatga   82800
ccagactctg aacaccacac caatcaaagg actggaactt ttttttttt ttaacttctt   82860 attttatgtt agagtatagt gctagtttca ggtatacctc aaagtgattc ttttatacat   82920
agtcatgtat ctattttcc aaattctttt ctcatttagg ttgttacata ataccgagca   82980
gagttcctga gctaaacagt agtaggtcct tgttggttat tccttttaaa tatagcagtg   83040
tatacatgtt tccctggtgg ttcagatggt aaagcgtctg tctacaatgc gggagacctg   83100
ggttcgatcc ctgggtcggg aagttccctg gacaaggaaa aggcagccca ctccagtact   83160
cttgcctaga aaatcccatg gatggaggag cctggtgtcc atggggtcac aaagagtcgg   83220
acacgactga gcgactttac ttcacataca tgtcaatccc taactcccta tatatccctc   83280
ccccgtccct tctcctctgg taaccataaa ttcattctca taaatttatt cattcattct   83340
```

```
atgtctatga gtctgtgtct gccttgtaaa taagttcatt tgtatcattt tttagcctcc    83400
aaagggatat cacgcccaag atgtctagga tattgtttga gcctgataaa cctaactaca    83460
taggtacatc cggagggaaa aaggtagcca ctgggagaag acaaaggcaa cgcctctggg    83520
ccgcacatct catcaatgcc gggggcaggg cttagacaaa accagattgg aggattcggg    83580
tcaaagagct ttctgatgac gtgtgcggag ggactgctcc gaatgggcgc agaatttgag    83640
aagattcatg ttccacgcga aacctcttcc aaagggctct actgtgggaa aggctgacct    83700
aggttgccta gctagtctgc agatgtctgt cagactcttt tcagccatcc tgctgatgtt    83760
tcaccgtcag actgaactgg ctgtggcgac agggaaggag acaacatgca gtctcccacc    83820
aagcttgcct tggctgaccc tcacgtacaa gttatagtga ccaagcctcc attccaatat    83880
cgcttgccga tagagcgggc agccagccac ctgagagcta ggccacgtcg aacagaccc     83940 taagtccgca cctggactta atctgctttt ccttcgggac ccccactgtc ttcaccacac    84000
tctacacaac accgctcccg gcaaaccagg gggctttaca gtgacaggat tctgctcttg    84060
ggaaaggatt tctcttttca gtacctcagc gcccagaggc agtgccctag aaaggtgaga    84120
cagcgcctgt gcatttcctc accacacccg agaagtgaga gcggaggagc aaagcgaagg    84180
agctctccgt tcccgctcgg gaggaggccg cctcgctttc ggcctaaagc tctgtcgacc    84240
cgggaccctg ggctcacggc caagcccggc acccgctcca cttgtcggcg actgaagcgg    84300
ctgacgacgt ccgcccgccc gcggagtcag ccgggaactc gcccggtctc ggcagaaccg    84360
ggtttctacc tcacggcggc tccagcagtc atgtgggcgg ggtcacgtgg actggcagtc    84420
acgtgtcctg aggacgtctg cgtgcgacgt ccgcgctccc gcgctcccca gtgggatgtg    84480
tgcgtttcgc accttgcggc gtgggtaagg gtaccctgag ggccgcacgt tagacagcgt    84540
gccctctgga gctgctcctc cgcggggcca cgctgacaga ggccctggcc gtttcgaccc    84600
tgcgcgctcc ggatcggact ccaggtgtcc cgctccccgc agggcccagg atgggtgggg    84660
tctccagtta gtgctgtttg gagctccctt tttaacaaga atgcgaaatt agatacgaag    84720
gtgaatgttg attataataa gaaaagtcaa ttatacacag ctgattaata tcacaaacca    84780
agcaaagcac aaagcttttc tctagttaat tgcctaacgc ctcaattttt tttccaattt    84840
ttaaaatgca gaccttaatt actccttcat atgggaatga tttggtaata ctgtttgtac    84900
aggataaaca gataattcac ttttgagcgg ggttaatcaa attttgctct tagtagtagt    84960
ttggaaaagg ttgttagcct tgcattcctt tggtaatgtt actattcttt tagggttgcc    85020
ctcagatttg gccaaaccta tcctgtgtct ggagtggcct cacagtggct tgttaggagc    85080
tttgtgtcat gtattccatg atctgtattt catgtcagat caggaagaaa tggaaagcgc    85140
tttccatgtt tgctttactc atctaaattg gatcaggtgt gtttctgccc tccttgtgga    85200
aggagcctac tctgttcatg tgattcctgt gtggccaaac atggacttcc caggggactc    85260
agtgatactc tgcctgccaa tccaggagac aacaggagag gagggtttga ccctgggtg    85320 gggaagatct cctagaggaa gaaatggcaa cccactccag tactcttgcc tggaaaattc    85380
catggacaga ggagcctggc tagctgcagt tcatggggtt gcagagtcag acacagtatt    85440
caaatacgca tgcttatatg ctgtgcgcag tccatgagtt ttgatggttc taaagatatt    85500
cactaaaatg aaagtctgat gtaagtgata tctgtcttgt tgaaaactgt aatgcaaaac    85560
aatacaggca atgtttagtc ttggaatagg ctagccaata tcatgtaaca gatttcctgt    85620
taagaaataa ctcttttcaaa atgtttcaag aagcatcttt ttcgtccatt gtaccttgat   85680
tctttgtaaa tgggattaca attttgaaaa aaacggattt ttcattaaac agagtttagg    85740
```

```
gaattattga gtgaagcatc acagtgatca atgaagtata taatcagtgg gtggggccac   85800
ctggtgtgtc ctgctgacta gagggttgtg gttttccttt ctgttaccat catcttcctt   85860 ctgcttttt  tttttttccc ttgttttttt tttttttctt cctgttaaga catattctga   85920
ctctcataat acctttcatc tgttttgtca tttttattac ccatattttc ttggctatca   85980
tgattcttcc atgattttta tcattacagt ttttagtttc catcgtggta tgctgctgct   86040
gccgctgcta agttgcttca gtcatgtcca actctgtgtg accccacaga tggaagccca   86100
ccaggcttcc ccatccctgg gattctccag gcaagaacac tggagtgggt tgccatttcc   86160
tcctccattg catgaaagtg aaaagtgaaa gtgaagtcac tcagtcgtat ccgactctta   86220
gcaaccccat ggactgtagc cctccaggct cctccatcca tgggattttc caggcaagag   86280
tactggagtg gggtgccatt gccttctccg ccattgtggt atacttttttg atattttgaa   86340 gtttctgcca gacttttttct tttagttttt tttcccttt tttccttctt tccagtaaga   86400
tacttccttc tgtttcaatt ttgatatgat gggtaattct ttaaaagtat acgaagttaa   86460
tctgaattta aggcaactac aagttcaact caaatacatt tcttattggc cctacaagta   86520
ctgagcttcg tgactatgta atgaaataat catataccac atccagtgat ttagtggtga   86580
atgagtaagg agttccacca caggaaaatg aatttattca ggccctttttg ctgtgtcatg   86640 tgaaggttga aatgagttca tactgatgtt ttcagctctt gtccggaaac acgtggtttc   86700
ctccagcccc tccttacttc tctgtagctc actatccaac acaagaaatc ttcttcgccc   86760
acttttaaca attgtggtat ttgatttgtt agagccaggg tttgtgtcgc atctttttat   86820
ttcctaaatg aagcacagtg tctcctgtgg atgtagctct gcattgatgt tgaattgaca   86880
tgtttaactt tgattttttgc catcagaatt ctctacagaa gagttgcatc agcttctgtg   86940
ctcatgttct gcctgcctgc tgctgctgcc tgcttcctct caatttctta tccctaaccc   87000
agggccagca ggatgaggca aggttttcat cttggtcctc cgtgtttcaa tccataggct   87060
cagagaagtt ttccgcctgg gccagtggac agtaactgat tggaatataa tcattcgctc   87120
attatgtcac tttcccaaac ttactctgca tcaggccagc actaatcagg agctccacct   87180
caaagctcag agtcctgttg ggataatgtg cataatgact gtctcagact gtgagatgga   87240
aaccaggtgg gtacaaagca ggtccaaggg aggagcagtt ctcactgtgt ggcaggggc    87300 tggggtggct gatggagacg ccatgggagc tgggtcttcc attcaggtgg cttggttagc   87360
atgtgagggg aggggaaccc ggggaaggag ctatgtgtga ggaagtttgg gttgctggtc   87420
caggtgagga gtgctgaatc aaggctgcct ccctttcctg gccgatgaag gcagggcctg   87480 tgtcccctt  gctccctgtg gccagggca tccagcactg gcccagcat gaggaatgtt    87540 tgatgagtgg acaagctagt gaatgaatga atgaaaaaat gaatgcatga atgggtgatg   87600
agtaacccat gaatcaaaat ttccccagag gtttagagct caggcaatga gaggaccagg   87660
gatgcttaga caaacactga gaagctacag cccaggtgga gtgggctgg agctggggcc    87720 cgagtccagg caacggaagc tcctttattc agaaacagcc tttagctatt gaattttctg   87780
tcctgctgtg ttttgcacat ttccatgttt ctgttttggg ggacgctaac atccttgact   87840
ggagatgacg ctaaggcaac tgacctggct ggccctggga cactggtcac tacaaggggc   87900
atgcgcctca taccttcatc tccttcttcc aggccgtccc tggtgttctt ctcaaactta   87960
ggtaaatatg ccttagaaca cagaggcata gggggcacct tctgagggct gcctttccgg   88020
gcccattgcc gtaatccagg aggtaagtag tgtacacata gccaagtatg tgatggtttc   88080
tatgatatgt gtgaagaatt acataggggac acacccacag acccgctttc tgccccagg   88140
```

```
cgtacagagt gatcatgcct ccccagttt  ccaaatcacc taagggaggt ctttggagaa    88200
gagattttgg tggaggagga ttagaaacgc actttcaggt ccagttaata tcaataagtt    88260
taaggatatt ttcagaattt ttttttttaa ttggtattat aagatttatc tctgaagctc    88320
tcattttttt aaagaatgca attcaactag gaatgtgttt attttcacc  tataaaattc    88380 agtttccaaa agtcagatgg agtttaaaac atttaccaac ttttaagtgc tctaatgaaa    88440
atgtaatttt aaattgcaat tacattagtg agacacgtgg gacttctcta gtggtccagt    88500
ggttaagact ctgagctccc aatgtagggg tcgtgggttc aatccctggt tggtaaacta    88560
agatcccaca tgccgtgcag tgcggcaaaa aaagttaaa  aaaagtgag  acatgtttat    88620 tattctttt  tattagggaa aagggcagaa tcctaataag cggaagtagc tcacgtgagc    88680
agctgagtga gtgttgttct gggcctttcc tggtgagtag gtggtagatc agccttatgg    88740
ggcacacaca tccccattac cacacctggg cagagtcacc ccttcatttc ttttttttt     88800 ttttcatggt ttcttcactt ttatttaggt aatgtaattt aatgcataca ttaaactgtt    88860 aaaaaaatc  agtaaatgga atcacaccaa ggaaaatctg catgctgttt ccactagaaa    88920
aatattatct atataaaatt tggtccagtt tcttctcctt tatctctgcc attcaaattt    88980
aaatgcttta attttattca agcaaaaatc acatatctga cataataaaa tacttcacat    89040
cattaaatta atagggttta gttgaattag gtgtgctcat ctttcctatg ttatttctct    89100
acttttattc ttctgagtta actcagtaag gcatgtctgt tttcccacat ccagcaatac    89160
aagtgttaca gaagtataat ttgtaacatt agtaactaga ttcatcatta atcttcaatt    89220
catgtttccc ttattatatg gtatttccat atttctagat atttcaatct tacactttcc    89280
aacaaggatt aagccattag tttaaaaata ctattaaatt tccagactaa ataacacttg    89340
gcccacttag agtgatgctg tcgtgagagg tccttgcaca gctattgctt caatctcaac    89400
acggcctcgt ttgggcaaag cagcaacctg gtaagcagct ctcgcaggaa aactactctg    89460
gaaatattgt ttgtagacat tgttgacagt actgaagtca tttatgtcag tcagcaaaac    89520
agttgctttt actacattcg tgaagtcaca gcctgctgct ttcagaattt cacttatgtt    89580
tgtaagagcc tgtttagcct cttctgccac ccctcctggc acaagctgtc cacttgcagg    89640
gtccatgcct agttgtcctg aaatgtacat ggtcctgtcg actaacacag cctgactgta    89700
gggaccaatg gccgcggggg ctttcgcggt gctgattatc tttctgacca gaaacaacat    89760
ggttaaccct tttcccttgc tgccccttgg aaacaactat gcagaactcg gttctcgctt    89820
gctcttcacc tccccttcat ttctttaatg tgtgggtgtc ctagtatatt cagccggctg    89880
ccactgatgt acattacaga actatgtgaa tttccatttt gaaccctgca ggaatcaacc    89940
aagcacaact gtgctggtaa cttgtaaatt cctgcacctg gaatgtccag gtctgaagac    90000
accacacttc cagctttgct ctatttgaac aaccgtgtgg ctcagaccat gaactcctta    90060
ctgccaaatt cagacttaaa ttgaagaaag tagggaaaaa ccacgagacc attcaggtat    90120
gacctaaatc aaatccctta tgattataca gtggaagtga gaaatagatt gaagggccta    90180
gatctgatat atagagtgcc tgatgcacta tagaatgagg ttcgtgacat tgtacaggag    90240
acagggatca agaccatccc catggaaaag aaatgcaaaa aagcaaaatg gctgtcggga    90300
gaggccttac aaatagctgt gaaagaagaa gaagcgaaaa gcaaggagaa aaggaaaga    90360 tataaatctg aatgcagagt tccaaagaat agcaagaaga gataagaaag ccttcttcag    90420
cgatcaatgc aaagaaatag aggaacacaa cagaatggga aagactaggg atctcttcaa    90480
gaaaattaga gataccaagg gaacatttca tgcaaagatg ggctcaataa aggacagaaa    90540
```

```
tggtagggac ctaacagaag cagaagatat taagaagaga tggcaagaat acacagaaga    90600
actgtacaaa aaagatcttc acgacccaga taatcacgat ggtgtgatca ctgacctaga    90660
gccagacatc ctggaatgtg aagtcaagtg ggccttagaa agcatcatta tgaacaaagc    90720
tagtggaggt gatagaattc cagttgagct attccaaatc ctgaaagatg atgctgtgaa    90780
agagctgcac tcaatatgct agcaaatttg gaaaactcag cagtggccac aggactggaa    90840
aaggtcagtt ttcattccag tcccaaagaa aggcaatgcc aaagaatgct caaactaccg    90900
cacaattgca ctcatctcac acactagtaa agtaatgctc aaaattctcc aagccaggct    90960
tcagcaatac gtgaactgtg aacttcctga tgttcaagct ggttttagaa aaggaagagg    91020
aaccagagat caaattgcca acatctgctg gatcatggaa aaagcaagag agttccagaa    91080
aaacatctat ttctgcttta ctgaccatgc caaagccttt gtgtggatca caataaactg    91140
tggaaaattc cgaaagagat gggaatacca gaccacctga cctgcctctt aagaaatctg    91200
tatgcaggtt aggaaacaac agttagaact ggacatggaa caacagactg gttccaaaca    91260
ggaaaaggag tacgtcaagg ctgtatatcg ttaccctgtt tatttaactt acatgcagag    91320
tacatcatga gaaacgctgg actggaagaa acacaagctg gaatcaagat tgctgggaga    91380
aatatcaata acctcagata tgcagatgac accacccctta tggcagaaag tgaagaggaa    91440
ctaaaaagcc tcttgatgaa agaggagagt gaaaaagttg gcttaaagct caacattcag    91500
aaaacgaaga tcatggcatc tggtcccatc acttcatggg aaatagatgg ggaaacggtg    91560
gaaacagtgt cagactttat ttttctgggc tccaaaatca ctgcagatgg tgactgcagc    91620
catgaaatta aaagacactt actccttgga aggaaagttt tgaccaacct agatagcata    91680
ttcaaatgca gagacattac tttgccaaca aaagtttgtt tagtcaaggc tatggttttt    91740
cctgtggtca tgtatggatg tgagagttgg actgtgaaga aggctgagcg ccaaagaatt    91800
gatgcttttg aactgtggtg ttggagaaga ctcttgagag tcccttggac cgcaaagaat    91860
tgatgctttt gaactgtggt gttggagaag agtcttgaga gtcccttgga ctgcaaggag    91920
atccaaccag tccattctga aggagatcag ccctgggatt tctttggaag gaatgatgct    91980
gaagctgaaa ctccagtact ttggccacct catgcgaaga gttgactcat tggaaaagac    92040
tctgatgcag ggagggattg ggggcaggag gagaaggggga cgccagagga agagatggct    92100
ggatggcatc actgacttga tggacgtgag tctgagtgaa ctccgggagt tggtgatgga    92160
cagggaggcc tggcgtgctg cgattcatgg ggtcaaacag agtcggacac gactgagcga    92220
ctgatctgat ctgatctgat ctgtggaaac tcaaaacact ttccacaaaa tgctgatacg    92280
aggaagcaca aaagggctca agagagcctg caccgcctcc ctggaacccg ggaacccggg    92340
aggcgctgat acgaggaagc acaaaagggc tcaagagagc ctgcactgcc tccctggaac    92400
cctggaaccc ggagggcgcc ccgtcccgct gtgctcagcc cctccatttg tttcttatgt    92460
gcctgttgaa ggcacttggg tgtttgagcc tgacttccct ggtggctcag atggttaagt    92520
gtctgcccac aatgtgggag acctgagttc aatccctggg tcgggaagat ctcctggaga    92580
aagaaatggc aacccactcc agtgttcttg ccccaaaaat cccatggaca gaggaacctg    92640
gtaggctacc gtccatgggg tcgcaaagag tcggacatga ctgagcaact tcactttcac    92700
tttggttatt atgaatagag ctgttatgaa tattcttaaa aagcaatttt gcaggcatct    92760
gcattcttct ctcttgggca atacctgggc ggggggggggg atggctagag ctacacttat    92820
gtggtcgggg tctgtggtgt gtgtgtgtag tactttatgt attaataagg attaataatt    92880
aatacataaa gtattaatac agccccacca gtttccaaat cacctacggg aggtctctgg    92940
```

```
agaagagctt ttggtggtgg aggattggaa acatactttc cagccaatat cagtaaattg    93000
aagggtattt tcagtatttt ttaaattggt gttataagat ttatctctga agcttttgat    93060
aatgaatgaa attcgactag gaatgtagta ttcacctata aaactcattc tttccaaaaa    93120
tggagtttaa aacattttac caatttttaa gtgatctact tatgtttgcc aaccttaatt    93180
gcattttaaa actgtcatta tgaaagtgag acacgtggga cttccctagc ggtccagtgg    93240
ttaagactct gagcttccaa tgcaggggcc gtgggcactt tatcattctt tatcattcat    93300
tctcttcctt ggtggctcag acggtaaaga atgtgcctgc aatgcaggag acccggttca    93360
atcccgggtg tgaccggaaa aaaaaaaaaa aaaaagttaa aaaggtgaga catgtttatt    93420
attctttttt attatggaaa agggcagaat cctagtaagt ggg                      93463
```